(12) United States Patent
Brunner et al.

(10) Patent No.: US 8,618,046 B2
(45) Date of Patent: Dec. 31, 2013

(54) TREATMENT OF ATHEROSCLEROSIS WITH CHOLESTEROL ESTER TRANSPORT PROTEIN MIMOTOPES

(75) Inventors: Sylvia Brunner, Vienna (AT); Petra Luehrs, Vienna (AT); Frank Mattner, Vienna (AT); Walter Schmidt, Vienna (AT); Barbara Wittmann, Traiskirchen (AT)

(73) Assignee: Affiris AG, Vienna (AT)

( * ) Notice: Subject to any disclaimer, the term of this patent is extended or adjusted under 35 U.S.C. 154(b) by 549 days.

(21) Appl. No.: 12/673,081

(22) PCT Filed: Aug. 8, 2008

(86) PCT No.: PCT/AT2008/000281
§ 371 (c)(1),
(2), (4) Date: Feb. 11, 2010

(87) PCT Pub. No.: WO2009/021254
PCT Pub. Date: Feb. 19, 2009

(65) Prior Publication Data
US 2011/0275556 A1  Nov. 10, 2011

(30) Foreign Application Priority Data
Aug. 10, 2007  (AT) ................ A 1258/2007

(51) Int. Cl.
*A61K 38/10* (2006.01)
*A61K 38/04* (2006.01)
*A61P 9/10* (2006.01)
*C07K 7/08* (2006.01)

(52) U.S. Cl.
USPC ........... 514/1.9; 514/21.4; 514/21.5; 530/326

(58) Field of Classification Search
None
See application file for complete search history.

(56) References Cited

U.S. PATENT DOCUMENTS

2006/0276400 A1  12/2006  Adari et al.
2007/0166788 A1*  7/2007  Jin et al. .................. 435/69.1
2009/0104211 A1*  4/2009  Mattner et al. ............ 424/184.1

FOREIGN PATENT DOCUMENTS

CA  2580261  3/2006
WO  1996 034888  11/1996
WO  WO 2006/029982  * 3/2006

OTHER PUBLICATIONS

Petra Burgstaller, et al., "Aptamers and aptazymes: Accelerating small molecule drug discovery", Current Opinion in Drug Discovery & Development, vol. 5, No. 5, 2002, pp. 690-700.

Michael Famulok, et al., "Nucleic Acid Aptamers-From Selection in Vitro to Applications in Vivo", Accounts of Chemical Research, vol. 33, No. 9, 2000, pp. 591-599.

Derek T. O'Hagan, et al., "Recent Advances in the Discovery and Delivery of Vaccine Adjuvants", Nature Reviews, Drug Discovery, vol. 2, Sep. 2003, pp. 727-735.

Rajesh Krishna, et al., "Effect of the cholesteryl ester transfer protein inhibitor, anacetrapib, on lipoproteins in patients with dyslipidaemia and 24-h ambulatory blood pressure in healthy individuals: two double-blind, randomised placebo-controlled phase I studies", www.thelancet.com, vol. 370, Articles, Dec. 8, 2007, pp. 1907-1914.

Dan Mao, et al., "Intramuscular immunization with a DNA vaccine encoding a 26-amino acid CETP epitope displayed by HBc protein and containing CpG DNA inhibits atherosclerosis in a rabbit model of atherosclerosis", Vaccine 24, 2006, (Elsevier Ltd.), pp. 4942-4950.

Günter Mayer, et al., "Controlling small guanine-nucleotide-exchange factor function through cytoplasmic RNA intramers", PNAS, vol. 98, no. 9, Apr. 24, 2001, pp. 4961-4965.

James A. Sikorski, et al., "Oral Cholesteryl Ester Transfer Protein (CETP) inhibitors: A Potential New Approach for Treating Coronary Artery Disease", Journal of Medical Chemistry, vol. 49, No. 1, Perspective, Jan. 12, 2006, 22 pages.

Manmohan Singh, et al., "Advances in vaccine adjuvants", Nature Biotechnology, vol. 17, (Nature America Inc.), Nov. 1999, pp. 1075-1081.

Daniel Steinberg, "An interpretive history of the cholesterol controversy, part V: The discovery of the statins and the end controversy[1]", Journal of Lipid Research, vol. 47, (Thematic review series: The Pathogenesis of Atherosclerosis), 2006, pp. 1339-1351.

Daniel Steinberg, "An interpretive history of the cholesterol controversy, part II: the early evidence linking hypercholesterolemia to coronary disease in humans[1]", Journal of Lipid Research, vol. 46, (Thematic review series: The Pathogenesis of Atherosclerosis), 2005, pp. 179-190.

William G. T. Willats, "Phage display: practicalities and prospects", Plant Molecular Biology 50:, 2002, pp. 837-854.

Examination Report w/English translation as received in the corresponding Taiwan Application No. 097130215 dated May 8, 2013.

* cited by examiner

*Primary Examiner* — Kevin S Orwig
(74) *Attorney, Agent, or Firm* — Oblon, Spivak, McClelland, Maier & Neustadt, L.L.P.

(57) ABSTRACT

The present invention relates to a method for treating atherosclerosis and/or atherosclerosis sequelae with a compound that includes $FX_8(F)_oPX_9HX_{10}X_{11}X_{12}DX_2X_3X_4X_5X_6X_7$ where $X_8$ is G, A, F, Y or K, $X_9$ is E, Y, A, Q, K or S, $X_{10}$ is H, V, L, F or I, $X_{11}$ is L, W, S, I, F or Y, $X_{12}$ is V, T, F or I, $X_5$ is S or Y, $X_6$ is L, A or I, $X_7$ is S, N or T, and o is 0 or 1.

10 Claims, 28 Drawing Sheets

```
                          SEQUENCE LISTING

<160> NUMBER OF SEQ ID NOS: 270

<210> SEQ ID NO 1
<211> LENGTH: 6
<212> TYPE: PRT
<213> ORGANISM: Artificial Sequence
<220> FEATURE:
<223> OTHER INFORMATION: CETP mimotope
<220> FEATURE:
<221> NAME/KEY: MISC_FEATURE
<222> LOCATION: (1)..(1)
<223> OTHER INFORMATION: Xaa is (Xaa)n and an amino acid residue other
      than C, wherein n is an integer between 0 and 9
<220> FEATURE:
<221> NAME/KEY: MISC_FEATURE
<222> LOCATION: (2)..(2)
<223> OTHER INFORMATION: Xaa is an amino acid residue selected from the
      group consisting of D, A, R, E, S, N, T and G
<220> FEATURE:
<221> NAME/KEY: MISC_FEATURE
<222> LOCATION: (3)..(3)
<223> OTHER INFORMATION: Xaa is an amino acid residue selected from the
      group consisting of F, A, W, R, S, L, Q, V and M
<220> FEATURE:
<221> NAME/KEY: MISC_FEATURE
<222> LOCATION: (4)..(4)
<223> OTHER INFORMATION: Xaa is an amino acid residue selected from the
      group consisting of L, A, S, W, E, R, I and H
<220> FEATURE:
<221> NAME/KEY: MISC_FEATURE
<222> LOCATION: (5)..(5)
<223> OTHER INFORMATION: Xaa is an amino acid residue selected from the
      group consisting of Q, A, H, D, K, R, S and E
<220> FEATURE:
<221> NAME/KEY: MISC_FEATURE
<222> LOCATION: (6)..(6)
<223> OTHER INFORMATION: Xaa is (Xaa)m and an amino acid residue other
      than C, wherein m is an integer between 0 and 9

<400> SEQUENCE: 1

Xaa Xaa Xaa Xaa Xaa Xaa
1               5

<210> SEQ ID NO 2
<211> LENGTH: 7
<212> TYPE: PRT
<213> ORGANISM: Artificial Sequence
<220> FEATURE:
<223> OTHER INFORMATION: CETP mimotope

<400> SEQUENCE: 2

Ser Tyr His Ala Thr Phe Leu
1               5

<210> SEQ ID NO 3
<211> LENGTH: 7
<212> TYPE: PRT
<213> ORGANISM: Artificial Sequence
<220> FEATURE:
```

-continued

<223> OTHER INFORMATION: CETP mimotope

<400> SEQUENCE: 3

Thr Met Ala Phe Pro Leu Asn
1               5

<210> SEQ ID NO 4
<211> LENGTH: 7
<212> TYPE: PRT
<213> ORGANISM: Artificial Sequence
<220> FEATURE:
<223> OTHER INFORMATION: CETP mimotope

<400> SEQUENCE: 4

His Tyr His Gly Ala Phe Leu
1               5

<210> SEQ ID NO 5
<211> LENGTH: 7
<212> TYPE: PRT
<213> ORGANISM: Artificial Sequence
<220> FEATURE:
<223> OTHER INFORMATION: CETP mimotope

<400> SEQUENCE: 5

Glu His His Asp Ile Phe Leu
1               5

<210> SEQ ID NO 6
<211> LENGTH: 7
<212> TYPE: PRT
<213> ORGANISM: Artificial Sequence
<220> FEATURE:
<223> OTHER INFORMATION: CETP mimotope

<400> SEQUENCE: 6

Thr Gly Leu Ser Val Phe Leu
1               5

<210> SEQ ID NO 7
<211> LENGTH: 7
<212> TYPE: PRT
<213> ORGANISM: Artificial Sequence
<220> FEATURE:
<223> OTHER INFORMATION: CETP mimotope

<400> SEQUENCE: 7

Trp Met Pro Ser Leu Phe Tyr
1               5

<210> SEQ ID NO 8
<211> LENGTH: 7
<212> TYPE: PRT
<213> ORGANISM: Artificial Sequence
<220> FEATURE:
<223> OTHER INFORMATION: CETP mimotope

<400> SEQUENCE: 8

Ser Met Pro Trp Trp Phe Phe
1               5

<210> SEQ ID NO 9
<211> LENGTH: 7
<212> TYPE: PRT
<213> ORGANISM: Artificial Sequence
<220> FEATURE:
<223> OTHER INFORMATION: CETP mimotope

```
<400> SEQUENCE: 9

Thr Met Pro Leu Leu Phe Trp
1               5

<210> SEQ ID NO 10
<211> LENGTH: 7
<212> TYPE: PRT
<213> ORGANISM: Artificial Sequence
<220> FEATURE:
<223> OTHER INFORMATION: CETP mimotope

<400> SEQUENCE: 10

Asp Thr Trp Pro Gly Leu Glu
1               5

<210> SEQ ID NO 11
<211> LENGTH: 7
<212> TYPE: PRT
<213> ORGANISM: Artificial Sequence
<220> FEATURE:
<223> OTHER INFORMATION: CETP mimotope

<400> SEQUENCE: 11

Ser Met Pro Pro Ile Phe Tyr
1               5

<210> SEQ ID NO 12
<211> LENGTH: 7
<212> TYPE: PRT
<213> ORGANISM: Artificial Sequence
<220> FEATURE:
<223> OTHER INFORMATION: CETP mimotope

<400> SEQUENCE: 12

Met Pro Leu Trp Trp Trp Asp
1               5

<210> SEQ ID NO 13
<211> LENGTH: 7
<212> TYPE: PRT
<213> ORGANISM: Artificial Sequence
<220> FEATURE:
<223> OTHER INFORMATION: CETP mimotope

<400> SEQUENCE: 13

Ser Met Pro Asn Leu Phe Tyr
1               5

<210> SEQ ID NO 14
<211> LENGTH: 7
<212> TYPE: PRT
<213> ORGANISM: Artificial Sequence
<220> FEATURE:
<223> OTHER INFORMATION: CETP mimotope

<400> SEQUENCE: 14

Arg Met Pro Pro Ile Phe Tyr
1               5

<210> SEQ ID NO 15
<211> LENGTH: 7
<212> TYPE: PRT
<213> ORGANISM: Artificial Sequence
<220> FEATURE:
<223> OTHER INFORMATION: CETP mimotope

<400> SEQUENCE: 15
```

```
Asn Pro Phe Glu Val Phe Leu
1               5

<210> SEQ ID NO 16
<211> LENGTH: 7
<212> TYPE: PRT
<213> ORGANISM: Artificial Sequence
<220> FEATURE:
<223> OTHER INFORMATION: CETP mimotope

<400> SEQUENCE: 16

Thr Leu Pro Asn Trp Phe Trp
1               5

<210> SEQ ID NO 17
<211> LENGTH: 7
<212> TYPE: PRT
<213> ORGANISM: Artificial Sequence
<220> FEATURE:
<223> OTHER INFORMATION: CETP mimotope

<400> SEQUENCE: 17

Ser Met Pro Leu Thr Phe Tyr
1               5

<210> SEQ ID NO 18
<211> LENGTH: 7
<212> TYPE: PRT
<213> ORGANISM: Artificial Sequence
<220> FEATURE:
<223> OTHER INFORMATION: CETP mimotope

<400> SEQUENCE: 18

Ser Pro His Pro His Phe Leu
1               5

<210> SEQ ID NO 19
<211> LENGTH: 7
<212> TYPE: PRT
<213> ORGANISM: Artificial Sequence
<220> FEATURE:
<223> OTHER INFORMATION: CETP mimotope

<400> SEQUENCE: 19

Asn Phe Met Ser Ile Gly Leu
1               5

<210> SEQ ID NO 20
<211> LENGTH: 7
<212> TYPE: PRT
<213> ORGANISM: Artificial Sequence
<220> FEATURE:
<223> OTHER INFORMATION: CETP mimotope

<400> SEQUENCE: 20

Ser Gln Phe Leu Ala Ser Leu
1               5

<210> SEQ ID NO 21
<211> LENGTH: 7
<212> TYPE: PRT
<213> ORGANISM: Artificial Sequence
<220> FEATURE:
<223> OTHER INFORMATION: CETP mimotope

<400> SEQUENCE: 21

Trp Ser Trp Pro Gly Leu Asn
1               5
```

```
<210> SEQ ID NO 22
<211> LENGTH: 7
<212> TYPE: PRT
<213> ORGANISM: Artificial Sequence
<220> FEATURE:
<223> OTHER INFORMATION: CETP mimotope

<400> SEQUENCE: 22

Ile Ala Trp Pro Gly Leu Asp
1               5

<210> SEQ ID NO 23
<211> LENGTH: 7
<212> TYPE: PRT
<213> ORGANISM: Artificial Sequence
<220> FEATURE:
<223> OTHER INFORMATION: CETP mimotope

<400> SEQUENCE: 23

Ser Lys Phe Met Asp Thr Leu
1               5

<210> SEQ ID NO 24
<211> LENGTH: 7
<212> TYPE: PRT
<213> ORGANISM: Artificial Sequence
<220> FEATURE:
<223> OTHER INFORMATION: CETP mimotope

<400> SEQUENCE: 24

Ser Met Pro Met Val Phe Tyr
1               5

<210> SEQ ID NO 25
<211> LENGTH: 7
<212> TYPE: PRT
<213> ORGANISM: Artificial Sequence
<220> FEATURE:
<223> OTHER INFORMATION: CETP mimotope

<400> SEQUENCE: 25

Tyr Glu Trp Val Gly Leu Met
1               5

<210> SEQ ID NO 26
<211> LENGTH: 7
<212> TYPE: PRT
<213> ORGANISM: Artificial Sequence
<220> FEATURE:
<223> OTHER INFORMATION: CETP mimotope

<400> SEQUENCE: 26

Lys Gly Phe Leu Asp His Leu
1               5

<210> SEQ ID NO 27
<211> LENGTH: 12
<212> TYPE: PRT
<213> ORGANISM: Artificial Sequence
<220> FEATURE:
<223> OTHER INFORMATION: CETP mimotope

<400> SEQUENCE: 27

His Gln Ser Asp Asp Lys Met Pro Trp Trp Phe Phe
1               5                   10
```

```
<210> SEQ ID NO 28
<211> LENGTH: 12
<212> TYPE: PRT
<213> ORGANISM: Artificial Sequence
<220> FEATURE:
<223> OTHER INFORMATION: CETP mimotope

<400> SEQUENCE: 28

Tyr Val Trp Gln Asp Pro Ser Phe Thr Thr Phe Phe
1               5                   10

<210> SEQ ID NO 29
<211> LENGTH: 12
<212> TYPE: PRT
<213> ORGANISM: Artificial Sequence
<220> FEATURE:
<223> OTHER INFORMATION: CETP mimotope

<400> SEQUENCE: 29

Tyr Val Trp Gln Asp Pro Ser Phe Thr Thr Phe Phe
1               5                   10

<210> SEQ ID NO 30
<211> LENGTH: 12
<212> TYPE: PRT
<213> ORGANISM: Artificial Sequence
<220> FEATURE:
<223> OTHER INFORMATION: CETP mimotope

<400> SEQUENCE: 30

Leu Pro Gln Thr His Pro Leu His Leu Leu Glu Asp
1               5                   10

<210> SEQ ID NO 31
<211> LENGTH: 12
<212> TYPE: PRT
<213> ORGANISM: Artificial Sequence
<220> FEATURE:
<223> OTHER INFORMATION: CETP mimotope

<400> SEQUENCE: 31

Gly Pro Val Ser Ile Tyr Ala Asp Thr Asp Phe Leu
1               5                   10

<210> SEQ ID NO 32
<211> LENGTH: 12
<212> TYPE: PRT
<213> ORGANISM: Artificial Sequence
<220> FEATURE:
<223> OTHER INFORMATION: CETP mimotope

<400> SEQUENCE: 32

Asp Ser Asn Asp Thr Leu Thr Leu Ala Ala Phe Leu
1               5                   10

<210> SEQ ID NO 33
<211> LENGTH: 12
<212> TYPE: PRT
<213> ORGANISM: Artificial Sequence
<220> FEATURE:
<223> OTHER INFORMATION: CETP mimotope

<400> SEQUENCE: 33

Asn Gly Ser Pro Ala Leu Ser His Met Leu Phe Leu
1               5                   10

<210> SEQ ID NO 34
<211> LENGTH: 12
```

```
<212> TYPE: PRT
<213> ORGANISM: Artificial Sequence
<220> FEATURE:
<223> OTHER INFORMATION: CETP mimotope

<400> SEQUENCE: 34

Thr Asp Tyr Asp Pro Met Trp Val Phe Phe Gly Tyr
1               5                   10

<210> SEQ ID NO 35
<211> LENGTH: 12
<212> TYPE: PRT
<213> ORGANISM: Artificial Sequence
<220> FEATURE:
<223> OTHER INFORMATION: CETP mimotope

<400> SEQUENCE: 35

Ile Phe Pro Leu Asp Ser Gln Trp Gln Thr Phe Trp
1               5                   10

<210> SEQ ID NO 36
<211> LENGTH: 12
<212> TYPE: PRT
<213> ORGANISM: Artificial Sequence
<220> FEATURE:
<223> OTHER INFORMATION: CETP mimotope

<400> SEQUENCE: 36

Asn Glu Ser Met Pro Asp Leu Phe Tyr Gln Pro Ser
1               5                   10

<210> SEQ ID NO 37
<211> LENGTH: 12
<212> TYPE: PRT
<213> ORGANISM: Artificial Sequence
<220> FEATURE:
<223> OTHER INFORMATION: CETP mimotope

<400> SEQUENCE: 37

Asp Trp Gly Asp Lys Tyr Phe Ser Ser Phe Trp Asn
1               5                   10

<210> SEQ ID NO 38
<211> LENGTH: 7
<212> TYPE: PRT
<213> ORGANISM: Artificial Sequence
<220> FEATURE:
<223> OTHER INFORMATION: CETP mimotope

<400> SEQUENCE: 38

Val Ser Ala Tyr Asn Asn Val
1               5

<210> SEQ ID NO 39
<211> LENGTH: 7
<212> TYPE: PRT
<213> ORGANISM: Artificial Sequence
<220> FEATURE:
<223> OTHER INFORMATION: CETP mimotope

<400> SEQUENCE: 39

Trp Pro Leu His Leu Trp Gln
1               5

<210> SEQ ID NO 40
<211> LENGTH: 17
<212> TYPE: PRT
<213> ORGANISM: Artificial Sequence
```

```
<220> FEATURE:
<223> OTHER INFORMATION: CETP mimotope

<400> SEQUENCE: 40

Cys Phe Gly Phe Pro Glu His Leu Leu Val Asp Phe Leu Gln Ser Leu
1               5                   10                  15

Ser

<210> SEQ ID NO 41
<211> LENGTH: 6
<212> TYPE: PRT
<213> ORGANISM: Artificial Sequence
<220> FEATURE:
<223> OTHER INFORMATION: CETP mimotope
<220> FEATURE:
<221> NAME/KEY: MISC_FEATURE
<222> LOCATION: (1)..(1)
<223> OTHER INFORMATION: Xaa is P, Y, T or K
<220> FEATURE:
<221> NAME/KEY: MISC_FEATURE
<222> LOCATION: (2)..(2)
<223> OTHER INFORMATION: Xaa is an amino acid residue other than C
<220> FEATURE:
<221> NAME/KEY: MISC_FEATURE
<222> LOCATION: (4)..(4)
<223> OTHER INFORMATION: Xaa is Y, L, H, V, T, I or F
<220> FEATURE:
<221> NAME/KEY: MISC_FEATURE
<222> LOCATION: (5)..(5)
<223> OTHER INFORMATION: Xaa is Y, I, P, L, Q, S, R, T, F or A
<220> FEATURE:
<221> NAME/KEY: MISC_FEATURE
<222> LOCATION: (6)..(6)
<223> OTHER INFORMATION: Xaa is A, W, V, Q, L, S, I, R or T

<400> SEQUENCE: 41

Xaa Xaa His Xaa Xaa Xaa
1               5

<210> SEQ ID NO 42
<211> LENGTH: 16
<212> TYPE: PRT
<213> ORGANISM: Artificial Sequence
<220> FEATURE:
<223> OTHER INFORMATION: CETP mimotope
<220> FEATURE:
<221> NAME/KEY: MISC_FEATURE
<222> LOCATION: (2)..(2)
<223> OTHER INFORMATION: Xaa is selected from the group consisting of
      G, A, F, Y and K
<220> FEATURE:
<221> NAME/KEY: MISC_FEATURE
<222> LOCATION: (3)..(3)
<223> OTHER INFORMATION: F is (F)o, wherein o is 0 or 1
<220> FEATURE:
<221> NAME/KEY: MISC_FEATURE
<222> LOCATION: (5)..(5)
<223> OTHER INFORMATION: Xaa is selected from the group consisting of
      E, Y, A, Q, K and S
<220> FEATURE:
<221> NAME/KEY: MISC_FEATURE
<222> LOCATION: (7)..(7)
<223> OTHER INFORMATION: Xaa is selected from the group consisting of
      H, V, L, F and I
<220> FEATURE:
<221> NAME/KEY: MISC_FEATURE
<222> LOCATION: (8)..(8)
<223> OTHER INFORMATION: Xaa is selected from the group consisting of
      L, W, S, I, F and Y
<220> FEATURE:
<221> NAME/KEY: MISC_FEATURE
<222> LOCATION: (9)..(9)
<223> OTHER INFORMATION: Xaa is V, T, F or I
<220> FEATURE:
<221> NAME/KEY: MISC_FEATURE
```

```
<222> LOCATION: (11)..(11)
<223> OTHER INFORMATION: Xaa is an amino acid residue selected from the
      group consisting of F, A, W, R, S, L, Q, V and M
<220> FEATURE:
<221> NAME/KEY: MISC_FEATURE
<222> LOCATION: (12)..(12)
<223> OTHER INFORMATION: Xaa is an amino acid residue selected from the
      group consisting of L, A, S, W, E, R, I and H
<220> FEATURE:
<221> NAME/KEY: MISC_FEATURE
<222> LOCATION: (13)..(13)
<223> OTHER INFORMATION: Xaa is an amino acid residue selected from the
      group consisting of Q, A, H, D, K, R, S and E
<220> FEATURE:
<221> NAME/KEY: MISC_FEATURE
<222> LOCATION: (14)..(14)
<223> OTHER INFORMATION: Xaa is S or Y
<220> FEATURE:
<221> NAME/KEY: MISC_FEATURE
<222> LOCATION: (15)..(15)
<223> OTHER INFORMATION: Xaa is L, A or I
<220> FEATURE:
<221> NAME/KEY: MISC_FEATURE
<222> LOCATION: (16)..(16)
<223> OTHER INFORMATION: Xaa is S, N or T

<400> SEQUENCE: 42

Phe Xaa Phe Pro Xaa His Xaa Xaa Xaa Asp Xaa Xaa Xaa Xaa Xaa Xaa
1               5                   10                  15

<210> SEQ ID NO 43
<211> LENGTH: 7
<212> TYPE: PRT
<213> ORGANISM: Artificial Sequence
<220> FEATURE:
<223> OTHER INFORMATION: CETP mimotope
<220> FEATURE:
<221> NAME/KEY: MISC_FEATURE
<222> LOCATION: (1)..(1)
<223> OTHER INFORMATION: Xaa is selected from the group consisting of
      D, S, N, T and G
<220> FEATURE:
<221> NAME/KEY: MISC_FEATURE
<222> LOCATION: (4)..(4)
<223> OTHER INFORMATION: Xaa is selected from the group consisting of
      Q, D, K, R, S and E
<220> FEATURE:
<221> NAME/KEY: MISC_FEATURE
<222> LOCATION: (5)..(5)
<223> OTHER INFORMATION: Xaa is S or T
<220> FEATURE:
<221> NAME/KEY: MISC_FEATURE
<222> LOCATION: (7)..(7)
<223> OTHER INFORMATION: Xaa is an amino acid residue other than C,
      preferably selected from the group consisting of S, T, A, M, F
      and W

<400> SEQUENCE: 43

Xaa Phe Leu Xaa Xaa Leu Xaa
1               5

<210> SEQ ID NO 44
<211> LENGTH: 7
<212> TYPE: PRT
<213> ORGANISM: Artificial Sequence
<220> FEATURE:
<223> OTHER INFORMATION: CETP mimotope

<400> SEQUENCE: 44

Ser Ser Leu Glu Leu Phe Leu
1               5

<210> SEQ ID NO 45
<211> LENGTH: 7
```

```
<212> TYPE: PRT
<213> ORGANISM: Artificial Sequence
<220> FEATURE:
<223> OTHER INFORMATION: CETP mimotope

<400> SEQUENCE: 45

Ser Phe Leu Asp Thr Leu Thr
1               5

<210> SEQ ID NO 46
<211> LENGTH: 7
<212> TYPE: PRT
<213> ORGANISM: Artificial Sequence
<220> FEATURE:
<223> OTHER INFORMATION: CETP mimotope

<400> SEQUENCE: 46

Asn Phe Leu Lys Thr Leu Ser
1               5

<210> SEQ ID NO 47
<211> LENGTH: 7
<212> TYPE: PRT
<213> ORGANISM: Artificial Sequence
<220> FEATURE:
<223> OTHER INFORMATION: CETP mimotope

<400> SEQUENCE: 47

Asp Phe Leu Arg Thr Leu Thr
1               5

<210> SEQ ID NO 48
<211> LENGTH: 7
<212> TYPE: PRT
<213> ORGANISM: Artificial Sequence
<220> FEATURE:
<223> OTHER INFORMATION: CETP mimotope

<400> SEQUENCE: 48

Ala Phe Leu Asp Thr Leu Val
1               5

<210> SEQ ID NO 49
<211> LENGTH: 7
<212> TYPE: PRT
<213> ORGANISM: Artificial Sequence
<220> FEATURE:
<223> OTHER INFORMATION: CETP mimotope

<400> SEQUENCE: 49

Thr Phe Leu Ser Ser Leu Ala
1               5

<210> SEQ ID NO 50
<211> LENGTH: 7
<212> TYPE: PRT
<213> ORGANISM: Artificial Sequence
<220> FEATURE:
<223> OTHER INFORMATION: CETP mimotope

<400> SEQUENCE: 50

Gly Phe Leu Asp Ser Leu Met
1               5

<210> SEQ ID NO 51
<211> LENGTH: 7
<212> TYPE: PRT
<213> ORGANISM: Artificial Sequence
```

```
<220> FEATURE:
<223> OTHER INFORMATION: CETP mimotope

<400> SEQUENCE: 51

Ser Pro His Pro His Phe Leu
1               5

<210> SEQ ID NO 52
<211> LENGTH: 7
<212> TYPE: PRT
<213> ORGANISM: Artificial Sequence
<220> FEATURE:
<223> OTHER INFORMATION: CETP mimotope

<400> SEQUENCE: 52

Ser Asn Phe Leu Lys Thr Leu
1               5

<210> SEQ ID NO 53
<211> LENGTH: 7
<212> TYPE: PRT
<213> ORGANISM: Artificial Sequence
<220> FEATURE:
<223> OTHER INFORMATION: CETP mimotope

<400> SEQUENCE: 53

Thr Gly Phe Leu Ala Thr Leu
1               5

<210> SEQ ID NO 54
<211> LENGTH: 7
<212> TYPE: PRT
<213> ORGANISM: Artificial Sequence
<220> FEATURE:
<223> OTHER INFORMATION: CETP mimotope

<400> SEQUENCE: 54

Ser Asp Phe Leu Arg Ala Leu
1               5

<210> SEQ ID NO 55
<211> LENGTH: 12
<212> TYPE: PRT
<213> ORGANISM: Artificial Sequence
<220> FEATURE:
<223> OTHER INFORMATION: CETP mimotope

<400> SEQUENCE: 55

Ser Ala Asn Pro Arg Asp Phe Leu Glu Thr Leu Phe
1               5                   10

<210> SEQ ID NO 56
<211> LENGTH: 12
<212> TYPE: PRT
<213> ORGANISM: Artificial Sequence
<220> FEATURE:
<223> OTHER INFORMATION: CETP mimotope

<400> SEQUENCE: 56

Arg Met Phe Pro Glu Ser Phe Leu Asp Thr Leu Trp
1               5                   10

<210> SEQ ID NO 57
<211> LENGTH: 12
<212> TYPE: PRT
<213> ORGANISM: Artificial Sequence
<220> FEATURE:
<223> OTHER INFORMATION: CETP mimotope
```

```
<400> SEQUENCE: 57

Thr Ile Tyr Asp Ser Phe Leu Asp Ser Leu Ala Ser
1               5                   10

<210> SEQ ID NO 58
<211> LENGTH: 12
<212> TYPE: PRT
<213> ORGANISM: Artificial Sequence
<220> FEATURE:
<223> OTHER INFORMATION: CETP mimotope

<400> SEQUENCE: 58

Lys Pro Tyr Leu Leu Lys Asp Phe Leu Glu Ala Leu
1               5                   10

<210> SEQ ID NO 59
<211> LENGTH: 12
<212> TYPE: PRT
<213> ORGANISM: Artificial Sequence
<220> FEATURE:
<223> OTHER INFORMATION: CETP mimotope

<400> SEQUENCE: 59

Ala Met Gly Pro Tyr Asp Ala Leu Asp Leu Phe Leu
1               5                   10

<210> SEQ ID NO 60
<211> LENGTH: 12
<212> TYPE: PRT
<213> ORGANISM: Artificial Sequence
<220> FEATURE:
<223> OTHER INFORMATION: CETP mimotope

<400> SEQUENCE: 60

Thr Trp Asn Pro Ile Glu Ser Phe Leu Glu Ser Leu
1               5                   10

<210> SEQ ID NO 61
<211> LENGTH: 12
<212> TYPE: PRT
<213> ORGANISM: Artificial Sequence
<220> FEATURE:
<223> OTHER INFORMATION: CETP mimotope

<400> SEQUENCE: 61

Gln Tyr Gln Thr Pro Leu Thr Phe Leu Glu Ala Leu
1               5                   10

<210> SEQ ID NO 62
<211> LENGTH: 12
<212> TYPE: PRT
<213> ORGANISM: Artificial Sequence
<220> FEATURE:
<223> OTHER INFORMATION: CETP mimotope

<400> SEQUENCE: 62

Arg His Ile Ser Pro Ala Thr Phe Leu Glu Ala Leu
1               5                   10

<210> SEQ ID NO 63
<211> LENGTH: 12
<212> TYPE: PRT
<213> ORGANISM: Artificial Sequence
<220> FEATURE:
<223> OTHER INFORMATION: CETP mimotope

<400> SEQUENCE: 63
```

```
His Thr Asp Ser Phe Leu Ser Thr Phe Tyr Gly Asp
1               5                   10
```

<210> SEQ ID NO 64
<211> LENGTH: 12
<212> TYPE: PRT
<213> ORGANISM: Artificial Sequence
<220> FEATURE:
<223> OTHER INFORMATION: CETP mimotope

<400> SEQUENCE: 64

```
Ala Asp Ser Thr Phe Thr Ser Phe Leu Gln Thr Leu
1               5                   10
```

<210> SEQ ID NO 65
<211> LENGTH: 12
<212> TYPE: PRT
<213> ORGANISM: Artificial Sequence
<220> FEATURE:
<223> OTHER INFORMATION: CETP mimotope

<400> SEQUENCE: 65

```
Gly Pro Val Ser Ile Tyr Ala Asp Thr Asp Phe Leu
1               5                   10
```

<210> SEQ ID NO 66
<211> LENGTH: 12
<212> TYPE: PRT
<213> ORGANISM: Artificial Sequence
<220> FEATURE:
<223> OTHER INFORMATION: CETP mimotope

<400> SEQUENCE: 66

```
Asp Ser Asn Asp Thr Leu Thr Leu Ala Ala Phe Leu
1               5                   10
```

<210> SEQ ID NO 67
<211> LENGTH: 12
<212> TYPE: PRT
<213> ORGANISM: Artificial Sequence
<220> FEATURE:
<223> OTHER INFORMATION: CETP mimotope

<400> SEQUENCE: 67

```
Thr Pro Thr His Tyr Tyr Ala Asp Phe Ser Gln Leu
1               5                   10
```

<210> SEQ ID NO 68
<211> LENGTH: 12
<212> TYPE: PRT
<213> ORGANISM: Artificial Sequence
<220> FEATURE:
<223> OTHER INFORMATION: CETP mimotope

<400> SEQUENCE: 68

```
Leu Pro Gly His Leu Ile Trp Asp Ser Leu His Tyr
1               5                   10
```

<210> SEQ ID NO 69
<211> LENGTH: 12
<212> TYPE: PRT
<213> ORGANISM: Artificial Sequence
<220> FEATURE:
<223> OTHER INFORMATION: CETP mimotope

<400> SEQUENCE: 69

```
Leu Pro Gln Thr His Pro Leu His Leu Leu Glu Asp
```

```
<210> SEQ ID NO 70
<211> LENGTH: 12
<212> TYPE: PRT
<213> ORGANISM: Artificial Sequence
<220> FEATURE:
<223> OTHER INFORMATION: CETP mimotope

<400> SEQUENCE: 70

Ile Pro Tyr His His Leu Val Asp Gln Leu His His
1               5                   10

<210> SEQ ID NO 71
<211> LENGTH: 12
<212> TYPE: PRT
<213> ORGANISM: Artificial Sequence
<220> FEATURE:
<223> OTHER INFORMATION: CETP mimotope

<400> SEQUENCE: 71

Tyr Pro Tyr His Val Gln Val Asp Val Leu Gln Asn
1               5                   10

<210> SEQ ID NO 72
<211> LENGTH: 12
<212> TYPE: PRT
<213> ORGANISM: Artificial Sequence
<220> FEATURE:
<223> OTHER INFORMATION: CETP mimotope

<400> SEQUENCE: 72

Ile Pro Ser His His Leu Gln Asp Ser Leu Gln Leu
1               5                   10

<210> SEQ ID NO 73
<211> LENGTH: 12
<212> TYPE: PRT
<213> ORGANISM: Artificial Sequence
<220> FEATURE:
<223> OTHER INFORMATION: CETP mimotope

<400> SEQUENCE: 73

Glu Tyr Ala His His Thr Ser Leu Asp Leu Arg Gln
1               5                   10

<210> SEQ ID NO 74
<211> LENGTH: 12
<212> TYPE: PRT
<213> ORGANISM: Artificial Sequence
<220> FEATURE:
<223> OTHER INFORMATION: CETP mimotope

<400> SEQUENCE: 74

Glu Pro Leu His Phe Arg Ser Asp Arg Ile Gln Ala
1               5                   10

<210> SEQ ID NO 75
<211> LENGTH: 12
<212> TYPE: PRT
<213> ORGANISM: Artificial Sequence
<220> FEATURE:
<223> OTHER INFORMATION: CETP mimotope

<400> SEQUENCE: 75

Ala Thr Pro Ser His Leu Ile Ile Asp Arg Ala Gln
1               5                   10
```

```
<210> SEQ ID NO 76
<211> LENGTH: 12
<212> TYPE: PRT
<213> ORGANISM: Artificial Sequence
<220> FEATURE:
<223> OTHER INFORMATION: CETP mimotope

<400> SEQUENCE: 76

Ala Pro Lys His Leu Tyr Ala Asp Met Ser Gln Ala
1               5                   10

<210> SEQ ID NO 77
<211> LENGTH: 12
<212> TYPE: PRT
<213> ORGANISM: Artificial Sequence
<220> FEATURE:
<223> OTHER INFORMATION: CETP mimotope

<400> SEQUENCE: 77

Phe Lys Pro Ala His Val Ser Ile Asp Trp Leu Gln
1               5                   10

<210> SEQ ID NO 78
<211> LENGTH: 12
<212> TYPE: PRT
<213> ORGANISM: Artificial Sequence
<220> FEATURE:
<223> OTHER INFORMATION: CETP mimotope

<400> SEQUENCE: 78

Met Pro Ala His Leu Ser Arg Asp Leu Arg Gln Ser
1               5                   10

<210> SEQ ID NO 79
<211> LENGTH: 12
<212> TYPE: PRT
<213> ORGANISM: Artificial Sequence
<220> FEATURE:
<223> OTHER INFORMATION: CETP mimotope

<400> SEQUENCE: 79

Asn Pro Lys His Tyr Ser Ile Asp Arg His Gln Ala
1               5                   10

<210> SEQ ID NO 80
<211> LENGTH: 12
<212> TYPE: PRT
<213> ORGANISM: Artificial Sequence
<220> FEATURE:
<223> OTHER INFORMATION: CETP mimotope

<400> SEQUENCE: 80

Ser Pro Gln His Leu Thr Thr Asp Arg Ala Gln Ala
1               5                   10

<210> SEQ ID NO 81
<211> LENGTH: 12
<212> TYPE: PRT
<213> ORGANISM: Artificial Sequence
<220> FEATURE:
<223> OTHER INFORMATION: CETP mimotope

<400> SEQUENCE: 81

Thr Pro Phe His Phe Ala Gln Asp Ser Trp Gln Trp
1               5                   10

<210> SEQ ID NO 82
```

```
<211> LENGTH: 14
<212> TYPE: PRT
<213> ORGANISM: Artificial Sequence
<220> FEATURE:
<223> OTHER INFORMATION: CETP mimotope

<400> SEQUENCE: 82

Thr Pro Thr His Tyr Tyr Ala Asp Phe Ser Gln Leu Leu Ser
1               5                   10

<210> SEQ ID NO 83
<211> LENGTH: 14
<212> TYPE: PRT
<213> ORGANISM: Artificial Sequence
<220> FEATURE:
<223> OTHER INFORMATION: CETP mimotope

<400> SEQUENCE: 83

Thr Pro Thr His Tyr Tyr Ala Asp Phe Ser Gln Ser Leu Ser
1               5                   10

<210> SEQ ID NO 84
<211> LENGTH: 14
<212> TYPE: PRT
<213> ORGANISM: Artificial Sequence
<220> FEATURE:
<223> OTHER INFORMATION: CETP mimotope

<400> SEQUENCE: 84

Gly Thr Pro Thr His Tyr Tyr Ala Asp Phe Ser Gln Leu Leu
1               5                   10

<210> SEQ ID NO 85
<211> LENGTH: 14
<212> TYPE: PRT
<213> ORGANISM: Artificial Sequence
<220> FEATURE:
<223> OTHER INFORMATION: CETP mimotope

<400> SEQUENCE: 85

Gly Thr Pro Thr His Tyr Tyr Ala Asp Phe Ser Gln Ser Leu
1               5                   10

<210> SEQ ID NO 86
<211> LENGTH: 16
<212> TYPE: PRT
<213> ORGANISM: Artificial Sequence
<220> FEATURE:
<223> OTHER INFORMATION: CETP mimotope

<400> SEQUENCE: 86

Phe Gly Thr Pro Thr His Tyr Tyr Ala Asp Phe Ser Gln Ser Leu Ser
1               5                   10                  15

<210> SEQ ID NO 87
<211> LENGTH: 16
<212> TYPE: PRT
<213> ORGANISM: Artificial Sequence
<220> FEATURE:
<223> OTHER INFORMATION: CETP mimotope

<400> SEQUENCE: 87

Phe Gly Phe Pro Thr His Tyr Tyr Ala Asp Phe Ser Gln Ser Leu Ser
1               5                   10                  15

<210> SEQ ID NO 88
<211> LENGTH: 12
<212> TYPE: PRT
```

-continued

```
<213> ORGANISM: Artificial Sequence
<220> FEATURE:
<223> OTHER INFORMATION: CETP mimotope

<400> SEQUENCE: 88

Leu Pro Gly His Leu Ile Trp Asp Ser Leu His Tyr
1               5                   10

<210> SEQ ID NO 89
<211> LENGTH: 13
<212> TYPE: PRT
<213> ORGANISM: Artificial Sequence
<220> FEATURE:
<223> OTHER INFORMATION: CETP mimotope

<400> SEQUENCE: 89

Leu Pro Gly His Leu Ile Trp Asp Ser Leu His Tyr Leu
1               5                   10

<210> SEQ ID NO 90
<211> LENGTH: 14
<212> TYPE: PRT
<213> ORGANISM: Artificial Sequence
<220> FEATURE:
<223> OTHER INFORMATION: CETP mimotope

<400> SEQUENCE: 90

Leu Pro Gly His Leu Ile Trp Asp Ser Leu His Tyr Leu Ser
1               5                   10

<210> SEQ ID NO 91
<211> LENGTH: 13
<212> TYPE: PRT
<213> ORGANISM: Artificial Sequence
<220> FEATURE:
<223> OTHER INFORMATION: CETP mimotope

<400> SEQUENCE: 91

Leu Pro Gly His Leu Ile Trp Asp Ser Leu His Ser Leu
1               5                   10

<210> SEQ ID NO 92
<211> LENGTH: 14
<212> TYPE: PRT
<213> ORGANISM: Artificial Sequence
<220> FEATURE:
<223> OTHER INFORMATION: CETP mimotope

<400> SEQUENCE: 92

Leu Pro Gly His Leu Ile Trp Asp Ser Leu His Ser Leu Ser
1               5                   10

<210> SEQ ID NO 93
<211> LENGTH: 14
<212> TYPE: PRT
<213> ORGANISM: Artificial Sequence
<220> FEATURE:
<223> OTHER INFORMATION: CETP mimotope

<400> SEQUENCE: 93

Gly Leu Pro Gly His Leu Ile Trp Asp Ser Leu His Tyr Leu
1               5                   10

<210> SEQ ID NO 94
<211> LENGTH: 14
<212> TYPE: PRT
<213> ORGANISM: Artificial Sequence
<220> FEATURE:
```

<223> OTHER INFORMATION: CETP mimotope

<400> SEQUENCE: 94

Gly Leu Pro Gly His Leu Ile Tr

```
<400> SEQUENCE: 100

Ile Pro Tyr His His Leu Val Asp Gln Leu His Ser Leu Ser
1               5                   10

<210> SEQ ID NO 101
<211> LENGTH: 16
<212> TYPE: PRT
<213> ORGANISM: Artificial Sequence
<220> FEATURE:
<223> OTHER INFORMATION: CETP mimotope

<400> SEQUENCE: 101

Phe Gly Ile Pro Tyr His His Leu Val Asp Gln Leu His His Leu Ser
1               5                   10                  15

<210> SEQ ID NO 102
<211> LENGTH: 16
<212> TYPE: PRT
<213> ORGANISM: Artificial Sequence
<220> FEATURE:
<223> OTHER INFORMATION: CETP mimotope

<400> SEQUENCE: 102

Phe Gly Phe Pro Tyr His His Leu Val Asp Gln Leu His Ser Leu Ser
1               5                   10                  15

<210> SEQ ID NO 103
<211> LENGTH: 12
<212> TYPE: PRT
<213> ORGANISM: Artificial Sequence
<220> FEATURE:
<223> OTHER INFORMATION: CETP mimotope

<400> SEQUENCE: 103

Tyr Pro Tyr His Val Gln Val Asp Val Leu Gln Asn
1               5                   10

<210> SEQ ID NO 104
<211> LENGTH: 14
<212> TYPE: PRT
<213> ORGANISM: Artificial Sequence
<220> FEATURE:
<223> OTHER INFORMATION: CETP mimotope

<400> SEQUENCE: 104

Tyr Pro Tyr His Val Gln Val Asp Val Leu Gln Asn Leu Ser
1               5                   10

<210> SEQ ID NO 105
<211> LENGTH: 14
<212> TYPE: PRT
<213> ORGANISM: Artificial Sequence
<220> FEATURE:
<223> OTHER INFORMATION: CETP mimotope

<400> SEQUENCE: 105

Tyr Pro Tyr His Val Gln Val Asp Val Leu Gln Ser Leu Ser
1               5                   10

<210> SEQ ID NO 106
<211> LENGTH: 16
<212> TYPE: PRT
<213> ORGANISM: Artificial Sequence
<220> FEATURE:
<223> OTHER INFORMATION: CETP mimotope

<400> SEQUENCE: 106
```

Phe Gly Tyr Pro Tyr His Val Gln Val Asp Val Leu Gln Asn Leu Ser
1               5                   10                  15

<210> SEQ ID NO 107
<211> LENGTH: 16
<212> TYPE: PRT
<213> ORGANISM: Artificial Sequence
<220> FEATURE:
<223> OTHER INFORMATION: CETP mimotope

<400> SEQUENCE: 107

Phe Gly Phe Pro Tyr His Val Gln Val Asp Val Leu Gln Ser Leu Ser
1               5                   10                  15

<210> SEQ ID NO 108
<211> LENGTH: 12
<212> TYPE: PRT
<213> ORGANISM: Artificial Sequence
<220> FEATURE:
<223> OTHER INFORMATION: CETP mimotope

<400> SEQUENCE: 108

Ile Pro Ser His His Leu Gln Asp Ser Leu Gln Leu
1               5                   10

<210> SEQ ID NO 109
<211> LENGTH: 14
<212> TYPE: PRT
<213> ORGANISM: Artificial Sequence
<220> FEATURE:
<223> OTHER INFORMATION: CETP mimotope

<400> SEQUENCE: 109

Ile Pro Ser His His Leu Gln Asp Ser Leu Gln Leu Leu Ser
1               5                   10

<210> SEQ ID NO 110
<211> LENGTH: 14
<212> TYPE: PRT
<213> ORGANISM: Artificial Sequence
<220> FEATURE:
<223> OTHER INFORMATION: CETP mimotope

<400> SEQUENCE: 110

Ile Pro Ser His His Leu Gln Asp Ser Leu Gln Ser Leu Ser
1               5                   10

<210> SEQ ID NO 111
<211> LENGTH: 14
<212> TYPE: PRT
<213> ORGANISM: Artificial Sequence
<220> FEATURE:
<223> OTHER INFORMATION: CETP mimotope

<400> SEQUENCE: 111

Gly Ile Pro Ser His His Leu Gln Asp Ser Leu Gln Leu Leu
1               5                   10

<210> SEQ ID NO 112
<211> LENGTH: 16
<212> TYPE: PRT
<213> ORGANISM: Artificial Sequence
<220> FEATURE:
<223> OTHER INFORMATION: CETP mimotope

<400> SEQUENCE: 112

Phe Gly Ile Pro Ser His His Leu Gln Asp Ser Leu Gln Leu Leu Ser
1               5                   10                  15

```
<210> SEQ ID NO 113
<211> LENGTH: 16
<212> TYPE: PRT
<213> ORGANISM: Artificial Sequence
<220> FEATURE:
<223> OTHER INFORMATION: CETP mimotope

<400> SEQUENCE: 113

Phe Gly Phe Pro Ser His His Leu Gln Asp Ser Leu Gln Ser Leu Ser
1               5                   10                  15

<210> SEQ ID NO 114
<211> LENGTH: 12
<212> TYPE: PRT
<213> ORGANISM: Artificial Sequence
<220> FEATURE:
<223> OTHER INFORMATION: CETP mimotope

<400> SEQUENCE: 114

Glu Tyr Ala His His Thr Ser Leu Asp Leu Arg Gln
1               5                   10

<210> SEQ ID NO 115
<211> LENGTH: 12
<212> TYPE: PRT
<213> ORGANISM: Artificial Sequence
<220> FEATURE:
<223> OTHER INFORMATION: CETP mimotope

<400> SEQUENCE: 115

Glu Pro Leu His Phe Arg Ser Asp Arg Ile Gln Ala
1               5                   10

<210> SEQ ID NO 116
<211> LENGTH: 14
<212> TYPE: PRT
<213> ORGANISM: Artificial Sequence
<220> FEATURE:
<223> OTHER INFORMATION: CETP mimotope

<400> SEQUENCE: 116

Glu Pro Leu His Phe Arg Ser Asp Arg Ile Gln Ala Leu Ser
1               5                   10

<210> SEQ ID NO 117
<211> LENGTH: 14
<212> TYPE: PRT
<213> ORGANISM: Artificial Sequence
<220> FEATURE:
<223> OTHER INFORMATION: CETP mimotope

<400> SEQUENCE: 117

Glu Pro Leu His Phe Arg Ser Asp Arg Ile Gln Ser Leu Ser
1               5                   10

<210> SEQ ID NO 118
<211> LENGTH: 14
<212> TYPE: PRT
<213> ORGANISM: Artificial Sequence
<220> FEATURE:
<223> OTHER INFORMATION: CETP mimotope

<400> SEQUENCE: 118

Gly Glu Pro Leu His Phe Arg Ser Asp Arg Ile Gln Ala Leu
1               5                   10
```

```
<210> SEQ ID NO 119
<211> LENGTH: 16
<212> TYPE: PRT
<213> ORGANISM: Artificial Sequence
<220> FEATURE:
<223> OTHER INFORMATION: CETP mimotope

<400> SEQUENCE: 119

Phe Gly Glu Pro Leu His Phe Arg Ser Asp Arg Ile Gln Ala Leu Ser
1               5                   10                  15

<210> SEQ ID NO 120
<211> LENGTH: 16
<212> TYPE: PRT
<213> ORGANISM: Artificial Sequence
<220> FEATURE:
<223> OTHER INFORMATION: CETP mimotope

<400> SEQUENCE: 120

Phe Gly Phe Pro Leu His Phe Arg Ser Asp Arg Ile Gln Ser Leu Ser
1               5                   10                  15

<210> SEQ ID NO 121
<211> LENGTH: 12
<212> TYPE: PRT
<213> ORGANISM: Artificial Sequence
<220> FEATURE:
<223> OTHER INFORMATION: CETP mimotope

<400> SEQUENCE: 121

Ala Pro Lys His Leu Tyr Ala Asp Met Ser Gln Ala
1               5                   10

<210> SEQ ID NO 122
<211> LENGTH: 14
<212> TYPE: PRT
<213> ORGANISM: Artificial Sequence
<220> FEATURE:
<223> OTHER INFORMATION: CETP mimotope

<400> SEQUENCE: 122

Ala Pro Lys His Leu Tyr Ala Asp Met Ser Gln Ala Leu Ser
1               5                   10

<210> SEQ ID NO 123
<211> LENGTH: 14
<212> TYPE: PRT
<213> ORGANISM: Artificial Sequence
<220> FEATURE:
<223> OTHER INFORMATION: CETP mimotope

<400> SEQUENCE: 123

Ala Pro Lys His Leu Tyr Ala Asp Met Ser Gln Ser Leu Ser
1               5                   10

<210> SEQ ID NO 124
<211> LENGTH: 14
<212> TYPE: PRT
<213> ORGANISM: Artificial Sequence
<220> FEATURE:
<223> OTHER INFORMATION: CETP mimotope

<400> SEQUENCE: 124

Gly Ala Pro Lys His Leu Tyr Ala Asp Met Ser Gln Ala Leu
1               5                   10

<210> SEQ ID NO 125
<211> LENGTH: 16
```

```
<212> TYPE: PRT
<213> ORGANISM: Artificial Sequence
<220> FEATURE:
<223> OTHER INFORMATION: CETP mimotope

<400> SEQUENCE: 125

Phe Gly Phe Pro Lys His Leu Tyr Ala Asp Met Ser Gln Ser Leu Ser
1               5                   10                  15

<210> SEQ ID NO 126
<211> LENGTH: 12
<212> TYPE: PRT
<213> ORGANISM: Artificial Sequence
<220> FEATURE:
<223> OTHER INFORMATION: CETP mimotope

<400> SEQUENCE: 126

Met Pro Ala His Leu Ser Arg Asp Leu Arg Gln Ser
1               5                   10

<210> SEQ ID NO 127
<211> LENGTH: 13
<212> TYPE: PRT
<213> ORGANISM: Artificial Sequence
<220> FEATURE:
<223> OTHER INFORMATION: CETP mimotope

<400> SEQUENCE: 127

Met Pro Ala His Leu Ser Arg Asp Leu Arg Gln Ser Leu
1               5                   10

<210> SEQ ID NO 128
<211> LENGTH: 14
<212> TYPE: PRT
<213> ORGANISM: Artificial Sequence
<220> FEATURE:
<223> OTHER INFORMATION: CETP mimotope

<400> SEQUENCE: 128

Met Pro Ala His Leu Ser Arg Asp Leu Arg Gln Ser Leu Ser
1               5                   10

<210> SEQ ID NO 129
<211> LENGTH: 14
<212> TYPE: PRT
<213> ORGANISM: Artificial Sequence
<220> FEATURE:
<223> OTHER INFORMATION: CETP mimotope

<400> SEQUENCE: 129

Gly Met Pro Ala His Leu Ser Arg Asp Leu Arg Gln Ser Leu
1               5                   10

<210> SEQ ID NO 130
<211> LENGTH: 16
<212> TYPE: PRT
<213> ORGANISM: Artificial Sequence
<220> FEATURE:
<223> OTHER INFORMATION: CETP mimotope

<400> SEQUENCE: 130

Phe Gly Phe Pro Ala His Leu Ser Arg Asp Leu Arg Gln Ser Leu Ser
1               5                   10                  15

<210> SEQ ID NO 131
<211> LENGTH: 12
<212> TYPE: PRT
<213> ORGANISM: Artificial Sequence
```

```
<220> FEATURE:
<223> OTHER INFORMATION: CETP mimotope

<400> SEQUENCE: 131

Asn Pro Lys His Tyr Ser Ile Asp Arg His Gln Ala
1               5                   10

<210> SEQ ID NO 132
<211> LENGTH: 12
<212> TYPE: PRT
<213> ORGANISM: Artificial Sequence
<220> FEATURE:
<223> OTHER INFORMATION: CETP mimotope

<400> SEQUENCE: 132

Thr Pro Phe His Phe Ala Gln Asp Ser Trp Gln Trp
1               5                   10

<210> SEQ ID NO 133
<211> LENGTH: 14
<212> TYPE: PRT
<213> ORGANISM: Artificial Sequence
<220> FEATURE:
<223> OTHER INFORMATION: CETP mimotope

<400> SEQUENCE: 133

Thr Pro Phe His Phe Ala Gln Asp Ser Trp Gln Trp Leu Ser
1               5                   10

<210> SEQ ID NO 134
<211> LENGTH: 14
<212> TYPE: PRT
<213> ORGANISM: Artificial Sequence
<220> FEATURE:
<223> OTHER INFORMATION: CETP mimotope

<400> SEQUENCE: 134

Thr Pro Phe His Phe Ala Gln Asp Ser Trp Gln Ser Leu Ser
1               5                   10

<210> SEQ ID NO 135
<211> LENGTH: 14
<212> TYPE: PRT
<213> ORGANISM: Artificial Sequence
<220> FEATURE:
<223> OTHER INFORMATION: CETP mimotope

<400> SEQUENCE: 135

Gly Thr Pro Phe His Phe Ala Gln Asp Ser Trp Gln Trp Leu
1               5                   10

<210> SEQ ID NO 136
<211> LENGTH: 16
<212> TYPE: PRT
<213> ORGANISM: Artificial Sequence
<220> FEATURE:
<223> OTHER INFORMATION: CETP mimotope

<400> SEQUENCE: 136

Phe Gly Phe Pro Phe His Phe Ala Gln Asp Ser Trp Gln Ser Leu Ser
1               5                   10                  15

<210> SEQ ID NO 137
<211> LENGTH: 10
<212> TYPE: PRT
<213> ORGANISM: Artificial Sequence
<220> FEATURE:
<223> OTHER INFORMATION: CETP mimotope
```

```
<400> SEQUENCE: 137

Ala Cys Ser Phe Ala Tyr Leu Tyr Arg Cys
1               5                   10

<210> SEQ ID NO 138
<211> LENGTH: 10
<212> TYPE: PRT
<213> ORGANISM: Artificial Sequence
<220> FEATURE:
<223> OTHER INFORMATION: CETP mimotope

<400> SEQUENCE: 138

Ala Cys Phe Met Gly Asp Lys Trp Val Cys
1               5                   10

<210> SEQ ID NO 139
<211> LENGTH: 10
<212> TYPE: PRT
<213> ORGANISM: Artificial Sequence
<220> FEATURE:
<223> OTHER INFORMATION: CETP mimotope

<400> SEQUENCE: 139

Ala Cys Val Leu Tyr Pro Lys Ala Ile Cys
1               5                   10

<210> SEQ ID NO 140
<211> LENGTH: 10
<212> TYPE: PRT
<213> ORGANISM: Artificial Sequence
<220> FEATURE:
<223> OTHER INFORMATION: CETP mimotope

<400> SEQUENCE: 140

Ala Cys Tyr Met Gly Gln Gln Phe Val Cys
1               5                   10

<210> SEQ ID NO 141
<211> LENGTH: 10
<212> TYPE: PRT
<213> ORGANISM: Artificial Sequence
<220> FEATURE:
<223> OTHER INFORMATION: CETP mimotope

<400> SEQUENCE: 141

Ala Cys Leu Thr Ala Tyr Leu His Trp Cys
1               5                   10

<210> SEQ ID NO 142
<211> LENGTH: 10
<212> TYPE: PRT
<213> ORGANISM: Artificial Sequence
<220> FEATURE:
<223> OTHER INFORMATION: CETP mimotope

<400> SEQUENCE: 142

Ala Cys Thr Leu Phe Pro Val Ala Tyr Cys
1               5                   10

<210> SEQ ID NO 143
<211> LENGTH: 10
<212> TYPE: PRT
<213> ORGANISM: Artificial Sequence
<220> FEATURE:
<223> OTHER INFORMATION: CETP mimotope

<400> SEQUENCE: 143
```

```
Ala Cys Trp Leu Phe Pro Tyr Ala His Cys
1               5                   10

<210> SEQ ID NO 144
<211> LENGTH: 10
<212> TYPE: PRT
<213> ORGANISM: Artificial Sequence
<220> FEATURE:
<223> OTHER INFORMATION: CETP mimotope

<400> SEQUENCE: 144

Ala Cys Lys Ser Ile Asn Met Trp Leu Cys
1               5                   10

<210> SEQ ID NO 145
<211> LENGTH: 10
<212> TYPE: PRT
<213> ORGANISM: Artificial Sequence
<220> FEATURE:
<223> OTHER INFORMATION: CETP mimotope

<400> SEQUENCE: 145

Ala Cys Gln Thr Ile Asn Arg Trp Leu Cys
1               5                   10

<210> SEQ ID NO 146
<211> LENGTH: 16
<212> TYPE: PRT
<213> ORGANISM: Artificial Sequence
<220> FEATURE:
<223> OTHER INFORMATION: CETP mimotope

<400> SEQUENCE: 146

Phe Gly Phe Pro Glu His Leu Leu Val Asp Phe Leu Gln Ser Leu Ser
1               5                   10                  15

<210> SEQ ID NO 147
<211> LENGTH: 16
<212> TYPE: PRT
<213> ORGANISM: Artificial Sequence
<220> FEATURE:
<223> OTHER INFORMATION: CETP mimotope

<400> SEQUENCE: 147

Phe Gly Phe Pro Glu His Leu Leu Val Asp Phe Leu Gln Ser Leu Ser
1               5                   10                  15

<210> SEQ ID NO 148
<211> LENGTH: 13
<212> TYPE: PRT
<213> ORGANISM: Artificial Sequence
<220> FEATURE:
<223> OTHER INFORMATION: CETP mimotope

<400> SEQUENCE: 148

Phe Pro Glu His Leu Leu Val Asp Phe Leu Gln Ser Leu
1               5                   10

<210> SEQ ID NO 149
<211> LENGTH: 16
<212> TYPE: PRT
<213> ORGANISM: Artificial Sequence
<220> FEATURE:
<223> OTHER INFORMATION: CETP mimotope

<400> SEQUENCE: 149

Ala Gly Phe Pro Glu His Leu Leu Val Asp Phe Leu Gln Ser Leu Ser
```

```
1               5                   10                  15
```

<210> SEQ ID NO 150
<211> LENGTH: 16
<212> TYPE: PRT
<213> ORGANISM: Artificial Sequence
<220> FEATURE:
<223> OTHER INFORMATION: CETP mimotope

<400> SEQUENCE: 150

```
Phe Ala Phe Pro Glu His Leu Leu Val Asp Phe Leu Gln Ser Leu Ser
1               5                   10                  15
```

<210> SEQ ID NO 151
<211> LENGTH: 16
<212> TYPE: PRT
<213> ORGANISM: Artificial Sequence
<220> FEATURE:
<223> OTHER INFORMATION: CETP mimotope

<400> SEQUENCE: 151

```
Phe Gly Ala Pro Glu His Leu Leu Val Asp Phe Leu Gln Ser Leu Ser
1               5                   10                  15
```

<210> SEQ ID NO 152
<211> LENGTH: 16
<212> TYPE: PRT
<213> ORGANISM: Artificial Sequence
<220> FEATURE:
<223> OTHER INFORMATION: CETP mimotope

<400> SEQUENCE: 152

```
Phe Gly Phe Ala Glu His Leu Leu Val Asp Phe Leu Gln Ser Leu Ser
1               5                   10                  15
```

<210> SEQ ID NO 153
<211> LENGTH: 16
<212> TYPE: PRT
<213> ORGANISM: Artificial Sequence
<220> FEATURE:
<223> OTHER INFORMATION: CETP mimotope

<400> SEQUENCE: 153

```
Phe Gly Phe Pro Ala His Leu Leu Val Asp Phe Leu Gln Ser Leu Ser
1               5                   10                  15
```

<210> SEQ ID NO 154
<211> LENGTH: 16
<212> TYPE: PRT
<213> ORGANISM: Artificial Sequence
<220> FEATURE:
<223> OTHER INFORMATION: CETP mimotope

<400> SEQUENCE: 154

```
Phe Gly Phe Pro Glu Ala Leu Leu Val Asp Phe Leu Gln Ser Leu Ser
1               5                   10                  15
```

<210> SEQ ID NO 155
<211> LENGTH: 16
<212> TYPE: PRT
<213> ORGANISM: Artificial Sequence
<220> FEATURE:
<223> OTHER INFORMATION: CETP mimotope

<400> SEQUENCE: 155

```
Phe Gly Phe Pro Glu His Ala Leu Val Asp Phe Leu Gln Ser Leu Ser
1               5                   10                  15
```

```
<210> SEQ ID NO 156
<211> LENGTH: 16
<212> TYPE: PRT
<213> ORGANISM: Artificial Sequence
<220> FEATURE:
<223> OTHER INFORMATION: CETP mimotope

<400> SEQUENCE: 156

Phe Gly Phe Pro Glu His Leu Ala Val Asp Phe Leu Gln Ser Leu Ser
1               5                   10                  15

<210> SEQ ID NO 157
<211> LENGTH: 16
<212> TYPE: PRT
<213> ORGANISM: Artificial Sequence
<220> FEATURE:
<223> OTHER INFORMATION: CETP mimotope

<400> SEQUENCE: 157

Phe Gly Phe Pro Glu His Leu Leu Ala Asp Phe Leu Gln Ser Leu Ser
1               5                   10                  15

<210> SEQ ID NO 158
<211> LENGTH: 16
<212> TYPE: PRT
<213> ORGANISM: Artificial Sequence
<220> FEATURE:
<223> OTHER INFORMATION: CETP mimotope

<400> SEQUENCE: 158

Phe Gly Phe Pro Glu His Leu Leu Val Ala Phe Leu Gln Ser Leu Ser
1               5                   10                  15

<210> SEQ ID NO 159
<211> LENGTH: 16
<212> TYPE: PRT
<213> ORGANISM: Artificial Sequence
<220> FEATURE:
<223> OTHER INFORMATION: CETP mimotope

<400> SEQUENCE: 159

Phe Gly Phe Pro Glu His Leu Leu Val Asp Ala Leu Gln Ser Leu Ser
1               5                   10                  15

<210> SEQ ID NO 160
<211> LENGTH: 16
<212> TYPE: PRT
<213> ORGANISM: Artificial Sequence
<220> FEATURE:
<223> OTHER INFORMATION: CETP mimotope

<400> SEQUENCE: 160

Phe Gly Phe Pro Glu His Leu Leu Val Asp Phe Ala Gln Ser Leu Ser
1               5                   10                  15

<210> SEQ ID NO 161
<211> LENGTH: 16
<212> TYPE: PRT
<213> ORGANISM: Artificial Sequence
<220> FEATURE:
<223> OTHER INFORMATION: CETP mimotope

<400> SEQUENCE: 161

Phe Gly Phe Pro Glu His Leu Leu Val Asp Phe Leu Ala Ser Leu Ser
1               5                   10                  15

<210> SEQ ID NO 162
```

```
<211> LENGTH: 16
<212> TYPE: PRT
<213> ORGANISM: Artificial Sequence
<220> FEATURE:
<223> OTHER INFORMATION: CETP mimotope

<400> SEQUENCE: 162

Phe Gly Phe Pro Glu His Leu Leu Val Asp Phe Leu Gln Ala Leu Ser
1               5                   10                  15

<210> SEQ ID NO 163
<211> LENGTH: 16
<212> TYPE: PRT
<213> ORGANISM: Artificial Sequence
<220> FEATURE:
<223> OTHER INFORMATION: CETP mimotope

<400> SEQUENCE: 163

Phe Gly Phe Pro Glu His Leu Leu Val Asp Phe Leu Gln Ser Ala Ser
1               5                   10                  15

<210> SEQ ID NO 164
<211> LENGTH: 16
<212> TYPE: PRT
<213> ORGANISM: Artificial Sequence
<220> FEATURE:
<223> OTHER INFORMATION: CETP mimotope

<400> SEQUENCE: 164

Phe Gly Phe Pro Glu His Leu Leu Val Asp Phe Leu Gln Ser Leu Ala
1               5                   10                  15

<210> SEQ ID NO 165
<211> LENGTH: 16
<212> TYPE: PRT
<213> ORGANISM: Artificial Sequence
<220> FEATURE:
<223> OTHER INFORMATION: CETP mimotope

<400> SEQUENCE: 165

Phe Ala Phe Pro Ala His Leu Leu Val Asp Phe Leu Gln Ala Leu Ala
1               5                   10                  15

<210> SEQ ID NO 166
<211> LENGTH: 16
<212> TYPE: PRT
<213> ORGANISM: Artificial Sequence
<220> FEATURE:
<223> OTHER INFORMATION: CETP mimotope

<400> SEQUENCE: 166

Ala Ala Phe Pro Ala His Leu Leu Ala Asp Phe Leu Gln Ala Leu Ala
1               5                   10                  15

<210> SEQ ID NO 167
<211> LENGTH: 12
<212> TYPE: PRT
<213> ORGANISM: Artificial Sequence
<220> FEATURE:
<223> OTHER INFORMATION: CETP mimotope

<400> SEQUENCE: 167

Ser Pro Gln His Leu Thr Thr Asp Arg Ala Gln Ala
1               5                   10

<210> SEQ ID NO 168
<211> LENGTH: 14
<212> TYPE: PRT
```

```
<213> ORGANISM: Artificial Sequence
<220> FEATURE:
<223> OTHER INFORMATION: CETP mimotope

<400> SEQUENCE: 168

Ser Pro Gln His Leu Thr Thr Asp Arg Ala Gln Ala Leu Ser
1               5                   10

<210> SEQ ID NO 169
<211> LENGTH: 14
<212> TYPE: PRT
<213> ORGANISM: Artificial Sequence
<220> FEATURE:
<223> OTHER INFORMATION: CETP mimotope

<400> SEQUENCE: 169

Ser Pro Gln His Leu Thr Thr Asp Arg Ala Gln Ser Leu Ser
1               5                   10

<210> SEQ ID NO 170
<211> LENGTH: 14
<212> TYPE: PRT
<213> ORGANISM: Artificial Sequence
<220> FEATURE:
<223> OTHER INFORMATION: CETP mimotope

<400> SEQUENCE: 170

Gly Ser Pro Gln His Leu Thr Thr Asp Arg Ala Gln Ala Leu
1               5                   10

<210> SEQ ID NO 171
<211> LENGTH: 16
<212> TYPE: PRT
<213> ORGANISM: Artificial Sequence
<220> FEATURE:
<223> OTHER INFORMATION: CETP mimotope

<400> SEQUENCE: 171

Phe Gly Phe Pro Gln His Leu Thr Thr Asp Arg Ala Gln Ser Leu Ser
1               5                   10                  15

<210> SEQ ID NO 172
<211> LENGTH: 16
<212> TYPE: PRT
<213> ORGANISM: Artificial Sequence
<220> FEATURE:
<223> OTHER INFORMATION: CETP mimotope

<400> SEQUENCE: 172

Phe Gly Phe Pro Gln His Leu Thr Thr Asp Trp Ala Gln Ser Leu Ser
1               5                   10                  15

<210> SEQ ID NO 173
<211> LENGTH: 16
<212> TYPE: PRT
<213> ORGANISM: Artificial Sequence
<220> FEATURE:
<223> OTHER INFORMATION: CETP mimotope

<400> SEQUENCE: 173

Phe Gly Phe Pro Gln His Leu Thr Thr Asp Arg Leu Gln Ser Leu Ser
1               5                   10                  15

<210> SEQ ID NO 174
<211> LENGTH: 16
<212> TYPE: PRT
<213> ORGANISM: Artificial Sequence
<220> FEATURE:
```

<223> OTHER INFORMATION: CETP mimotope

<400> SEQUENCE: 174

Phe Gly Phe Pro Gln His Leu Thr Thr Asp Trp Leu Gln Ser Leu Ser
1               5                   10                  15

<210> SEQ ID NO 175
<211> LENGTH: 12
<212> TYPE: PRT
<213> ORGANISM: Artificial Sequence
<220> FEATURE:
<223> OTHER INFORMATION: CETP mimotope

<400> SEQUENCE: 175

Ala Thr Pro Ser His Leu Ile Ile Asp Arg Ala Gln
1               5                   10

<210> SEQ ID NO 176
<211> LENGTH: 15
<212> TYPE: PRT
<213> ORGANISM: Artificial Sequence
<220> FEATURE:
<223> OTHER INFORMATION: CETP mimotope

<400> SEQUENCE: 176

Ala Thr Pro Ser His Leu

```
<400> SEQUENCE: 180

Phe Gly Phe Pro Ser His Leu Ile Ile Asp Trp Ser Gln Ser Leu Ser
1               5                   10                  15

<210> SEQ ID NO 181
<211> LENGTH: 16
<212> TYPE: PRT
<213> ORGANISM: Artificial Sequence
<220> FEATURE:
<223> OTHER INFORMATION: CETP mimotope

<400> SEQUENCE: 181

Phe Ala Thr Pro Ser His Leu Ile Ile Asp Trp Leu Gln Ser Leu Ser
1               5                   10                  15

<210> SEQ ID NO 182
<211> LENGTH: 12
<212> TYPE: PRT
<213> ORGANISM: Artificial Sequence
<220> FEATURE:
<223> OTHER INFORMATION: CETP mimotope

<400> SEQUENCE: 182

Phe Lys Pro Ala His Val Ser Ile Asp Trp Leu Gln
1               5                   10

<210> SEQ ID NO 183
<211> LENGTH: 15
<212> TYPE: PRT
<213> ORGANISM: Artificial Sequence
<220> FEATURE:
<223> OTHER INFORMATION: CETP mimotope

<400> SEQUENCE: 183

Phe Lys Pro Ala His Val Ser Ile Asp Trp Leu Gln Ser Leu Ser
1               5                   10                  15

<210> SEQ ID NO 184
<211> LENGTH: 16
<212> TYPE: PRT
<213> ORGANISM: Artificial Sequence
<220> FEATURE:
<223> OTHER INFORMATION: CETP mimotope

<400> SEQUENCE: 184

Phe Gly Phe Pro Ala His Val Ser Ile Asp Trp Leu Gln Ser Leu Ser
1               5                   10                  15

<210> SEQ ID NO 185
<211> LENGTH: 16
<212> TYPE: PRT
<213> ORGANISM: Artificial Sequence
<220> FEATURE:
<223> OTHER INFORMATION: CETP mimotope

<400> SEQUENCE: 185

Ala Gly Phe Pro Ala His Val Ser Ile Asp Trp Leu Gln Ser Leu Ser
1               5                   10                  15

<210> SEQ ID NO 186
<211> LENGTH: 16
<212> TYPE: PRT
<213> ORGANISM: Artificial Sequence
<220> FEATURE:
<223> OTHER INFORMATION: CETP mimotope

<400> SEQUENCE: 186
```

Phe Ala Phe Pro Ala His Val Ser Ile Asp Trp Leu Gln Ser Leu Ser
1               5                   10                  15

<210> SEQ ID NO 187
<211> LENGTH: 16
<212> TYPE: PRT
<213> ORGANISM: Artificial Sequence
<220> FEATURE:
<223> OTHER INFORMATION: CETP mimotope

<400> SEQUENCE: 187

Phe Gly Ala Pro Ala His Val Ser Ile Asp Trp Leu Gln Ser Leu Ser
1               5                   10                  15

<210> SEQ ID NO 188
<211> LENGTH: 16
<212> TYPE: PRT
<213> ORGANISM: Artificial Sequence
<220> FEATURE:
<223> OTHER INFORMATION: CETP mimotope

<400> SEQUENCE: 188

Phe Gly Phe Ala Ala His Val Ser Ile Asp Trp Leu Gln Ser Leu Ser
1               5                   10                  15

<210> SEQ ID NO 189
<211> LENGTH: 16
<212> TYPE: PRT
<213> ORGANISM: Artificial Sequence
<220> FEATURE:
<223> OTHER INFORMATION: CETP mimotope

<400> SEQUENCE: 189

Phe Gly Phe Pro Ala His Val Ser Ala Asp Trp Leu Gln Ser Leu Ser
1               5                   10                  15

<210> SEQ ID NO 190
<211> LENGTH: 16
<212> TYPE: PRT
<213> ORGANISM: Artificial Sequence
<220> FEATURE:
<223> OTHER INFORMATION: CETP mimotope

<400> SEQUENCE: 190

Phe Gly Phe Pro Ala His Val Ser Ile Asp Trp Leu Gln Ala Leu Ser
1               5                   10                  15

<210> SEQ ID NO 191
<211> LENGTH: 16
<212> TYPE: PRT
<213> ORGANISM: Artificial Sequence
<220> FEATURE:
<223> OTHER INFORMATION: CETP mimotope

<400> SEQUENCE: 191

Phe Gly Phe Pro Ala His Val Ser Ile Asp Trp Leu Gln Ser Leu Ala
1               5                   10                  15

<210> SEQ ID NO 192
<211> LENGTH: 16
<212> TYPE: PRT
<213> ORGANISM: Artificial Sequence
<220> FEATURE:
<223> OTHER INFORMATION: CETP mimotope

<400> SEQUENCE: 192

Phe Ala Phe Pro Ala His Val Ser Ile Asp Trp Leu Gln Ala Leu Ala
1               5                   10                  15

```
<210> SEQ ID NO 193
<211> LENGTH: 16
<212> TYPE: PRT
<213> ORGANISM: Artificial Sequence
<220> FEATURE:
<223> OTHER INFORMATION: CETP mimotope

<400> SEQUENCE: 193

Phe Gly Phe Ala Ala His Val Ser Ile Asp Trp Leu Gln Ser Leu Ser
1               5                   10                  15

<210> SEQ ID NO 194
<211> LENGTH: 16
<212> TYPE: PRT
<213> ORGANISM: Artificial Sequence
<220> FEATURE:
<223> OTHER INFORMATION: CETP mimotope

<400> SEQUENCE: 194

Phe Gly Phe Phe Ala His Val Ser Ile Asp Trp Leu Gln Ser Leu Ser
1               5                   10                  15

<210> SEQ ID NO 195
<211> LENGTH: 16
<212> TYPE: PRT
<213> ORGANISM: Artificial Sequence
<220> FEATURE:
<223> OTHER INFORMATION: CETP mimotope

<400> SEQUENCE: 195

Phe Gly Phe Pro Ala His Val Ser Ile Arg Trp Leu Gln Ser Leu Ser
1               5                   10                  15

<210> SEQ ID NO 196
<211> LENGTH: 16
<212> TYPE: PRT
<213> ORGANISM: Artificial Sequence
<220> FEATURE:
<223> OTHER INFORMATION: CETP mimotope

<400> SEQUENCE: 196

Phe Gly Phe Pro Ala His Val Ser Ile Glu Trp Leu Gln Ser Leu Ser
1               5                   10                  15

<210> SEQ ID NO 197
<211> LENGTH: 16
<212> TYPE: PRT
<213> ORGANISM: Artificial Sequence
<220> FEATURE:
<223> OTHER INFORMATION: CETP mimotope

<400> SEQUENCE: 197

Phe Gly Phe Pro Ala His Val Ser Ile Asp Trp Leu Asn Ser Leu Ser
1               5                   10                  15

<210> SEQ ID NO 198
<211> LENGTH: 16
<212> TYPE: PRT
<213> ORGANISM: Artificial Sequence
<220> FEATURE:
<223> OTHER INFORMATION: CETP mimotope

<400> SEQUENCE: 198

Phe Gly Phe Pro Ala His Val Ser Ile Asp Trp Leu His Ser Leu Ser
1               5                   10                  15
```

```
<210> SEQ ID NO 199
<211> LENGTH: 16
<212> TYPE: PRT
<213> ORGANISM: Artificial Sequence
<220> FEATURE:
<223> OTHER INFORMATION: CETP mimotope

<400> SEQUENCE: 199

Ala Gly Phe Pro Ala His Val Ser Ile Asp Trp Leu Gln Ser Leu Ser
1               5                   10                  15

<210> SEQ ID NO 200
<211> LENGTH: 16
<212> TYPE: PRT
<213> ORGANISM: Artificial Sequence
<220> FEATURE:
<223> OTHER INFORMATION: CETP mimotope

<400> SEQUENCE: 200

Pro Gly Phe Pro Ala His Val Ser Ile Asp Trp Leu Gln Ser Leu Ser
1               5                   10                  15

<210> SEQ ID NO 201
<211> LENGTH: 16
<212> TYPE: PRT
<213> ORGANISM: Artificial Sequence
<220> FEATURE:
<223> OTHER INFORMATION: CETP mimotope

<400> SEQUENCE: 201

Trp Gly Phe Pro Ala His Val Ser Ile Asp Trp Leu Gln Ser Leu Ser
1               5                   10                  15

<210> SEQ ID NO 202
<211> LENGTH: 16
<212> TYPE: PRT
<213> ORGANISM: Artificial Sequence
<220> FEATURE:
<223> OTHER INFORMATION: CETP mimotope

<400> SEQUENCE: 202

Phe Ala Phe Pro Ala His Val Ser Ile Asp Trp Leu Gln Ser Leu Ser
1               5                   10                  15

<210> SEQ ID NO 203
<211> LENGTH: 16
<212> TYPE: PRT
<213> ORGANISM: Artificial Sequence
<220> FEATURE:
<223> OTHER INFORMATION: CETP mimotope

<400> SEQUENCE: 203

Phe Ser Phe Pro Ala His Val Ser Ile Asp Trp Leu Gln Ser Leu Ser
1               5                   10                  15

<210> SEQ ID NO 204
<211> LENGTH: 16
<212> TYPE: PRT
<213> ORGANISM: Artificial Sequence
<220> FEATURE:
<223> OTHER INFORMATION: CETP mimotope

<400> SEQUENCE: 204

Phe Tyr Phe Pro Ala His Val Ser Ile Asp Trp Leu Gln Ser Leu Ser
1               5                   10                  15

<210> SEQ ID NO 205
<211> LENGTH: 16
```

```
<212> TYPE: PRT
<213> ORGANISM: Artificial Sequence
<220> FEATURE:
<223> OTHER INFORMATION: CETP mimotope

<400> SEQUENCE: 205

Phe Asp Phe Pro Ala His Val Ser Ile Asp Trp Leu Gln Ser Leu Ser
1               5                   10                  15

<210> SEQ ID NO 206
<211> LENGTH: 16
<212> TYPE: PRT
<213> ORGANISM: Artificial Sequence
<220> FEATURE:
<223> OTHER INFORMATION: CETP mimotope

<400> SEQUENCE: 206

Phe Gly Ala Pro Ala His Val Ser Ile Asp Trp Leu Gln Ser Leu Ser
1               5                   10                  15

<210> SEQ ID NO 207
<211> LENGTH: 16
<212> TYPE: PRT
<213> ORGANISM: Artificial Sequence
<220> FEATURE:
<223> OTHER INFORMATION: CETP mimotope

<400> SEQUENCE: 207

Phe Gly Phe Pro Ala His Val Ser Ile Asp Trp Leu Gln Leu Leu Ser
1               5                   10                  15

<210> SEQ ID NO 208
<211> LENGTH: 16
<212> TYPE: PRT
<213> ORGANISM: Artificial Sequence
<220> FEATURE:
<223> OTHER INFORMATION: CETP mimotope

<400> SEQUENCE: 208

Phe Gly Phe Pro Ala His Val Ser Ile Asp Trp Leu Gln Trp Leu Ser
1               5                   10                  15

<210> SEQ ID NO 209
<211> LENGTH: 16
<212> TYPE: PRT
<213> ORGANISM: Artificial Sequence
<220> FEATURE:
<223> OTHER INFORMATION: CETP mimotope

<400> SEQUENCE: 209

Phe Gly Phe Pro Ala His Val Ser Ile Asp Trp Leu Gln Asn Leu Ser
1               5                   10                  15

<210> SEQ ID NO 210
<211> LENGTH: 16
<212> TYPE: PRT
<213> ORGANISM: Artificial Sequence
<220> FEATURE:
<223> OTHER INFORMATION: CETP mimotope

<400> SEQUENCE: 210

Phe Gly Phe Pro Ala His Val Ser Ile Asp Trp Leu Gln Thr Leu Ser
1               5                   10                  15

<210> SEQ ID NO 211
<211> LENGTH: 16
<212> TYPE: PRT
<213> ORGANISM: Artificial Sequence
```

-continued

```
<220> FEATURE:
<223> OTHER INFORMATION: CETP mimotope

<400> SEQUENCE: 211

Phe Gly Phe Pro Ala His Val Ser Ile Asp Trp Leu Gln Tyr Leu Ser
1               5                   10                  15

<210> SEQ ID NO 212
<211> LENGTH: 16
<212> TYPE: PRT
<213> ORGANISM: Artificial Sequence
<220> FEATURE:
<223> OTHER INFORMATION: CETP mimotope

<400> SEQUENCE: 212

Phe Gly Phe Pro Ala His Val Ser Ile Asp Trp Leu Gln Ser Ile Ser
1               5                   10                  15

<210> SEQ ID NO 213
<211> LENGTH: 16
<212> TYPE: PRT
<213> ORGANISM: Artificial Sequence
<220> FEATURE:
<223> OTHER INFORMATION: CETP mimotope

<400> SEQUENCE: 213

Phe Gly Phe Pro Ala His Val Ser Ile Asp Trp Leu Gln Ser Leu Thr
1               5                   10                  15

<210> SEQ ID NO 214
<211> LENGTH: 16
<212> TYPE: PRT
<213> ORGANISM: Artificial Sequence
<220> FEATURE:
<223> OTHER INFORMATION: CETP mimotope

<400> SEQUENCE: 214

Phe Gly Phe Pro Ala His Val Ser Ile Asp Trp Leu Gln Ser Leu Tyr
1               5                   10                  15

<210> SEQ ID NO 215
<211> LENGTH: 16
<212> TYPE: PRT
<213> ORGANISM: Artificial Sequence
<220> FEATURE:
<223> OTHER INFORMATION: CETP mimotope

<400> SEQUENCE: 215

Phe Ala Phe Pro Ala His Val Ser Ile Asp Trp Leu Gln Ala Leu Ala
1               5                   10                  15

<210> SEQ ID NO 216
<211> LENGTH: 16
<212> TYPE: PRT
<213> ORGANISM: Artificial Sequence
<220> FEATURE:
<223> OTHER INFORMATION: CETP mimotope

<400> SEQUENCE: 216

Phe Gly Phe Pro Ala His Val Ser Ile Asp Arg Ala Gln Ser Leu Ser
1               5                   10                  15

<210> SEQ ID NO 217
<211> LENGTH: 16
<212> TYPE: PRT
<213> ORGANISM: Artificial Sequence
<220> FEATURE:
<223> OTHER INFORMATION: CETP mimotope
```

<400> SEQUENCE: 217

Phe Gly Phe Pro Thr His Val Ser Ile Asp Trp Leu Gln Ser Leu Ser
1               5                   10                  15

<210> SEQ ID NO 218
<211> LENGTH: 16
<212> TYPE: PRT
<213> ORGANISM: Artificial Sequence
<220> FEATURE:
<223> OTHER INFORMATION: CETP mimotope

<400> SEQUENCE: 218

Phe Gly Phe Pro Phe His Val Ser Ile Asp Trp Leu Gln Ser Leu Ser
1               5                   10                  15

<210> SEQ ID NO 219
<211> LENGTH: 16
<212> TYPE: PRT
<213> ORGANISM: Artificial Sequence
<220> FEATURE:
<223> OTHER INFORMATION: CETP mimotope

<400> SEQUENCE: 219

Phe Gly Phe Pro Ala His Ile Ser Ile Asp Trp Leu Gln Ser Leu Ser
1               5                   10                  15

<210> SEQ ID NO 220
<211> LENGTH: 16
<212> TYPE: PRT
<213> ORGANISM: Artificial Sequence
<220> FEATURE:
<223> OTHER INFORMATION: CETP mimotope

<400> SEQUENCE: 220

Phe Gly Phe Pro Ala His Ile Ile Ile Asp Trp Leu Gln Ser Leu Ser
1               5                   10                  15

<210> SEQ ID NO 221
<211> LENGTH: 16
<212> TYPE: PRT
<213> ORGANISM: Artificial Sequence
<220> FEATURE:
<223> OTHER INFORMATION: CETP mimotope

<400> SEQUENCE: 221

Phe Gly Phe Pro Ala His Leu Thr Thr Asp Trp Leu Gln Ser Leu Ser
1               5                   10                  15

<210> SEQ ID NO 222
<211> LENGTH: 16
<212> TYPE: PRT
<213> ORGANISM: Artificial Sequence
<220> FEATURE:
<223> OTHER INFORMATION: CETP mimotope

<400> SEQUENCE: 222

Phe Gly Phe Pro Ala His Val Phe Ile Asp Trp Leu Gln Ser Leu Ser
1               5                   10                  15

<210> SEQ ID NO 223
<211> LENGTH: 16
<212> TYPE: PRT
<213> ORGANISM: Artificial Sequence
<220> FEATURE:
<223> OTHER INFORMATION: CETP mimotope

<400> SEQUENCE: 223

```
Phe Gly Phe Pro Ala His Val Tyr Ile Asp Trp Leu Gln Ser Leu Ser
1               5                   10                  15
```

<210> SEQ ID NO 224
<211> LENGTH: 16
<212> TYPE: PRT
<213> ORGANISM: Artificial Sequence
<220> FEATURE:
<223> OTHER INFORMATION: CETP mimotope

<400> SEQUENCE: 224

```
Phe Gly Phe Pro Ala His Val Ser Leu Asp Trp Leu Gln Ser Leu Ser
1               5                   10                  15
```

<210> SEQ ID NO 225
<211> LENGTH: 16
<212> TYPE: PRT
<213> ORGANISM: Artificial Sequence
<220> FEATURE:
<223> OTHER INFORMATION: CETP mimotope

<400> SEQUENCE: 225

```
Phe Gly Phe Pro Ala His Val Ser Ala Asp Trp Leu Gln Ser Leu Ser
1               5                   10                  15
```

<210> SEQ ID NO 226
<211> LENGTH: 14
<212> TYPE: PRT
<213> ORGANISM: Artificial Sequence
<220> FEATURE:
<223> OTHER INFORMATION: CETP mimotope

<400> SEQUENCE: 226

```
Thr Pro Thr His Tyr Tyr Ala Asp Phe Ser Gln Ser Leu Ser
1               5                   10
```

<210> SEQ ID NO 227
<211> LENGTH: 16
<212> TYPE: PRT
<213> ORGANISM: Artificial Sequence
<220> FEATURE:
<223> OTHER INFORMATION: CETP mimotope

<400> SEQUENCE: 227

```
Phe Gly Phe Pro Ala His Val Ser Ile Asp Trp Ser Gln Ser Leu Ser
1               5                   10                  15
```

<210> SEQ ID NO 228
<211> LENGTH: 16
<212> TYPE: PRT
<213> ORGANISM: Artificial Sequence
<220> FEATURE:
<223> OTHER INFORMATION: CETP mimotope

<400> SEQUENCE: 228

```
Phe Gly Phe Pro Ala His Val Ser Ile Asp Phe Ser Gln Ser Leu Ser
1               5                   10                  15
```

<210> SEQ ID NO 229
<211> LENGTH: 16
<212> TYPE: PRT
<213> ORGANISM: Artificial Sequence
<220> FEATURE:
<223> OTHER INFORMATION: CETP mimotope

<400> SEQUENCE: 229

```
Phe Gly Phe Pro Ala His Val Trp Ile Asp Trp Leu Gln Ser Leu Ser
```

```
                1               5                   10                  15
```

<210> SEQ ID NO 230
<211> LENGTH: 16
<212> TYPE: PRT
<213> ORGANISM: Artificial Sequence
<220> FEATURE:
<223> OTHER INFORMATION: CETP mimotope

<400> SEQUENCE: 230

```
Phe Gly Phe Pro Ala His Val Phe Ile Asp Trp Leu Gln Ser Leu Asn
1               5                   10                  15
```

<210> SEQ ID NO 231
<211> LENGTH: 16
<212> TYPE: PRT
<213> ORGANISM: Artificial Sequence
<220> FEATURE:
<223> OTHER INFORMATION: CETP mimotope

<400> SEQUENCE: 231

```
Phe Gly Phe Pro Ala His Phe Ser Ile Asp Trp Leu Gln Ser Leu Ser
1               5                   10                  15
```

<210> SEQ ID NO 232
<211> LENGTH: 16
<212> TYPE: PRT
<213> ORGANISM: Artificial Sequence
<220> FEATURE:
<223> OTHER INFORMATION: CETP mimotope

<400> SEQUENCE: 232

```
Phe Gly Phe Pro Ala His Val Ser Phe Asp Trp Leu Gln Ser Leu Ser
1               5                   10                  15
```

<210> SEQ ID NO 233
<211> LENGTH: 16
<212> TYPE: PRT
<213> ORGANISM: Artificial Sequence
<220> FEATURE:
<223> OTHER INFORMATION: CETP mimotope

<400> SEQUENCE: 233

```
Phe Gly Phe Pro Glu His Val Phe Ile Asp Trp Leu Gln Ser Leu Ser
1               5                   10                  15
```

<210> SEQ ID NO 234
<211> LENGTH: 17
<212> TYPE: PRT
<213> ORGANISM: Artificial Sequence
<220> FEATURE:
<223> OTHER INFORMATION: CETP mimotope

<400> SEQUENCE: 234

```
Asp Phe Gly Phe Pro Ala His Val Phe Ile Asp Trp Leu Gln Ser Leu
1               5                   10                  15

Ser
```

<210> SEQ ID NO 235
<211> LENGTH: 17
<212> TYPE: PRT
<213> ORGANISM: Artificial Sequence
<220> FEATURE:
<223> OTHER INFORMATION: CETP mimotope

<400> SEQUENCE: 235

```
Asp Phe Gly Phe Pro Ser His Leu Ile Ile Asp Trp Leu Gln Ser Leu
```

```
1               5                   10                  15
Ser

<210> SEQ ID NO 236
<211> LENGTH: 17
<212> TYPE: PRT
<213> ORGANISM: Artificial Sequence
<220> FEATURE:
<223> OTHER INFORMATION: CETP mimotope

<400> SEQUENCE: 236

Asp Phe Gly Phe Pro Ala His Val Tyr Ile Asp Trp Leu Gln Ser Leu
1               5                   10                  15

Ser

<210> SEQ ID NO 237
<211> LENGTH: 16
<212> TYPE: PRT
<213> ORGANISM: Artificial Sequence
<220> FEATURE:
<223> OTHER INFORMATION: CETP mimotope

<400> SEQUENCE: 237

Phe Gly Phe Pro Gln His Leu Phe Thr Asp Trp Leu Gln Ser Leu Ser
1               5                   10                  15

<210> SEQ ID NO 238
<211> LENGTH: 16
<212> TYPE: PRT
<213> ORGANISM: Artificial Sequence
<220> FEATURE:
<223> OTHER INFORMATION: CETP mimotope

<400> SEQUENCE: 238

Phe Gly Phe Pro Lys His Leu Leu Val Asp Phe Leu Gln Ser Leu Ser
1               5                   10                  15

<210> SEQ ID NO 239
<211> LENGTH: 16
<212> TYPE: PRT
<213> ORGANISM: Artificial Sequence
<220> FEATURE:
<223> OTHER INFORMATION: CETP mimotope

<400> SEQUENCE: 239

Phe Gly Phe Pro Ser His Ile Ile Ile Asp Trp Leu Gln Ser Leu Ser
1               5                   10                  15

<210> SEQ ID NO 240
<211> LENGTH: 16
<212> TYPE: PRT
<213> ORGANISM: Artificial Sequence
<220> FEATURE:
<223> OTHER INFORMATION: CETP mimotope

<400> SEQUENCE: 240

Phe Gly Phe Pro Ser His Leu Ile Ile Glu Trp Leu Gln Ser Leu Ser
1               5                   10                  15

<210> SEQ ID NO 241
<211> LENGTH: 16
<212> TYPE: PRT
<213> ORGANISM: Artificial Sequence
<220> FEATURE:
<223> OTHER INFORMATION: CETP mimotope

<400> SEQUENCE: 241
```

```
Ala Ala Phe Pro Ala His Leu Leu Ala Asp Ala Ala Gln Ala Leu Ala
1               5                   10                  15
```

<210> SEQ ID NO 242
<211> LENGTH: 16
<212> TYPE: PRT
<213> ORGANISM: Artificial Sequence
<220> FEATURE:
<223> OTHER INFORMATION: CETP mimotope

<400> SEQUENCE: 242

```
Ala Ala Phe Pro Ala His Ala Ala Ala Asp Phe Leu Gln Ala Leu Ala
1               5                   10                  15
```

<210> SEQ ID NO 243
<211> LENGTH: 16
<212> TYPE: PRT
<213> ORGANISM: Artificial Sequence
<220> FEATURE:
<223> OTHER INFORMATION: CETP mimotope

<400> SEQUENCE: 243

```
Ala Ala Phe Ala Ala His Leu Leu Ala Asp Phe Leu Gln Ala Ala Ala
1               5                   10                  15
```

<210> SEQ ID NO 244
<211> LENGTH: 16
<212> TYPE: PRT
<213> ORGANISM: Artificial Sequence
<220> FEATURE:
<223> OTHER INFORMATION: CETP mimotope

<400> SEQUENCE: 244

```
Ala Ala Ala Pro Ala His Leu Leu Val Asp Ala Ala Gln Ala Ala Ala
1               5                   10                  15
```

<210> SEQ ID NO 245
<211> LENGTH: 16
<212> TYPE: PRT
<213> ORGANISM: Artificial Sequence
<220> FEATURE:
<223> OTHER INFORMATION: CETP mimotope

<400> SEQUENCE: 245

```
Phe Ala Phe Pro Ala His Val Phe Ile Asp Trp Leu Gln Ser Leu Ser
1               5                   10                  15
```

<210> SEQ ID NO 246
<211> LENGTH: 16
<212> TYPE: PRT
<213> ORGANISM: Artificial Sequence
<220> FEATURE:
<223> OTHER INFORMATION: CETP mimotope

<400> SEQUENCE: 246

```
Phe Gly Phe Pro Ala His Val Phe Ile Asp Trp Leu Gln Ala Leu Ser
1               5                   10                  15
```

<210> SEQ ID NO 247
<211> LENGTH: 16
<212> TYPE: PRT
<213> ORGANISM: Artificial Sequence
<220> FEATURE:
<223> OTHER INFORMATION: CETP mimotope

<400> SEQUENCE: 247

Phe Gly Phe Pro Ala His Val Phe Ile Asp Trp Leu Gln Ser Leu Ala

```
                 1               5                  10                 15
```

<210> SEQ ID NO 248
<211> LENGTH: 15
<212> TYPE: PRT
<213> ORGANISM: Artificial Sequence
<220> FEATURE:
<223> OTHER INFORMATION: CETP mimotope

<400> SEQUENCE: 248

```
Gly Phe Pro Ala His Val Phe Ile Asp Trp Leu Gln Ser Leu Ser
1               5                   10                  15
```

<210> SEQ ID NO 249
<211> LENGTH: 14
<212> TYPE: PRT
<213> ORGANISM: Artificial Sequence
<220> FEATURE:
<223> OTHER INFORMATION: CETP mimotope

<400> SEQUENCE: 249

```
Phe Pro Ala His Val Phe Ile Asp Trp Leu Gln Ser Leu Ser
1               5                   10
```

<210> SEQ ID NO 250
<211> LENGTH: 13
<212> TYPE: PRT
<213> ORGANISM: Artificial Sequence
<220> FEATURE:
<223> OTHER INFORMATION: CETP mimotope

<400> SEQUENCE: 250

```
Pro Ala His Val Phe Ile Asp Trp Leu Gln Ser Leu Ser
1               5                   10
```

<210> SEQ ID NO 251
<211> LENGTH: 16
<212> TYPE: PRT
<213> ORGANISM: Artificial Sequence
<220> FEATURE:
<223> OTHER INFORMATION: CETP mimotope

<400> SEQUENCE: 251

```
Phe Ala Phe Pro Ala His Val Phe Ile Asp Trp Leu Gln Ala Leu Ala
1               5                   10                  15
```

<210> SEQ ID NO 252
<211> LENGTH: 16
<212> TYPE: PRT
<213> ORGANISM: Artificial Sequence
<220> FEATURE:
<223> OTHER INFORMATION: CETP mimotope

<400> SEQUENCE: 252

```
Phe Gly Phe Pro Glu His Leu Phe Val Asp Phe Leu Gln Ser Leu Ser
1               5                   10                  15
```

<210> SEQ ID NO 253
<211> LENGTH: 16
<212> TYPE: PRT
<213> ORGANISM: Artificial Sequence
<220> FEATURE:
<223> OTHER INFORMATION: CETP mimotope

<400> SEQUENCE: 253

```
Phe Gly Phe Pro Ala His Val His Ile Asp Trp Leu Gln Ser Leu Ser
1               5                   10                  15
```

<210> SEQ ID NO 254
<211> LENGTH: 16
<212> TYPE: PRT
<213> ORGANISM: Artificial Sequence
<220> FEATURE:
<223> OTHER INFORMATION: CETP mimotope

<400> SEQUENCE: 254

Phe Gly Phe Pro Ala His Val Pro Ile Asp Trp Leu Gln Ser Leu Ser
1               5                   10                  15

<210> SEQ ID NO 255
<211> LENGTH: 16
<212> TYPE: PRT
<213> ORGANISM: Artificial Sequence
<220> FEATURE:
<223> OTHER INFORMATION: CETP mimotope

<400> SEQUENCE: 255

Phe Gly Phe Pro Ser His Leu Phe Ile Asp Trp Ala Gln Ser Leu Ser
1               5                   10                  15

<210> SEQ ID NO 256
<211> LENGTH: 16
<212> TYPE: PRT
<213> ORGANISM: Artificial Sequence
<220> FEATURE:
<223> OTHER INFORMATION: CETP mimotope

<400> SEQUENCE: 256

Pro Gly Phe Pro Ala His Val Phe Ile Asp Trp Leu Gln Leu Ile Thr
1               5                   10                  15

<210> SEQ ID NO 257
<211> LENGTH: 13
<212> TYPE: PRT
<213> ORGANISM: Artificial Sequence
<220> FEATURE:
<223> OTHER INFORMATION: CETP mimotope

<400> SEQUENCE: 257

Pro Ala His Val Tyr Ile Asp Trp Leu Gln Ser Leu Ser
1               5                   10

<210> SEQ ID NO 258
<211> LENGTH: 13
<212> TYPE: PRT
<213> ORGANISM: Artificial Sequence
<220> FEATURE:
<223> OTHER INFORMATION: CETP mimotope

<400> SEQUENCE: 258

Phe Gly Phe Pro Ala His Val Tyr Ile Asp Trp Leu Gln
1               5                   10

<210> SEQ ID NO 259
<211> LENGTH: 13
<212> TYPE: PRT
<213> ORGANISM: Artificial Sequence
<220> FEATURE:
<223> OTHER INFORMATION: CETP mimotope

<400> SEQUENCE: 259

Phe Gly Phe Pro Ala His Val Phe Ile Asp Trp Leu Gln
1               5                   10

<210> SEQ ID NO 260

```
<211> LENGTH: 17
<212> TYPE: PRT
<213> ORGANISM: Artificial Sequence
<220> FEATURE:
<223> OTHER INFORMATION: CETP mimotope

<400> SEQUENCE: 260

Asp Phe Gly Phe Pro Ala His Val Phe Ile Asp Trp Leu Gln Ser Leu
1               5                   10                  15

Asn

<210> SEQ ID NO 261
<211> LENGTH: 10
<212> TYPE: PRT
<213> ORGANISM: Artificial Sequence
<220> FEATURE:
<223> OTHER INFORMATION: CETP mimotope

<400> SEQUENCE: 261

Pro Ser His Leu Ile Ile Asp Trp Leu Gln
1               5                   10

<210> SEQ ID NO 262
<211> LENGTH: 10
<212> TYPE: PRT
<213> ORGANISM: Artificial Sequence
<220> FEATURE:
<223> OTHER INFORMATION: CETP mimotope

<400> SEQUENCE: 262

Pro Ala His Val Phe Ile Asp Trp Leu Gln
1               5                   10

<210> SEQ ID NO 263
<211> LENGTH: 17
<212> TYPE: PRT
<213> ORGANISM: Artificial Sequence
<220> FEATURE:
<223> OTHER INFORMATION: CETP mimotope

<400> SEQUENCE: 263

Asp Phe Gly Phe Pro Ala His Val Thr Ile Asp Trp Leu Gln Ser Leu
1               5                   10                  15

Asn

<210> SEQ ID NO 264
<211> LENGTH: 17
<212> TYPE: PRT
<213> ORGANISM: Artificial Sequence
<220> FEATURE:
<223> OTHER INFORMATION: CETP mimotope

<400> SEQUENCE: 264

Asp Phe Gly Phe Pro Ala His Val Leu Ile Asp Trp Leu Gln Ser Leu
1               5                   10                  15

Asn

<210> SEQ ID NO 265
<211> LENGTH: 16
<212> TYPE: PRT
<213> ORGANISM: Artificial Sequence
<220> FEATURE:
<223> OTHER INFORMATION: CETP mimotope

<400> SEQUENCE: 265

Phe Gly Phe Pro Ala His Val Phe Ile Asp Trp Leu Gln Ser Leu Ala
```

```
<210> SEQ ID NO 266
<211> LENGTH: 15
<212> TYPE: PRT
<213> ORGANISM: Artificial Sequence
<220> FEATURE:
<223> OTHER INFORMATION: CETP mimotope

<400> SEQUENCE: 266

Phe Lys Pro Ala His Val Phe Ile Asp Trp Leu Gln Ser Leu Ser
1               5                   10                  15

<210> SEQ ID NO 267
<211> LENGTH: 16
<212> TYPE: PRT
<213> ORGANISM: Artificial Sequence
<220> FEATURE:
<223> OTHER INFORMATION: CETP mimotope

<400> SEQUENCE: 267

Gly Phe Lys Pro Ala His Val Phe Ile Asp Trp Leu Gln Ser Leu Ser
1               5                   10                  15

<210> SEQ ID NO 268
<211> LENGTH: 17
<212> TYPE: PRT
<213> ORGANISM: Artificial Sequence
<220> FEATURE:
<223> OTHER INFORMATION: CETP mimotope

<400> SEQUENCE: 268

Phe Pro Gly Phe Pro Ala His Val Phe Ile Asp Trp Leu Gln Leu Ile
1               5                   10                  15

Thr

<210> SEQ ID NO 269
<211> LENGTH: 15
<212> TYPE: PRT
<213> ORGANISM: Artificial Sequence
<220> FEATURE:
<223> OTHER INFORMATION: CETP mimotope

<400> SEQUENCE: 269

Phe Gly Phe Pro Ala His Val Trp Ile Asp Trp Leu Gln Ser Leu
1               5                   10                  15

<210> SEQ ID NO 270
<211> LENGTH: 16
<212> TYPE: PRT
<213> ORGANISM: Artificial Sequence
<220> FEATURE:
<223> OTHER INFORMATION: CETP mimotope

<400> SEQUENCE: 270

Gly Phe Lys Pro Ala His Val Phe Ile Asp Trp Leu Gln Ser Leu Ser
1               5                   10                  15
```

TREATMENT OF ATHEROSCLEROSIS WITH CHOLESTEROL ESTER TRANSPORT PROTEIN MIMOTOPES

The invention relates to the prevention and treatment of atherosclerosis, atherosclerosis risk diseases and atherosclerosis sequelae.

Atherosclerotic sequelae, such as the peripheral arterial occlusion disease, coronary heart disease as well as the apoplectic cerebral insultus, are still among the main causes of death in the United States, Europe, and in large parts of Asia. The development of the atherosclerosis is considered to be a chronic progressive inflammation of the arterial vessel wall which is characterized by a complex interaction of growth factors, cytokines and cell interactions. According to the "response-to-injury" hypothesis, the "injury" of the endothelium constitutes the initial event of the disease, leading to an endothelial dysfunction which triggers a cascade of cellular interactions culminating in the formation of the atherosclerotic lesions. As risk factors promoting such an "injury", exogenous and endogenous influences are mentioned which correlate statistically significantly with atherosclerosis. Increased and modified LDL, Lp(a), arterial hypertension, Diabetes mellitus and hyperhomocysteinaemia are, for instance, counted among the most important ones of these endothelium-damaging factors. Since the endothelium does not constitute a rigid, but much rather an extremely dynamic barrier, a plurality of molecular changes occur in the course of the endothelial dysfunction in addition to an increased permeability for lipoproteins, which molecular changes have a decisive influence on the interaction of monocytes, T-lymphocytes and endothelial cells. By the expression of endothelial adhesion molecules of the type of the E, L and P selectins, integrins, ICMA-1, VCAM-1 and platelet-endothelial-cell adhesion molecule-1, adhesion of monocytes and T-lymphocytes at the lumen side occurs. The subsequent migration of the leukocytes over the endothelium is mediated by MCP-1, interleukin-8, PDGF, MCSF and osteopontin. Via the so-called scavenger receptor, macrophages and monocytes resident in the intima are capable of taking up the penetrated LDL particles and to deposit them as vacuoles of cholesterol esters in the cytoplasma. The foam cells formed in this manner accumulate mainly in groups in the region of the vessel intima and form the "fatty streak" lesions occurring already in childhood. LDL are lipoproteins of low density and are formed by catabolic effects of lipolytic enzymes from VLDL particles rich in triglyceride. Besides their damaging properties on endothelial cells and smooth muscle cells of the media, LDL moreover has a chemotactic effect on monocytes and is capable of increasing the expression of MCSF and MCP-1 of the endothelial cells via gene amplification. In contrast to LDL, HDL is capable of taking up cholesterol esters from loaded macrophages mediated by apolipoprotein E, under formation of so-called HDLc complexes. By the interaction of SR-B1 receptors, these cholesterol ester-loaded particles are capable of binding to hepatocytes or to cells of the adrenal cortex and delivering cholesterol for the production of bile acids and steroids, respectively. This mechanism is called reverse cholesterol transport and elucidates the protective function of HDL. Activated macrophages are capable of presenting antigens via HLA-DR and thereby activate CD4 and CD8 lymphocytes which, consequently, are stimulated to secrete cytokines, such as IFN-gamma and TNF-alpha, and moreover, contribute to increasing the inflammatory reaction. In the further course of the disease, smooth muscle cells of the media start to grow into the region of the intima which has been altered by inflammation. By this, the intermediary lesion forms at this stage. Starting from the intermediary lesion, the progressive and complicated lesion will develop over time, which is morphologically characterized by a necrotic core, cellular detritus and a fibrinous cap rich in collagen on the side of the lumen. If the cell number and the portion of the lipoids increase continuously, tears in the endothelium will occur, and surfaces with thrombotic properties will be exposed. Due to the adhesion and activation of thrombocytes at these tears, granules will be released which contain cytokines, growth factors and thrombin. Proteolytic enzymes of the macrophages are responsible for the thinning of the fibrinous cap which, at last, will lead to a rupture of the plaques with consecutive thrombosis and stenosing of the vessels and an acute ischemia of the terminal vessels.

Various risk factors are held responsible for the forming of atherosclerotic lesions. Hyperlipoproteinemia, arterial hypertension and abuse of nicotine are of particular significance in this respect. A disease which involves an excessive increase in the total and LDL cholesterol is the familial hypercholesterinemia (FH). It belongs to the most frequent monogenetically inherited metabolic diseases. The moderate heterozygous form occurs with a frequency of 1:500, the homozygous form with 1:1 million clearly more rarely. Causes of the familial hypercholesterinemia are mutations in the LDL receptor gene on the short arm of chromosome 19. These mutations may be deletions, insertions or point mutations. The characteristic finding of the lipoproteins in familial hypercholesterinemia is an increase in the total and LDL cholesterol at mostly normal triglyceride and VLDL concentrations. Often the HDL is lowered. Phenotypically, there is a type IIAa-hyperlipoproteinemia. In the heterozygous form, the total cholesterol is increased by the two to three-fold, in the homozygous form it is increased by the five to six-fold as compared to the normal level. Clinically the familial hypercholesterinemia manifests itself by an early coronary sclerosis. As a rule, in heterozygous men the first symptoms of a coronary heart disease (CHD) occur between their $30^{th}$ and the $40^{th}$ year of age, in women on an average 10 years later. 50% of the afflicted men die of the consequences of their coronary sclerosis before they are 50 years old. Besides the massively increased LDL levels, also lowered HDL concentrations are responsible for the rapid progress of atherosclerosis. Atherosclerotic changes may become manifest also on extracardiac vessels, such as the aorta, the carotid arteries and peripheral arteries. With the homozygous form of the disease, the coronary sclerosis develops already in early childhood. The first myocardial infarction often occurs before the $10^{th}$ year of age, and in most cases the afflicted persons die before they are 20 years old. The development of xanthomas is a function of the level of the serum cholesterol and the duration of the disease. Approximately 75% of the heterozygous individuals afflicted who are more than 20 years old exhibit tendinous xanthomas. The homozygous individuals have skin and tendon xanthomas in nearly 100%. Lipid deposits may also occur on the eye lid and in the cornea (xanthelasmas; *Arcus lipoides*). These are, however, not a specific sign of a hypercholesterinemia, since they are also found with normal cholesterol levels. Furthermore, with the FH, acute arthritides and tendosynovitides occur frequently. The individual lipoproteins differ with respect to size and density, since they contain differently large portions of lipids and proteins, so-called apoproteins. The density increases with increasing protein and decreasing lipid portion. Due to their different densities, they can be separated into different fractions by ultracentrifugation. This is the basis for the classification of the lipoproteins into their main groups: chylomicrones, very-low-density lipoproteins (VLDL), intermediate-density lipoproteins (IDL), low-density lipoproteins (LDL), high-density lipoproteins (HDL), lipoprotein (a) (Lp(a)). Among the lipoproteins with a high atherogenic potential there are primarily the LDL, the Lp(a) and the VLDL. LDL has a density of approximately d=1.006-1.063 g/ml. The core is formed by esterified cholesterol molecules. This highly hydrophobic core is surrounded by an envelope of phospholipids, non-esterified cholesterol and one single Apo B100 molecule. Besides, Apoprotein E is found on the surface of the LDL particles. The function of the LDL consists in transporting cholesterol to peripheral tissues where—mediated by the apoprotein B-100—it is taken up into the cells via the LDL receptor. In comprehensive epidemiologic studies, a positive correlation between the level of the serum cholesterol and the occurrence of a coronary heart disease could be demonstrated. LDL cholesterol levels of higher than 160 mg/dl constitute a high cardiovascular risk. Besides the level of the LDL cholesterol, also the level of the vessel-protecting HDL cholesterol plays an important role when estimating the risk profile for cardiovascular diseases. Levels of below 35 mg/dl are associated with an increased risk. VLDL are lipoproteins with a low density (d=0.94-1.006 g/ml) and a high triglyceride portion. Substantially, VLDL contain apoprotein C, and small portions of apoproteins B-100 and E. Different from chylomicrons, VLDL do not consist of food lipids, but are synthesized in the liver from endogenously formed triglycerides and secreted into circulation. As with the chylomicrons, the triglycerides are hydrolyzed by the aproprotein C-II-activated lipoprotein-lipase, and the free fatty acids are supplied to the muscle and fat tissue. The remaining cholesterol-rich VLDL remnants are called intermediate density lipoproteins because of their higher density. Lipoprotein(a) (Lp(a)) has a density of 1.05 to 1.12 g/ml and resembles LDL in its composition. Besides apoprotein B-100, its protein portion consists of the apoprotein(a) which is characteristic of Lp(a). To date, very little is known about the physiology and function of the Lp(a). Since the apoprotein(a) molecule has a high sequence homology to plasminogen, it is assumed that Lp(a) both promotes the formation of thrombi on atherosclerotic plaques and also has an atherogenic effect. Lp(a) is found together with apoprotein B in atherosclerotic lesions. Retrospective studies have shown a correlation between increased Lp(a) and a CHD. Likewise, the metaanalysis of numerous prospective studies has shown that Lp(a) is an independent risk factor for the occurrence of a CHD. Levels of between 15 and 35 mg/dl are considered to be normal. So far, Lp(a) can be influenced neither by diet nor by medicaments. Therefore, therapy measures are restricted to reducing further risk factors. In particular, a lowering of the LDL cholesterol seems to lower the cardiovascular risk of Lp(a). In the pathogenesis of atherosclerosis, considerable pathophysiologic importance is, moreover, attributed to coagulation factors. Epidemiologic findings suggest a correlation between the fibrinogen concentration in plasma and the development of a coronary heart disease, and, primarily, a myocardial infarction. In this context, increased fibrinogen levels (>300 mg/dl) proved to be an independent indicator and risk factor for cardiovascular diseases. Yet also high concentrations of the tissue plasminogen activator inhibitor tPA-I are associated with the occurrence of CHD. The relationship between hyper-triglyceridemia and coronary risk is a different one in each case, depending on the cause of the elevation of the blood lipids. Despite the discussion whether or not triglycerides are to be considered as an independent risk factor it is undisputed that they play an important role in the pathogenesis of coronary heart diseases. Incidence of the disease is the highest in patients who exhibit high LDL cholesterol and a high triglyceride level.

The cholesterol ester transfer protein (CETP) is a stable plasma glycoprotein which is responsible for the transfer of neutral lipids and phospholipids between lipoproteins and which down-regulates the plasma concentration of HDL. The inhibition of the CETP lipid transfer activity has already been suggested as a therapeutic approach for increasing the HDL plasma level. There are numerous reasons which suggest that the reduction of CETP activity in plasma should lead to an increase in the HDL levels. Thus, CETP lowers the HDL concentration by the transfer of cholesterol esters from HDL to LDL and VLDL. In animal experiments with rabbits and hamsters, the transient inhibition of CETP with anti-CETP monoclonal antibodies, antisense oligonucleotides or CETP inhibitors led to the increase in the HDL levels. Lasting CETP inhibition with antisense oligonucleotides increased the HDL levels and, thus, led to a reduction of the atherosclerotic lesions in the rabbit animal model for atherosclerosis.

In the literature several CETP inhibitors are described, some of which are in clinical trials (e.g. Anacetrapib (Krishna R., Lancet 370 (9603) (2007): 1907-14) and Torcetrapib (Sikorski, J. A., J. Med. Chem. 49 (1) (2006): 1-22)).

In U.S. Pat. No. 5,512,548 and in WO 93/011782, polypeptides and their analogues are described which are capable of inhibiting CETP that catalyses the transfer of cholesterol esters from HDL to VLDL and LDL, and, therefore, have anti-atherosclerotic activity if administered to a patient. According to these documents, such a CETP polypeptide inhibitor is derived from apolipoprotein C-I of various sources, wherein especially N-terminal fragments up to amino acid 36 have been identified as CETP inhibitors.

Also in U.S. Pat. No. 5,880,095 A, a CETP-binding peptide is disclosed which is capable of inhibiting the activity of CETP in an individual. The CETP-inhibitory protein comprises an N-terminal fragment of porcine apolipoprotein C-III.

In the US 2006/0276400 and the WO 96/034888 peptides are disclosed, which are derived from CETP and comprise T-cell and/or B-cell epitopes. These peptides are able to induce in vivo the formation of CETP specific antibodies.

In US 2004/0087481 and U.S. Pat. No. 6,410,022 B1, peptides are disclosed which, because of the induction of a CETP-specific immune response, can be used for the treatment and prevention of cardiovascular diseases, such as, e.g., atheroslerosis. These peptides comprise a T helper cell epitope which is not derived from CETP, and at least one B-cell epitope that comes from CETP and can be derived directly from the latter. The T helper cell epitope advantageously is derived from tetanus toxoid and is covalently bound to at least one B-cell epitope of CETP. By using a T helper cell epitope that is alien to the organism, it becomes possible to induce antibodies in the body of an individual, which antibodies are directed against that peptide portion that consists of at least one CETP-B-cell epitope.

In Mao D et al (Vaccine 24 (2006): 4942-4950) the use of a plasmid comprising a nucleic acid molecule encoding for a B cell epitope of CETP as vaccine is described.

In the WO 2006/029982 CETP mimotopes to be used for the manufacture of a medicament for the treatment or prevention of atherosclerosis is described.

Most recently, there have already been suggestions for a vaccine approach with regard to CETP. Thus, e.g., rabbits have been treated with a vaccine which contained that peptide of CETP responsible for the cholesterol-ester transfer as an antigen. The immunized rabbits had a reduced CETP activity and altered lipoprotein levels with increased HDL and reduced LDL values. Moreover, the treated test animals of the atherosclerosis model also showed reduced atherosclerotic lesions in comparison with control animals.

The results of a phase II-clinical study were published, which study had been carried out by the American biotechnology company Avant with the vaccine CETi-1 (BioCentury Extra For Wednesday, Oct. 22, 2003). In this phase II-study, just as in the preceding phase I-study, a very good safety profile without any questionable side effects was proven, allowing the conclusion to be drawn that basically no side effects are to be expected from an anti-CETP vaccination approach. With regard to efficacy, however, the Avant vaccine was disappointing since it did not lead to increased HDL levels significantly better than those attained by a placebo treatment.

The problem with the CETi-1 vaccine is that it uses endogenous antigen. The human immune system is tolerant relative to endogenous structures, since with most of the endogenous molecules other than with CETP—it is vital that no autoantibodies be formed. Thus, it was the object of the CETi-1 vaccine to break the endogenous tolerance which, apparently, it has not achieved to a sufficient extent.

Thus, it is the object of the present invention to provide antigens for an anti-CETP vaccine which are selected such that they are considered as foreign by the immune system and therefore need not break a self-tolerance. These antigens may be used for preventing and/or treating atherosclerosis, atherosclerosis risk diseases and atherosclerosis sequelae.

Therefore the present invention relates to the use of a compound comprising the amino acid sequence $$(Z_1)_n X_1 X_2 X_3 X_4 (Z_2)_m,$$ (SEQ ID NO. 1)

wherein
$Z_1$ is an amino acid residue other than C,
$X_1$ is an amino acid residue selected from the group consisting of D, A, R, E, S, N, T and G,
$X_2$ is an amino acid residue selected from the group consisting of F, A, W, R, S, L, Q, V and M,
$X_3$ is an amino acid residue selected from the group consisting of L, A, S, W, E, R, I and H,
$X_4$ is an amino acid residue selected from the group consisting of Q, A, H, D, K, R, S and E,
$Z_2$ is an amino acid residue other than C,
n is an integer between 0 and 10, preferably between 0 and 9,
m is an integer between 0 and 3,
is not, or does not comprise, a 4- to 16-mer polypeptide fragment of the cholesterol ester transport protein (CETP) or a CETP-epitope, said compound having a binding capacity to an antibody which is specific for the natural CETP glycoprotein,
or
comprising an amino acid sequence selected from the group consisting of SYHATFL (SEQ ID NO. 2), TMAFPLN (SEQ ID NO. 3), HYHGAFL (SEQ ID NO. 4), EHHDIFL (SEQ ID NO. 5), TGLSVFL (SEQ ID NO. 6), WMPSLFY (SEQ ID NO. 7), SMPWWFF (SEQ ID NO. 8), TMPLLFW (SEQ ID NO. 9), DTWPGLE (SEQ ID NO. 10), SMPPIFY (SEQ ID NO. 11), MPLWWWD (SEQ ID NO. 12), SMPNLFY (SEQ ID NO. 13), RMPPIFY (SEQ ID NO. 14), NPFEVFL (SEQ ID NO. 15), TLPNWFW (SEQ ID NO. 16), SMPLTFY (SEQ ID NO. 17), SPHPHFL (SEQ ID NO. 18), NFMSIGL (SEQ ID NO. 19), SQFLASL (SEQ ID NO. 20), WSWPGLN (SEQ ID NO. 21), IAWPGLD (SEQ ID NO. 22), SKFMDTL (SEQ ID NO. 23), SMPMVFY (SEQ ID NO. 24), YEWVGLM (SEQ ID NO. 25), KGFLDHL (SEQ ID NO. 26), HQSDDK-MPWWFF (SEQ ID NO. 27), YVWQDPSFTTFF (SEQ ID NO. 28), YVWQDPSFTTFF (SEQ ID NO. 29), LPQTH-PLHLLED (SEQ ID NO. 30), GPVSIYADTDFL (SEQ ID NO. 31), DSNDTLTLAAFL (SEQ ID NO. 32), NGSPAL-SHMLFL (SEQ ID NO. 33), TDYDPMWVFFGY (SEQ ID NO. 34), IFPLDSQWQTFW (SEQ ID NO. 35), NESMPDL-FYQPS (SEQ ID NO. 36), DWGDKYFSSFWN (SEQ ID NO. 37), VSAYNNV (SEQ ID NO. 38) and WPLHLWQ (SEQ ID NO. 39) for producing a medicament for preventing and/or treating atherosclerosis, atherosclerosis risk diseases and atherosclerosis sequelae.

The present invention provides CETP mimotopes for these purposes. These mimotopes are able to induce antibodies which are able to inhibit CETP enzyme activity. The CETP mimotopes according to the present invention preferably are antigenic polypeptides which in their amino acid sequence vary from the amino acid sequence of CETP or of fragments of CETP. In this respect, the inventive mimotopes may comprise one or more non-natural amino acids (i.e. not from the 20 "classical" amino acids) or they may be completely assembled of such non-natural amino acids. Moreover, the inventive antigens which induce anti-CETP antibodies may be assembled of D- or L-amino acids or of combinations of DL-amino acids and, optionally, they may have been changed by further modifications, ring closures or derivatizations. Suitable anti-CETP-antibody-inducing antigens may be provided from commercially available peptide libraries. Preferably, these peptides are at least 4 amino acid residues in length, in particular at least 7 amino acids, and preferred lengths may be up to 16, preferably up to 14 or 20 amino acids (e.g. 5 to 16 amino acid residues). According to the invention, however, also longer peptides may very well be employed as anti-CETP-antibody-inducing antigens. Furthermore the mimotopes of the present invention may also be part of a polypeptide and consequently comprising at their N- and/or C-terminus at least one further amino acid residue.

The mimotopes of the present invention are capable to bind to antibodies which may be obtained by administration of C-FGFPEHLLVDFLQSLS (SEQ ID NO. 146) (16 C-terminal amino acids of CETP protein) coupled to KLH or other carriers to mammals. Once administered to a mammal the mimotopes are able to induce a corresponding immune response, so that antibodies directed against CETP are produced in said mammal.

The CETP-mimotopes (i.e. anti-CETP-antibody-inducing antigens) of the present invention can be identified and prepared by various methods, including phage libraries or peptide libraries. They can be produced and identified for instance by means of combinatorial chemistry or by means of high throughput screening techniques for the most varying structures (Display: A Laboratory Manual by Carlos F. Barbas (Editor), et al.; Willats WG Phage display: practicalities and prospects. Plant Mol. Biol. 2002; 50(6):837-54).

Furthermore, according to the invention also anti-CETP-antibody-inducing antigens based on nucleic acids ("aptamers") may be employed, and these, too, may be found with the most varying (oligonucleotide) libraries (e.g. with 2-180 nucleic acid residues) (e.g. Burgstaller et al., Curr. Opin. Drug Discov. Dev. 5(5) (2002), 690-700; Famulok et al., Acc. Chem. Res. 33 (2000), 591-599; Mayer et al., PNAS 98 (2001), 4961-4965, etc.). In anti-CETP-antibody-inducing antigens based on nucleic acids, the nucleic acid backbone can be provided e.g. by the natural phosphor-diester compounds, or also by phosphorotioates or combinations or chemical variations (e.g. as PNA), wherein as bases, according to the invention primarily U, T, A, C, G, H and mC can be employed. The 2'-residues of the nucleotides which can be used according to the present invention preferably are H, OH, F, Cl, NH$_2$, O-methyl, O-ethyl, O-propyl or O-butyl, wherein the nucleic acids may also be differently modified, i.e. for instance with protective groups, as they are commonly employed in oligonucleotide synthesis. Thus, aptamer-based anti-CETP-antibody-inducing antigens are also preferred anti-CETP-antibody-inducing antigens within the scope of the present invention.

According to the present invention the term "mimotope" refers to a molecule which has a conformation that has a topology equivalent to the epitope of which it is a mimic. The mimotope binds to the same antigen-binding region of an antibody which binds immunospecifically to a desired antigen. The mimotope will elicit an immunological response in a host that is reactive to the antigen to which it is a mimic. The mimotope may also act as a competitor for the epitope of which it is a mimic in in vitro inhibition assays (e.g. ELISA inhibition assays) which involve the epitope and an antibody binding to said epitope. However, a mimotope of the present invention may not necessarily prevent or compete with the binding of the epitope of which it is a mimic in an in vitro inhibition assay although it is capable to induce a specific immune response when administered to a mammal.

As used herein, the term "epitope" refers to an immunogenic region of an antigen which is recognized by a particular antibody molecule. In general, an antigen will possess one or more epitopes, each capable of binding an antibody that recognizes the particular epitope.

The abbreviations for the amino acid residues disclosed in the present invention follow the IUPAC recommendations:

| Amino Acid | 3-Letter Code | 1-Letter Code |
|---|---|---|
| Alanine | Ala | A |
| Arginine | Arg | R |
| Asparagine | Asn | N |
| Aspartic | Asp | D |
| Cysteine | Cys | C |
| Glutamic | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The mimotopes of the present invention can be synthetically produced by chemical synthesis methods which are well known in the art, either as an isolated peptide or as a part of another peptide or polypeptide. Alternatively, the peptide mimotope can be produced in a microorganism which produces the peptide mimotope which is then isolated and if desired, further purified. The peptide mimotope can be produced in microorganisms such as bacteria, yeast or fungi, in eukaryote cells such as a mammalian or an insect cells, or in a recombinant virus vector such as adenovirus, poxvirus, herpesvirus, Simliki forest virus, baculovirus, bacteriophage, sindbis virus or sendai virus. Suitable bacteria for producing the peptide mimotope include *E. coli, B. subtilis* or any other bacterium that is capable of expressing peptides such as the peptide mimotope. Suitable yeast types for expressing the peptide mimotope include *Saccharomyces cerevisiae, Schizosaccharomyces pombe, Candida, Pichia pastoris* or any other yeast capable of expressing peptides. Corresponding methods are well known in the art. Also methods for isolating and purifying recombinantly produced peptides are well known in the art and include e.g. as gel filtration, affinity chromatography, ion exchange chromatography etc.

To facilitate isolation of the peptide mimotope, a fusion polypeptide may be made wherein the peptide mimotope is translationally fused (covalently linked) to a heterologous polypeptide which enables isolation by affinity chromatography. Typical heterologous polypeptides are His-Tag (e.g. His$_6$; 6 histidine residues), GST-Tag (Glutathione-S-transferase) etc. The fusion polypeptide facilitates not only the purification of the mimotopes but can also prevent the mimotope polypeptide from being degraded during purification. If it is desired to remove the heterologous polypeptide after purification the fusion polypeptide may comprise a cleavage site at the junction between the peptide mimotope and the heterologous polypeptide. The cleavage site consists of an amino acid sequence that is cleaved with an enzyme specific for the amino acid sequence at the site (e.g. proteases).

The mimotopes of the present invention may also modified at or nearby their N- and/or C-termini so that at said positions a cysteine residue is bound thereto. In a preferred embodiment terminally positioned (located at the N- and C-termini of the peptide) cysteine residues are used to cyclize the peptides through a disulfide bond.

The mimotopes of the present invention may also be used in various assays and kits, in particular in immunological assays and kits. Therefore, it is particularly preferred that the mimotope may be part of another peptide or polypeptide, particularly an enzyme which is used as a reporter in immunological assays. Such reporter enzymes include e.g. alkaline phosphatase or horseradish peroxidase.

The term "atherosclerosis sequelae" or "sequelae of atherosclerosis" refers to the diseases which are a consequence of atherosclerose. These diseases include among others peripheral arterial occlusive disease, coronary heart disease and apoplectic cerebral insultus (see e.g. Steinberg D. J. Lipid Res. (2005) 46: 179-190; Steinberg D et al. J. Lipid Res (2006) 47: 1339-1351).

According to another preferred embodiment of the present invention $X_1$ is D and $X_4$ is Q or H, preferably Q. Such a molecule preferably comprises at its N-terminus further amino acid residues having the sequence $X_a X_b X_c X_d X_e X_f$ (SEQ ID NO. 41), wherein $X_a$ is P, Y, T or K, $X_b$ is an amino acid residue other than C, $X_c$ is H, $X_d$ is Y, L, H, V, T, I or F, $X_e$ is Y, I, P, L, Q, S, R, T, F or A and $X_f$ is A, W, V, Q, L, S, I, R or T.

According to a preferred embodiment of the present invention n is 7, 8 or 9, $Z_1$ is an amino acid residue other than C or selected from the group consisting of F, G, F, A, P, W, Y, S, G, D, L, E, K, T, P, I and M, preferably from the group consisting of F, G, F, A, P, Y, T, S, G, K and D, and $Z_2$ is selected from the group consisting of S, L, A, W, L, N, T, I, Y and H.

According to a further preferred embodiment of the present invention $X_1$ is selected from the group consisting of D, A, R, E and L, $X_2$ is selected from the group consisting of F, A, W, Q and R, $X_3$ is selected from the group consisting of L, A and S, and $X_4$ is selected from the group consisting of Q, A and H.

According to a preferred embodiment of the present invention $X_1$ is D, $X_2$ is selected from the group consisting of F, Q and W, $X_3$ is L or S and $X_4$ is Q or H.

According to a preferred embodiment of the present invention the compound comprises the amino acid sequence $FX_8(F)_oPX_9HX_{10}X_{11}X_{12}DX_2X_3X_4X_5X_6X_7$, (SEQ ID NO. 42)

wherein $X_8$ is selected from the group consisting of G, A, F, Y and K,
$X_9$ is selected from the group consisting of E, Y, A, Q, K and S,
$X_{10}$ is selected from the group consisting of H, V, L, F and I,
$X_{11}$ is selected from the group consisting of L, W, S, I, F and Y,
$X_{12}$ is V, T, F or I,
$X_5$ is S or Y,
$X_6$ is L, A or I,
$X_7$ is S, N or T, and
o is 0 or 1.

The compound of the present invention comprises preferably the amino acid sequence $X_1X_2X_3X_4X_5X_6X_7$ (SEQ ID NO. 43), wherein $X_1$ is selected from the group consisting of D, S, N, T and G, $X_2$ is F, $X_3$ is L, $X_4$ is selected from the group consisting of Q, D, K, R, S and E, $X_5$ is S or T, $X_6$ is L and $X_7$ is an amino acid residue other than C, preferably selected from the group consisting of S, T, A, M, F and W.

According to a preferred embodiment of the present invention the amino acid sequence is selected from the group consisting of SSLELFL (SEQ ID NO. 44), SFLDTLT (SEQ ID NO. 45), NFLKTLS (SEQ ID NO. 46), DFLRTLT (SEQ ID NO. 47), AFLDTLV (SEQ ID NO. 48), TFLSSLA (SEQ ID NO. 49), GFLDSLM (SEQ ID NO. 50), SPHPHFL (SEQ ID NO. 51), SNFLKTL (SEQ ID NO. 52), TGFLATL (SEQ ID NO. 53), SDFLRAL (SEQ ID NO. 54), SANPRDFLETLF (SEQ ID NO. 55), RMFPESFLDTLW (SEQ ID NO. 56), TIYDSFLDSLAS (SEQ ID NO. 57), KPYLLKDFLEAL (SEQ ID NO. 58), AMGPYDALDLFL (SEQ ID NO. 59), TWNPIESFLESL (SEQ ID NO. 60), QYQTPLTFLEAL (SEQ ID NO. 61), RHISPATFLEAL (SEQ ID NO. 62), HTDSFLSTFYGD (SEQ ID NO. 63), ADSTFTSFLQTL (SEQ ID NO. 64), GPVSIYADTDFL (SEQ ID NO. 65), DSNDTLTLAAFL (SEQ ID NO. 66), TPTHYYADFSQL (SEQ ID NO. 67), LPGHLIWDSLHY (SEQ ID NO. 68), LPQTHPLHLLED (SEQ ID NO. 69), IPYHHLVDQLHH (SEQ ID NO. 70), YPYHVQVDVLQN (SEQ ID NO. 71), IPSHHLQDSLQL (SEQ ID NO. 72), EYAHHTSLDLRQ (SEQ ID NO. 73), EPLHFRSDRIQA (SEQ ID NO. 74), ATPSHLIIDRAQ (SEQ ID NO. 75), APKHLYADMSQA (SEQ ID NO. 76), FKPAHVSIDWLQ (SEQ ID NO. 77), MPAHLSRDLRQS (SEQ ID NO. 78), NPKHYSIDRHQA (SEQ ID NO. 79), SPQHLTTDRAQA (SEQ ID NO. 80), TPFHFAQDSWQW (SEQ ID NO. 81), TPTHYYADFSQLLS (SEQ ID NO. 82), TPTHYYADFSQSLS (SEQ ID NO. 83), GTPTHYYADFSQLL (SEQ ID NO. 84), GTPTHYYADFSQSL (SEQ ID NO. 85), FGTPTHYYADFSQSLS (SEQ ID NO. 86), FGFPTHYYADFSQSLS (SEQ ID NO. 87), LPGHLIWDSLHY (SEQ ID NO. 88), LPGHLIWDSLHYL (SEQ ID NO. 89), LPGHLIWDSLHYLS (SEQ ID NO. 90), LPGHLIWDSLHSL (SEQ ID NO. 91), LPGHLIWDSLHSLS (SEQ ID NO. 92), GLPGHLIWDSLHYL (SEQ ID NO. 93), GLPGHLIWDSLHSL (SEQ ID NO. 94), FGLPGHLIWDSLHSLS (SEQ ID NO. 95), FGFPGHLIWDSLHSLS (SEQ ID NO. 96), LPQTHPLHLLED (SEQ ID NO. 97), IPYHHLVDQLHH (SEQ ID NO. 98), IPYHHLVDQLHLS (SEQ ID NO. 99), IPYHHLVDQLHSLS (SEQ ID NO. 100), FGIPYHHLVDQLHHLS (SEQ ID NO. 101), FGFPYHHLVDQLHSLS (SEQ ID NO. 102), YPYHVQVDVLQN (SEQ ID NO. 103), YPYHVQVDVLQNLS (SEQ ID NO. 104), YPYHVQVDVLQSLS (SEQ ID NO. 105), FGYPYHVQVDVLQNLS (SEQ ID NO. 106), FGFPYHVQVDVLQSLS (SEQ ID NO. 107), IPSHHLQDSLQL (SEQ ID NO. 108), IPSHHLQDSLQLLS (SEQ ID NO. 109), IPSHHLQDSLQSLS (SEQ ID NO. 110), GIPSHHLQDSLQLL (SEQ ID NO. 111), FGIPSHHLQDSLQLLS (SEQ ID NO. 112), FGFPSHHLQDSLQSLS (SEQ ID NO. 113), EYAHHTSLDLRQ (SEQ ID NO. 114), EPLHFRSDRIQA (SEQ ID NO. 115), EPLHFRSDRIQALS (SEQ ID NO. 116), EPLHFRSDRIQSLS (SEQ ID NO. 117), GEPLHFRSDRIQAL (SEQ ID NO. 118), FGEPLHFRSDRIQALS (SEQ ID NO. 119), FGFPLHFRSDRIQSLS (SEQ ID NO. 120), APKHLYADMSQA (SEQ ID NO. 121), APKHLYADMSQALS (SEQ ID NO. 122), APKHLYADMSQALS (SEQ ID NO. 123), GAPKHLYADMSQAL (SEQ ID NO. 124), FGFPKHLYADMSQSLS (SEQ ID NO. 125), MPAHLSRDLRQS (SEQ ID NO. 126), MPAHLSRDLRQSL (SEQ ID NO. 127), MPAHLSRDLRQSLS (SEQ ID NO. 128), GMPAHLSRDLRQSL (SEQ ID NO. 129), FGFPAHLSRDLRQSLS (SEQ ID NO. 130), NPKHYSIDRHQA (SEQ ID NO. 131), TPFHFAQDSWQW (SEQ ID NO. 132), TPFHFAQDSWQWLS (SEQ ID NO. 133), TPFHFAQDSWQSLS (SEQ ID NO. 134), GTPFHFAQDSWQWL (SEQ ID NO. 135), FGFPFHFAQDSWQSLS (SEQ ID NO. 136), ACSFAYLYRC (SEQ ID NO. 137), ACFMGDKWVC (SEQ ID NO. 138), ACVLYPKAIC (SEQ ID NO. 139), ACYMGQQFVC (SEQ ID NO. 140), ACLTAYLHWC (SEQ ID NO. 141), ACTLFPVAYC (SEQ ID NO. 142), ACWLFPYAHC (SEQ ID NO. 143), ACKSINMWLC (SEQ ID NO. 144), ACQTINRWLC (SEQ ID NO. 145), FGFPEHLLVDFLQSLS (SEQ ID NO. 146), FGFPEHLLVDFLQSLS (SEQ ID NO. 147), FPEHLLVDFLQSL (SEQ ID NO. 148), AGFPEHLLVDFLQSLS (SEQ ID NO. 149), FAFPEHLLVDFLQSLS (SEQ ID NO. 150), FGAPEHLLVDFLQSLS (SEQ ID NO. 151), FGFAEHLLVDFLQSLS (SEQ ID NO. 152), FGFPAHLLVDFLQSLS (SEQ ID NO. 153), FGFPEALLVDFLQSLS (SEQ ID NO. 154), FGFPEHALVDFLQSLS (SEQ ID NO. 155), FGFPEHLAVDFLQSLS (SEQ ID NO. 156), FGFPEHLLADFLQSLS (SEQ ID NO. 157), FGFPEHLLVAFLQSLS (SEQ ID NO. 158), FGFPEHLLVDALQSLS (SEQ ID NO. 159), FGFPEHLLVDFAQSLS (SEQ ID NO. 160), FGFPEHLLVDFLASLS (SEQ ID NO. 161), FGFPEHLLVDFLQALS (SEQ ID NO. 162), FGFPEHLLVDFLQSAS (SEQ ID NO. 163), FGFPEHLLVDFLQSLA (SEQ ID NO. 164), FAFPAHLLVDFLQALA (SEQ ID NO. 165), AAFPAHLLADFLQALA (SEQ ID NO. 166), SPQHLTTDRAQA (SEQ ID NO. 167), SPQHLTTDRAQALS (SEQ ID NO. 168), SPQHLTTDRAQSLS (SEQ ID NO. 169), GSPQHLTTDRAQAL (SEQ ID NO. 170), FGFPQHLTTDRAQSLS (SEQ ID NO. 171), FGFPQHLTTDWAQSLS (SEQ ID NO. 172), FGFPQHLTTDRLQSLS (SEQ ID NO. 173), FGFPQHLTTDWLQSLS (SEQ ID NO. 174), ATPSHLIIDRAQ (SEQ ID NO. 175), ATPSHLIIDRAQSLS (SEQ ID NO. 176), FGFPSHLIIDRAQSLS (SEQ ID NO. 177), FGFPSHLIIDWAQSLS (SEQ ID NO. 178), FGFPSHLIIDWLQSLS (SEQ ID NO. 179), FGFPSHLIIDWSQSLS (SEQ ID NO. 180), FATPSHLIIDWLQSLS (SEQ ID NO. 181), FKPAHVSIDWLQ (SEQ ID NO. 182), FKPAHVSIDWLQSLS (SEQ ID NO. 183), FGFPAHVSIDWLQSLS (SEQ ID NO. 184), AGFPAHVSIDWLQSLS (SEQ ID NO. 185), FAFPAHVSIDWLQSLS (SEQ ID NO. 186), FGAPAHVSIDWLQSLS (SEQ ID NO. 187), FGFAAHVSIDWLQSLS (SEQ ID NO. 188), FGFPAHVSADWLQSLS (SEQ ID NO. 189), FGFPAHVSIDWLQALS (SEQ ID NO. 190), FGFPAHVSIDWLQSLA (SEQ ID NO. 191), FAFPAHVSIDWLQALA (SEQ ID NO. 192), FGFAAHVSIDWLQSLS (SEQ ID NO. 193), FGFPAHVSIDWLQSLS (SEQ ID NO. 194), FGFPAHVSIR- WLQSLS (SEQ ID NO. 195), FGFPAHVSIEWLQSLS (SEQ ID NO. 196), FGFPAHVSIDWLNSLS (SEQ ID NO. 197), FGFPAHVSIDWLHSLS (SEQ ID NO. 198), AGFPAHVSIDWLQSLS (SEQ ID NO. 199), PGFPAHVSIDWLQSLS (SEQ ID NO. 200), WGFPAHVSIDWLQSLS (SEQ ID NO. 201), FAFPAHVSIDWLQSLS (SEQ ID NO. 202), FSFPAHVSIDWLQSLS (SEQ ID NO. 203), FYFPAHVSIDWLQSLS (SEQ ID NO. 204), FDFPAHVSIDWLQSLS (SEQ ID NO. 205), FGAPAHVSIDWLQSLS (SEQ ID NO. 206), FGFPAHVSIDWLQLLS (SEQ ID NO. 207), FGFPAHVSIDWLQWLS (SEQ ID NO. 208), FGFPAHVSIDWLQNLS (SEQ ID NO. 209), FGFPAHVSIDWLQTLS (SEQ ID NO. 210), FGFPAHVSIDWLQYLS (SEQ ID NO. 211), FGFPAHVSIDWLQSIS (SEQ ID NO. 212), FGFPAHVSIDWLQSLT (SEQ ID NO. 213), FGFPAHVSIDWLQSLY (SEQ ID NO. 214), FAFPAHVSIDWLQALA (SEQ ID NO. 215), FGFPAHVSIDRAQSLS (SEQ ID NO. 216), FGFPTHVSIDWLQSLS (SEQ ID NO. 217), FGFPFHVSIDWLQSLS (SEQ ID NO. 218), FGFPAHISIDWLQSLS (SEQ ID NO. 219), FGFPAHIIIDWLQSLS (SEQ ID NO. 220), FGFPAHLTTDWLQSLS (SEQ ID NO. 221), FGFPAHVFIDWLQSLS (SEQ ID NO. 222), FGFPAHVYIDWLQSLS (SEQ ID NO. 223), FGFPAHVSLDWLQSLS (SEQ ID NO. 224), FGFPAHVSADWLQSLS (SEQ ID NO. 225), TPTHYYADFSQSLS (SEQ ID NO. 226), FGFPAHVSIDWSQSLS (SEQ ID NO. 227), FGFPAHVSIDFSQSLS (SEQ ID NO. 228), FGFPSHIIIDWLQSLS (SEQ ID NO. 239), FGFPSHLIIEWLQSLS (SEQ ID NO. 240), AAFPAHLLADAAQALA (SEQ ID NO. 241), AAFPAHAAADFLQALA (SEQ ID NO. 242), AAFAAHLLADFLQAAA (SEQ ID NO. 243), AAAPAHLLVDAAQAAA (SEQ ID NO. 244), FAFPAHVFIDWLQSLS (SEQ ID NO. 245); FGFPAHVFIDWLQALS (SEQ ID NO. 246), FGFPAHVFIDWLQSLA (SEQ ID NO. 247), GFPAHVFIDWLQSLS (SEQ ID NO. 248), FPAHVFIDWLQSLS (SEQ ID NO. 249), PAHVFIDWLQSLS (SEQ ID NO. 250), FAFPAHVFIDWLQALA (SEQ ID NO. 251), FGFPEHLFVDFLQSLS (SEQ ID NO. 252), FGFPAHVHIDWLQSLS (SEQ ID NO. 253), FGFPAHVPIDWLQSLS (SEQ ID NO. 254), FGFPSHLFIDWAQSLS (SEQ ID NO. 255), PGFPAHVFIDWLQLIT (SEQ ID NO. 256), PAHVYIDWLQSLS (SEQ ID NO. 257), FGFPAHVYIDWLQ (SEQ ID NO. 258), FGFPAHVFIDWLQ (SEQ ID NO. 259), DFGFPSHLIIDWLQSLS (SEQ ID NO. 235), DFGFPAHVFIDWLQSLN (SEQ ID NO. 260), PSHLIIDWLQ (SEQ ID NO. 261), PAHVFIDWLQ (SEQ ID NO. 262), DFGFPAHVTIDWLQSLN (SEQ ID NO. 263), DFGFPAHVLIDWLQSLN (SEQ ID NO. 264), FGFPAHVFIDWLQSLN (SEQ ID NO. 230) and FGFPAHVFIDWLQSLA (SEQ ID NO. 265).

Particularly preferred mimotopes to be used according to the present invention are SANPRDFLETLF (SEQ ID NO. 55), RMFPESFLDTLW (SEQ ID NO. 56), SFLDTLT (SEQ ID NO. 45), NFLKTLS (SEQ ID NO. 46), DFLRTLT (SEQ ID NO. 47), TFLSSLA (SEQ ID NO. 49), GFLDSLM (SEQ ID NO. 50), FGFPYHVQVDVLQSLS (SEQ ID NO. 107), FGFPSHLIIDRAQSLS (SEQ ID NO. 177), FKPAHVSIDWLQSLS (SEQ ID NO. 183), FGFPAHVSIDWLQSLS (SEQ ID NO. 184), FGFPQHLTTDRAQSLS (SEQ ID NO. 171), FGFPTHYYADFSQSLS (SEQ IN NO. 87), FGFPGHLIWDSLHSLS (SEQ ID NO. 96), FGFPYHHLVDQLHSLS (SEQ ID NO. 102), FGFPSHHLQDSLQSLS (SEQ ID NO. 113), FGFPLHFRSDRIQSLS (SEQ ID NO. 120), FGFPKHLYADMSQSLS (SEQ ID NO. 125), FGFPAHLSRDLRQSLS (SEQ ID NO. 130) and FGFPFHFAQDSWQSLS (SEQ ID NO. 136).

Especially preferred mimotopes of the present invention are FGFPSHLIIDWLQSLS (SEQ ID NO. 179), FGFPAHV-FIDWLQSLS (SEQ ID NO. 222) and FGFPAHVYIDWLQSLS (SEQ ID NO. 223).

Further preferred mimotopes are FGFPAHVWIDWLQSLS (SEQ ID NO. 229), FGFPAHVFIDWLQSLN (SEQ ID NO. 230), FGFPAHFSIDWLQSLS (SEQ ID NO. 231), FGFPAHVSFDWLQSLS (SEQ ID NO. 232), FGFPEHVFIDWLQSLS (SEQ ID NO. 233), DFGFPAHVFIDWLQSLS (SEQ ID NO. 234), DFGFPSHLIIDWLQSLS (SEQ ID NO. 235), DFGFPAHVYIDWLQSLS (SEQ ID NO. 236), FGFPQHLFTDWLQSLS (SEQ ID NO. 237) and FGFPKHLLVDFLQSLS (SEQ ID NO. 238).

According to a preferred embodiment of the present invention the compound is coupled to a pharmaceutically acceptable carrier, preferably KLH (Keyhole Limpet Hemocyanin), tetanus toxoid, albumin-binding protein, bovine serum albumin, a dendrimer (MAP; Biol. Chem. 358: 581), peptide linkers (or flanking regions) as well as the adjuvant substances described in Singh et al., Nat. Biotech. 17 (1999), 1075-1081 (in particular those in Table 1 of that document), and O'Hagan et al., Nature Reviews, Drug Discovery 2 (9) (2003), 727-735 (in particular the endogenous immuno-potentiating compounds and delivery systems described therein), or mixtures thereof. The conjugation chemistry (e.g. via heterobifunctional compounds such as GMBS and of course also others as described in "Bioconjugate Techniques", Greg T. Hermanson) in this context can be selected from reactions known to the skilled man in the art. Moreover, the vaccine composition may be formulated with an adjuvant, preferably a low soluble aluminium composition, in particular aluminium hydroxide. Of course, also adjuvants like MF59 aluminium phosphate, calcium phosphate, cytokines (e.g., IL-2, IL-12, GM-CSF), saponins (e.g., QS21), MDP derivatives, CpG oligos, LPS, MPL, polyphosphazenes, emulsions (e.g., Freund's, SAF), liposomes, virosomes, iscoms, cochleates, PLG microparticles, poloxamer particles, virus-like particles, heat-labile enterotoxin (LT), cholera toxin (CT), mutant toxins (e.g., LTK63 and LTR72), microparticles and/or polymerized liposomes may be used.

The compound of the present invention is preferably bound to the carrier or adjuvant via a linker, which is selected from the group consisting of NHS-poly (ethylene oxide) (PEO) (e.g. NHS-PEO$_4$-maleimide).

A vaccine which comprises the present compound (mimotope) and the pharmaceutically acceptable carrier may be administered by any suitable mode of application, e.g. i.d., i.v., i.p., i.m., intranasally, orally, subcutaneously, etc. and in any suitable delivery device (O'Hagan et al., Nature Reviews, Drug Discovery 2 (9), (2003), 727-735). The compound of the present invention is preferably formulated for intravenous, subcutaneous, intradermal or intramuscular administration (see e.g. "Handbook of Pharmaceutical Manufacturing Formulations", Sarfaraz Niazi, CRC Press Inc, 2004).

Typically, the vaccine contains the compound according to the invention in an amount of from 0.1 ng to 10 mg, preferably 10 ng to 1 mg, in particular 100 ng to 100 µg, or, alternatively, e.g. 100 fmol to 10 µmol, preferably 10 pmol to 1 µmol, in particular 100 pmol to 100 nmol. Typically, the vaccine may also contain auxiliary substances, e.g. buffers, stabilizers etc.

Another aspect of the present invention relates to a peptide consisting of at least one amino acid sequence selected from the group consisting of SYHATFL (SEQ ID NO. 2), TMAFPLN (SEQ ID NO. 3), HYHGAFL (SEQ ID NO. 4), EHHDIFL (SEQ ID NO. 5), SSLELFL (SEQ ID NO. 44), TGLSVFL (SEQ ID NO. 6), WMPSLFY (SEQ ID NO. 7), SMPWWFF (SEQ ID NO. 8), TMPLLFW (SEQ ID NO. 9), DTWPGLE (SEQ ID NO. 10), SMPPIFY (SEQ ID NO. 11), MPLWWWD (SEQ ID NO. 12), SMPNLFY (SEQ ID NO.

13), RMPPIFY (SEQ ID NO. 14), NPFEVFL (SEQ ID NO. 15), TLPNWFW (SEQ ID NO. 16), SMPLTFY (SEQ ID NO. 17), SFLDTLT (SEQ ID NO. 45), NFLKTLS (SEQ ID NO. 46), DFLRTLT (SEQ ID NO. 47), AFLDTLV (SEQ ID NO. 48), TFLSSLA (SEQ ID NO. 49), GFLDSLM (SEQ ID NO. 50), SPHPHFL (SEQ ID NO. 51), NFMSIGL (SEQ ID NO. 19), SQFLASL (SEQ ID NO. 20), SNFLKTL (SEQ ID NO. 52), TGFLATL (SEQ ID NO. 53), WSWPGLN (SEQ ID NO. 21), IAWPGLD (SEQ ID NO. 22), SKFMDTL (SEQ ID NO. 23), SDFLRAL (SEQ ID NO. 54), SMPMVFY (SEQ ID NO. 24), YEWVGLM (SEQ ID NO. 25), KGFLDHL (SEQ ID NO. 26), SANPRDFLETLF (SEQ ID NO. 55), RMFPESFLDTLW (SEQ ID NO. 56), TIYDSFLDSLAS (SEQ ID NO. 57), HQSDDKMPWWFF (SEQ ID NO. 27), KPYLLKDFLEAL (SEQ ID NO. 58), AMGPYDALDLFL (SEQ ID NO. 59), TWNPIESFLESL (SEQ ID NO. 60), YVWQDPSFTTFF (SEQ ID NO. 28), QYQTPLTFLEAL (SEQ ID NO. 61), RHISPATFLEAL (SEQ ID NO. 62), HTDSFLSTFYGD (SEQ ID NO. 63), YVWQDPSFTTFF (SEQ ID NO. 29), ADSTFTSFLQTL (SEQ ID NO. 64), GPVSIYADTDFL (SEQ ID NO. 65), DSNDTLTLAAFL (SEQ ID NO. 66), NGSPALSHMLFL (SEQ ID NO. 33), TDYDPMWVFFGY (SEQ ID NO. 34), IFPLDSQWQTFW (SEQ ID NO. 35), NESMPDLFYQPS (SEQ ID NO. 36), DWGDKYFSSFWN (SEQ ID NO. 37), VSAYNNV (SEQ ID NO. 38), WPLHLWQ (SEQ ID NO. 39), TPTHYYADFSQL (SEQ ID NO. 67), LPGHLIWDSLHY (SEQ ID NO. 68), LPQTHPLHLLED (SEQ ID NO. 69), IPYHHLVDQLHH (SEQ ID NO. 70), YPYHVQVDVLQN (SEQ ID NO. 71), IPSHHLQDSLQL (SEQ ID NO. 72), EYAHHTSLDLRQ (SEQ ID NO. 73), EPLHFRSDRIQA (SEQ ID NO. 74), ATPSHLIIDRAQ (SEQ ID NO. 75), APKHLYADMSQA (SEQ ID NO. 76), FKPAHVSIDWLQ (SEQ ID NO. 77), MPAHLSRDLRQS (SEQ ID NO. 78), NPKHYSIDRHQA (SEQ ID NO. 79), SPQHLTTDRAQA (SEQ ID NO. 80), TPFHFAQDSWQW (SEQ ID NO. 81), TPTHYYADFSQLLS (SEQ ID NO. 82), TPTHYYADFSQSLS (SEQ ID NO. 83), GTPTHYYADFSQLL (SEQ ID NO. 84), GTPTHYYADFSQSL (SEQ ID NO. 85), FGTPTHYYADFSQSLS (SEQ ID NO. 86), FGFPTHYYADFSQSLS (SEQ ID NO. 87), LPGHLIWDSLHY (SEQ ID NO. 88), LPGHLIWDSLHYL (SEQ ID NO. 89), LPGHLIWDSLHYLS (SEQ ID NO. 90), LPGHLIWDSLHSL (SEQ ID NO. 91), LPGHLIWDSLHSLS (SEQ ID NO. 92), GLPGHLIWDSLHYL (SEQ ID NO. 93), GLPGHLIWDSLHSL (SEQ ID NO. 94), FGLPGHLIWDSLHSLS (SEQ ID NO. 95), FGFPGHLIWDSLHSLS (SEQ ID NO. 96), LPQTHPLHLLED (SEQ ID NO. 97), IPYHHLVDQLHH (SEQ ID NO. 98), IPYHHLVDQLHLS (SEQ ID NO. 99), IPYHHLVDQLHSLS (SEQ ID NO. 100), FGIPYHHLVDQLHHLS (SEQ ID NO. 101), FGFPYHHLVDQLHSLS (SEQ ID NO. 102), YPYHVQVDVLQN (SEQ ID NO. 103), YPYHVQVDVLQNLS (SEQ ID NO. 104), YPYHVQVDVLQSLS (SEQ ID NO. 105), FGYPYHVQVDVLQNLS (SEQ ID NO. 106), FGFPYHVQVDVLQSLS (SEQ ID NO. 107), IPSHHLQDSLQL (SEQ ID NO. 108), IPSHHLQDSLQLLS (SEQ ID NO. 109), IPSHHLQDSLQSLS (SEQ ID NO. 110), GIPSHHLQDSLQLL (SEQ ID NO. 111), FGIPSHHLQDSLQLLS (SEQ ID NO. 112), FGFPSHHLQDSLQSLS (SEQ ID NO. 113), EYAHHTSLDLRQ (SEQ ID NO. 114), EPLHFRSDRIQA (SEQ ID NO. 115), EPLHFRSDRIQALS (SEQ ID NO. 116), EPLHFRSDRIQSLS (SEQ ID NO. 117), GEPLHFRSDRIQAL (SEQ ID NO. 118), GEPLHFRSDRIQALS (SEQ ID NO. 119), FGEPLHFRSDRIQSLS (SEQ ID NO. 120), APKHLYADMSQA (SEQ ID NO. 121), APKHLYADMSQALS (SEQ ID NO. 122), APKHLYADMSQALS (SEQ ID NO. 123), GAPKHLYADMSQAL (SEQ ID NO. 124), FGFPKHLYADMSQSLS (SEQ ID NO. 125), MPAHLSRDLRQS (SEQ ID NO. 126), MPAHLSRDLRQSL (SEQ ID NO. 127), MPAHLSRDLRQSLS (SEQ ID NO. 128), GMPAHLSRDLRQSL (SEQ ID NO. 129), FGFPAHLSRDLRQSLS (SEQ ID NO. 130), NPKHYSIDRHQA (SEQ ID NO. 131), TPFHFAQDSWQW (SEQ ID NO. 132), TPFHFAQDSWQWLS (SEQ ID NO. 133), TPFHFAQDSWQSLS (SEQ ID NO. 134), GTPFHFAQDSWQWL (SEQ ID NO. 135), FGFPFHFAQDSWQSLS (SEQ ID NO. 136), ACSFAYLYRC (SEQ ID NO. 137), ACFMGDKWVC (SEQ ID NO. 138), ACVLYPKAIC (SEQ ID NO. 139), ACYMGQQFVC (SEQ ID NO. 140), ACLTAYLHWC (SEQ ID NO. 141), ACTLFPVAYC (SEQ ID NO. 142), ACWLFPYAHC (SEQ ID NO. 143), ACKSINMWLC (SEQ ID NO. 144), ACQTINRWLC (SEQ ID NO. 145), FGFPEHLLVDFLQSLS (SEQ ID NO. 146), FGFPEHLLVDFLQSLS (SEQ ID NO. 147), FPEHLLVDFLQSL (SEQ ID NO. 148), AGFPEHLLVDFLQSLS (SEQ ID NO. 149), FAFPEHLLVDFLQSLS (SEQ ID NO. 150), FGAPEHLLVDFLQSLS (SEQ ID NO. 151), FGFAEHLLVDFLQSLS (SEQ ID NO. 152), FGFPAHLLVDFLQSLS (SEQ ID NO. 153), FGFPEALLVDFLQSLS (SEQ ID NO. 154), FGFPEHALVDFLQSLS (SEQ ID NO. 155), FGFPEHLAVDFLQSLS (SEQ ID NO. 156), FGFPEHLLADFLQSLS (SEQ ID NO. 157), FGFPEHLLVAFLQSLS (SEQ ID NO. 158), FGFPEHLLVDALQSLS (SEQ ID NO. 159), FGFPEHLLVDFAQSLS (SEQ ID NO. 160), FGFPEHLLVDFLASLS (SEQ ID NO. 161), FGFPEHLLVDFLQALS (SEQ ID NO. 162), FGFPEHLLVDFLQSAS (SEQ ID NO. 163), FGFPEHLLVDFLQSLA (SEQ ID NO. 164), FAFPAHLLVDFLQALA (SEQ ID NO. 165), AAFPAHLLADFLQALA (SEQ ID NO. 166), SPQHLTTDRAQA (SEQ ID NO. 167), SPQHLTTDRAQALS (SEQ ID NO. 168), SPQHLTTDRAQALS (SEQ ID NO. 169), GSPQHLTTDRAQAL (SEQ ID NO. 170), FGFPQHLTTDRAQSLS (SEQ ID NO. 171), FGFPQHLTTDWAQSLS (SEQ ID NO. 172), FGFPQHLTTDRLQSLS (SEQ ID NO. 173), FGFPQHLTTDWLQSLS (SEQ ID NO. 174), ATPSHLIIDRAQ (SEQ ID NO. 175), ATPSHLIIDRAQSLS (SEQ ID NO. 176), FGFPSHLIIDRAQSLS (SEQ ID NO. 177), FGFPSHLIIDWAQSLS (SEQ ID NO. 178), FGFPSHLIIDWLQSLS (SEQ ID NO. 179), FGFPSHLIIDWSQSLS (SEQ ID NO. 180), FATPSHLIIDWLQSLS (SEQ ID NO. 181), FKPAHVSIDWLQ (SEQ ID NO. 182), FKPAHVSIDWLQSLS (SEQ ID NO. 183), FGFPAHVSIDWLQSLS (SEQ ID NO. 184), AGFPAHVSIDWLQSLS (SEQ ID NO. 185), FAFPAHVSIDWLQSLS (SEQ ID NO. 186), FGAPAHVSIDWLQSLS (SEQ ID NO. 187), FGFAAHVSIDWLQSLS (SEQ ID NO. 188), FGFPAHVSADWLQSLS (SEQ ID NO. 189), FGFPAHVSIDWLQALS (SEQ ID NO. 190), FGFPAHVSIDWLQSLA (SEQ ID NO. 191), FAFPAHVSIDWLQALA (SEQ ID NO. 192), FGFAAHVSIDWLQSLS (SEQ ID NO. 193), FGFAHVSIDWLQSLS (SEQ ID NO. 194), FGFPAHVSIRWLQSLS (SEQ ID NO. 195), FGFPAHVSIEWLQSLS (SEQ ID NO. 196), FGFPAHVSIDWLNSLS (SEQ ID NO. 197), FGFPAHVSIDWLHSLS (SEQ ID NO. 198), AGFPAHVSIDWLQSLS (SEQ ID NO. 199), PGFPAHVSIDWLQSLS (SEQ ID NO. 200), WGFPAHVSIDWLQSLS (SEQ ID NO. 201), FAFPAHVSIDWLQSLS (SEQ ID NO. 202), FSFPAHVSIDWLQSLS (SEQ ID NO. 203), FYFPAHVSIDWLQSLS (SEQ ID NO. 204), FDFPAHVSIDWLQSLS (SEQ ID NO. 205), FGAPAHVSIDWLQSLS (SEQ ID NO. 206), FGFPAHVSIDWLQLLS (SEQ ID NO. 207), FGFPAHVSIDWLQWLS (SEQ ID NO. 208), FGFPAHVSIDWLQNLS (SEQ ID NO. 209), FGFPAHVSIDWLQTLS (SEQ ID NO. 210), FGFPAHVSIDWLQYLS (SEQ ID NO. 211), FGFPAHVSIDWLQSIS (SEQ ID NO. 212), FGFPAHVSIDWLQSLT (SEQ ID NO. 213), FGFPAHVSIDWLQSLY (SEQ ID NO. 214), FAFPAHVSIDWLQALA (SEQ ID NO. 215), FGFPAHVSIDRAQSLS (SEQ ID NO. 216), FGFPTHVSIDWLQSLS (SEQ ID NO. 217), FGFPFHVSIDWLQSLS (SEQ ID NO. 218), FGFPAHISIDWLQSLS (SEQ ID NO. 219), FGFPAHIIIDWLQSLS (SEQ ID NO. 220), FGFPAHLTTDWLQSLS (SEQ ID NO. 221), FGFPAHVFIDWLQSLS (SEQ ID NO. 222), FGFPAHVYIDWLQSLS (SEQ ID NO. 223), FGFPAHVSLDWLQSLS (SEQ ID NO. 224), FGFPAHVSADWLQSLS (SEQ ID NO. 225), TPTHYYADFSQSLS (SEQ ID NO. 226), FGFPAHVWIDWLQSLS (SEQ ID NO. 229), FGFPAHVFIDWLQSLN (SEQ ID NO. 230), FGFPAHFSIDWLQSLS (SEQ ID NO. 231), FGFPAHVSFDWLQSLS (SEQ ID NO. 232), FGFPEHVFIDWLQSLS (SEQ ID NO. 233), DFGFPAHVFIDWLQSLS (SEQ ID NO. 234), DFGFPSHLIIDWLQSLS (SEQ ID NO. 235), DFGFPAHVYIDWLQSLS (SEQ ID NO. 236), FGFPQHLFTDWLQSLS (SEQ ID NO. 237), FGFPKHLLVDFLQSLS (SEQ ID NO. 238), FGFPAHVSIDWSQSLS (SEQ ID NO. 227), FGFPAHVSIDFSQSLS (SEQ ID NO. 228), FGFPSHIIIDWLQSLS (SEQ ID NO. 239), FGFPSHLIIEWLQSLS (SEQ ID NO. 240), AAFPAHLLADAAQALA (SEQ ID NO. 241), AAFPAHAAADFLQALA (SEQ ID NO. 242), AAFAAHLLADFLQAAA (SEQ ID NO. 243), AAAPAHLLVDAAQAAA (SEQ ID NO. 244), FAFPAHVFIDWLQSLS (SEQ ID NO. 245); FGFPAHVFIDWLQALS (SEQ ID NO. 246), FGFPAHVFIDWLQSLA (SEQ ID NO. 247), GFPAHVFIDWLQSLS (SEQ ID NO. 248), FPAHVFIDWLQSLS (SEQ ID NO. 249), PAHVFIDWLQSLS (SEQ ID NO. 250), FAFPAHVFIDWLQALA (SEQ ID NO. 251), FGFPEHLFVDFLQSLS (SEQ ID NO. 252), FGFPAHVHIDWLQSLS (SEQ ID NO. 253), FGFPAHVPIDWLQSLS (SEQ ID NO. 254), FGFPSHLFIDWAQSLS (SEQ ID NO. 255), PGFPAHVFIDWLQLIT (SEQ ID NO. 256), PAHVYIDWLQSLS (SEQ ID NO. 257), FGFPAHVYIDWLQ (SEQ ID NO. 258), FGFPAHVFIDWLQ (SEQ ID NO. 259), DFGFPAHVFIDWLQSLN (SEQ ID NO. 260), PSHLIIDWLQ (SEQ ID NO. 261), PAHVFIDWLQ (SEQ ID NO. 262), DFGFPAHVTIDWLQSLN (SEQ ID NO. 263), DFGFPAHVLIDWLQSLN (SEQ ID NO. 264), and FGFPAHVFIDWLQSLA (SEQ ID NO. 265).

The peptides of the present invention turned out to be mimotopes for CETP and, hence, the mimotopes were able to bind to antibodies binding to the CETP fragment C-FGFPEHLLVDFLQSLS (SEQ ID NO. 146) (16 C-terminal amino acids of CETP protein).

Yet, another aspect of the present invention relates to a pharmaceutical formulation comprising at least one peptide according to the present invention.

The peptides of the present invention may be formulated in a pharmaceutical formulation which may be administered to an individual. These formulations may be used, e.g., for preventing and/or treating atherosclerosis, atherosclerosis risk diseases and atherosclerosis sequelae.

The peptides in the formulation can be combined from the pool of peptides disclosed herein. Furthermore is also possible to provide pharmaceutical formulations, which comprise one or more of the peptides of the present invention, and which can be administered separately or together to an individual in need thereof.

The peptides of the present invention can be mixed into one single pharmaceutical formulation or in a combination of two or three. The resulting formulation can be administered at the same or the different moments in time. According to a preferred embodiment of the present invention the peptide present in the formulation is coupled to a pharmaceutically acceptable carrier, preferably KLH (Keyhole Limpet Hemocyanin).

The present invention is further illustrated by the following figures and examples, however, without being restricted thereto.

FIG. 1 shows the result of a representative competition ELISA after screening phage display library Ph.D. 7 with monoclonal antibody "Paula".

| Sequence | ID |
|---|---|
| FGFPEHLLVDFLQSLS | SEQ ID NO. 146 |
| FGFPEHLLVDFLQSLS | SEQ ID NO. 147 |
| SYHATFL | SEQ ID NO. 2 |
| TMAFPLN | SEQ ID NO. 3 |
| HYHGAFL | SEQ ID NO. 4 |
| EHHDIFL | SEQ ID NO. 5 |
| SSLELFL | SEQ ID NO. 44 |
| TGLSVFL | SEQ ID NO. 6 |
| WMPSLFY | SEQ ID NO. 7 |
| SMPWWFF | SEQ ID NO. 8 |
| TMPLLFW | SEQ ID NO. 9 |
| DTWPGLE | SEQ ID NO. 10 |
| SMPPIFY | SEQ ID NO. 11 |
| MPLWWWD | SEQ ID NO. 12 |
| SMPNLFY | SEQ ID NO. 13 |
| RMPPIFY | SEQ ID NO. 14 |
| NPFEVFL | SEQ ID NO. 15 |
| TLPNWFW | SEQ ID NO. 16 |

FIGS. 2a and 2b show the results of 2 typical competition ELISAs after screening phage display library Ph.D. 12 with monoclonal antibody "Paula".

| Sequence | ID |
|---|---|
| FGFPEHLLVDFLQSLS | SEQ ID NO. 146 |
| FGFPEHLLVDFLQSLS | SEQ ID NO. 147 |
| RHISPATFLEAL | SEQ ID NO. 62 |
| TIYDSFLDSLAS | SEQ ID NO. 57 |
| HTDSFLSTFYGD | SEQ ID NO. 63 |
| ADSTFTSFLQTL | SEQ ID NO. 64 |
| GPVSIYADTDFL | SEQ ID NO. 65 |
| DSNDTLTLAAFL | SEQ ID NO. 66 |
| NGSPALSHMLFL | SEQ ID NO. 33 |
| TDYDPMWVFFGY | SEQ ID NO. 34 |
| IFPLDSQWQTFW | SEQ ID NO. 35 |
| NESMPDLFYQPS | SEQ ID NO. 36 |
| DWGDKYFSSFWN | SEQ ID NO. 37 |

| | |
|---|---|
| HQSDDKMPWWFF | SEQ ID NO. 27 |
| KPYLLKDFLEAL | SEQ ID NO. 58 |
| SANPRDFLETLF | SEQ ID NO. 55 |
| RMFPESFLDTLW | SEQ ID NO. 56 |
| AMGPYDALDLFL | SEQ ID NO. 59 |
| TWNPIESFLESL | SEQ ID NO. 60 |
| YVWQDPSFTTFF | SEQ ID NO. 29 |
| QYQTPLTFLEAL | SEQ ID NO. 61 |

FIGS. 3a and 3b show the results of 2 representative competition ELISAs after screening phage display library Ph.D. 7 with mAb Frida.

| | |
|---|---|
| FGFPEHLLVDFLQSLS | SEQ ID NO. 146 |
| FGFPEHLLVDFLQSLS | SEQ ID NO. 147 |
| WPLHLWQ | SEQ ID NO. 39 |
| VSAYNNV | SEQ ID NO. 38 |

FIG. 4a shows the result of a representative competition ELISA after screening phage display library Ph.D. 12 with monoclonal antibody "Frida".

| | |
|---|---|
| FGFPEHLLVDFLQSLS | SEQ ID NO. 146 |
| FGFPEHLLVDFLQSLS | SEQ ID NO. 147 |
| TPTHYYADFSQL | SEQ ID NO. 67 |
| LPGHLIWDSLHY | SEQ ID NO. 68 |
| LPQTHPLHLLED | SEQ ID NO. 69 |

FIG. 4b shows binding of monoclonal antibody "Frida" to ELISA plates coated with mimotope-BSA FIGS. 5a and 5b show the results of a representative competition ELISA after screening phage display library Ph.D. 12 with monoclonal antibody "Frida".

| | |
|---|---|
| FGFPEHLLVDFLQSLS | SEQ ID NO. 146 |
| FGFPEHLLVDFLQSLS | SEQ ID NO. 147 |
| GTPTHYYADFSQLL | SEQ ID NO. 84 |
| GTPTHYYADFSQSL | SEQ ID NO. 85 |
| FGTPTHYYADFSQSLS | SEQ ID NO. 86 |
| FGFPTHYYADFSQSLS | SEQ ID NO. 87 |
| GLPGHLIWDSLHYL | SEQ ID NO. 93 |
| GLPGHLIWDSLHSL | SEQ ID NO. 94 |
| FGLPGHLIWDSLHSLS | SEQ ID NO. 95 |
| FGFPGHLIWDSLHSLS | SEQ ID NO. 96 |
| FGIPYHHLVDQLHHLS | SEQ ID NO. 101 |
| FGFPYHHLVDQLHSLS | SEQ ID NO. 102 |
| FGYPYHVQVDVLQNLS | SEQ ID NO. 106 |
| FGFPYHVQVDVLQSLS | SEQ ID NO. 107 |
| GIPSHHLQDSLQLL | SEQ ID NO. 111 |
| FGIPSHHLQDSLQLLS | SEQ ID NO. 112 |
| FGFPSHHLQDSLQSLS | SEQ ID NO. 113 |
| GEPLHFRSDRIQAL | SEQ ID NO. 118 |
| FGEPLHFRSDRIQALS | SEQ ID NO. 119 |
| FGFPLHFRSDRIQSLS | SEQ ID NO. 120 |
| ATPSHLIIDRAQSLS | SEQ ID NO. 176 |
| FGFPSHLIIDRAQSLS | SEQ ID NO. 177 |
| GAPKHLYADMSQAL | SEQ ID NO. 124 |
| FGFPKHLYADMSQSLS | SEQ ID NO. 125 |
| FKPAHVSIDWLQSLS | SEQ ID NO. 183 |
| FGFPAHVSIDWLQSLS | SEQ ID NO. 184 |
| GMPAHLSRDLRQSL | SEQ ID NO. 129 |
| FGFPAHLSRDLRQSLS | SEQ ID NO. 130 |
| GSPQHLTTDRAQAL | SEQ ID NO. 170 |
| FGFPQHLTTDRAQSLS | SEQ ID NO. 171 |
| GTPFHFAQDSWQWL | SEQ ID NO. 135 |
| FGFPFHFAQDSWQSLS | SEQ ID NO. 136 |

FIG. 6 shows the results of a competition ELISA of two mimotopes after screening phage display library Ph.D. 12 with monoclonal antibody "Frida".

| | |
|---|---|
| FGFPEHLLVDFLQSLS | SEQ ID NO. 146 |
| FGFPEHLLVDFLQSLS | SEQ ID NO. 147 |
| FGFPSHLIIDWAQSLS | SEQ ID NO. 178 |
| FGFPSHLIIDWLQSLS | SEQ ID NO. 179 |

FIGS. 7a to 7d show the antibody titer (anti mouse IgG) of in vivo experiments, whereby the following mimotope-BSA conjugates were injected into mice:

| | |
|---|---|
| Fr12/3/26/65 ext4 C-FGFPYHVQVDVLQSLS (SEQ ID NO. 107) | p4286 |
| Fr12/3/55 ext2 C-FGFPSHLIIDRAQSLS (SEQ ID NO. 177) | p4294 |
| Fr12/3/55 ext2 W instead of R C-FGFPSHLIIDWAQSLS (SEQ ID NO. 178) | p4324 |
| Fr12/3/55 ext2 WL instead of RA C-FGFPSHLIIDWLQSLS (SEQ ID NO. 179) | p4325 |
| Fr12/3/84 ext2 C-FGFPAHVSIDWLQSLS (SEQ ID NO. 184) | p4298 |
| Fr12/3/40 ext4 C-FGFPQHLTTDRAQSLS (SEQ ID NO. 171) | p4302 |
| Fr12/2/6 ext6 C-FGFPTHYYADFSQSLS (SEQ ID NO. 87) | p4278 |
| Fr12/2/11 ext7 C-FGFPGHLIWDSLHSLS (SEQ ID NO. 96) | p4282 |

-continued

| | | |
|---|---|---|
| Fr12/3/1/19/88 ext4 C-FGFPYHHLVDQLHSLS (SEQ ID NO. 102) | p4284 | |
| Fr12/3/68 ext5 C-FGFPSHHLQDSLQSLS (SEQ ID NO. 113) | p4289 | |
| Fr12/3/83 ext5 C-FGFPLHFRSDRIQSLS (SEQ ID NO. 120) | p4292 | |
| Fr12/3/63 ext4 C-FGFPKHLYADMSQSLS (SEQ ID NO. 125) | p4296 | |
| Fr12/3/47 ext4 C-FGFPAHLSRDLRQSL (SEQ ID NO. 130) | p4300 | |
| Fr12/3/35 ext4 C-FGFPFHFAQDSWQSLS (SEQ ID NO. 136) | p4304 | |

FIGS. 8a and 8b show the results of two representative competition ELISA after screening phage display library Ph.D. 7C7 with monoclonal antibody "Frida".

| | |
|---|---|
| FGFPEHLLVDFLQSLS | SEQ ID NO. 146 |
| FGFPEHLLVDFLQSLS | SEQ ID NO. 147 |
| ACSFAYLYRC | SEQ ID NO. 137 |
| ACYMGQQFVC | SEQ ID NO. 140 |
| ACLTAYLHWC | SEQ ID NO. 141 |
| ACTLFPVAYC | SEQ ID NO. 142 |
| ACWLFPYAHC | SEQ ID NO. 143 |
| ACQTINRWLC | SEQ ID NO. 145 |

FIG. 9 shows an in vitro ELISA test for the detection of the binding between "Frida" and cyclic mimotopes.

| | |
|---|---|
| FGFPEHLLVDFLQSLS | SEQ ID NO. 147 |
| ACSFAYLYRC | SEQ ID NO. 137 |
| ACYMGQQFVC | SEQ ID NO. 140 |
| ACLTAYLHWC | SEQ ID NO. 141 |
| ACTLFPVAYC | SEQ ID NO. 142 |
| ACWLFPYAHC | SEQ ID NO. 143 |
| ACQTINRWLC | SEQ ID NO. 145 |

FIGS. 10a and 10b show the results of an inhibition ELISA assay with FGFPSHLIIDWLQSLS (SEQ ID NO. 179), FGFPAHVFIDWLQSLS (SEQ ID NO. 222) and FGFPAHVYIDWLQSLS (SEQ ID NO. 223).

FIG. 10a (Coat 1 μM peptide. Detection αIgG1)

| Frida pept N° | | | 2.5 ng mAb Frida | |
|---|---|---|---|---|
| | | | 2 μg peptide | 20 μg peptide |
| | buffer only | — | 1.05 | 0.96 |
| p4073 | original epitope | C-FGFPEHLLVDFLQSLS | 0.44 | 0.1 |
| p1358 | irrelevant peptide | irrelevant peptide | 1.08 | 0.91 |
| p4361 | FGFPAHVFIDWLQSLS | Fr12/3/84 ext2 VSI ⇨ VFI | 0.82 | 0.16 |
| p4362 | FGFPAHVYIDWLQSLS | Fr12/3/84 ext2 VSI ⇨ VFI | 0.75 | 0.15 |

FIG. 10b (Coat 1 μM peptide. Detection αIgG1)

| Frida pept N° | | | 2.5 ng mAb Frida | |
|---|---|---|---|---|
| | | | 2 μg peptide | 20 μg peptide |
| | buffer only | — | 0.84 | 0.75 |
| p4073 | original epitope | C-FGFPEHLLVDFLQSLS | 0.64 | 0.15 |
| p1358 | irrelevant peptide | irrelevant peptide | 0.88 | 0.77 |
| p4325 | FGFPSHLIIDWLQSLS | Fr12/3/55 ext2 RA ⇨ WL | 0.42 | 0.1 |

-continued

| | |
|---|---|
| ACYMGQQFVC | SEQ ID NO. 140 |
| ACLTAYLHWC | SEQ ID NO. 141 |
| ACTLFPVAYC | SEQ ID NO. 142 |

FIG. 11 shows the in vivo induction of antibodies directed to CETP by mimotopes of the invention that are administered to mice. Balb/c mice/30 μg Peptide, 2 injections in 2 week intervals. S3=2 weeks after 3rd injection. Alum as adjuvant. Titers against original epitope (p4073) induced by injection of mimotopes. Well coating: 50 μl of 1 μM p4073-BSA or 1 μg/ml activated KLH. Detection: αIgG:

|  |  |  | injected peptide-BSA | original epitope-BSA | irrelevant peptide-BSA |
|---|---|---|---|---|---|
| group 1 | KLH | KLH |  | 2.040 | 400 |
| group 2 | original epitope | p4073-KLH |  | 8.600 | 10 |
| group 3 | C-FGFPQHLTTDWLQSLS (SEQ ID NO. 174) | p4369-KLH | 14.000 | 12.900 | 10 |
| group 4 | C-FGFPSHLIIDWAQSLS (SEQ ID NO. 178) | p4324-KLH | 12.570 | 7.600 | 10 |
| group 5 | C-FGFPSHLIIDWLQSLS (SEQ ID NO. 179) | p4325-KLH | 2.930 | 1.820 | 10 |
| group 6 | C-FGFPSHLIIDWSQSLS (SEQ ID NO. 180) | p4366-KLH | 4.700 | 3.600 | 10 |
| group 7 | C-FATPSHLIIDWLQSLS (SEQ ID NO. 181) | p4345-KLH | 8.380 | 1.270 | 10 |
| group 8 | C-FAFPAHVSIDWLQALA (SEQ ID NO. 186) | p4328-KLH | 10.100 | 2.740 | 400 |
| group 9 | C-PGFPAHVSIDWLQSLS (SEQ ID NO. 200) | p4340-KLH | 18.100 | 15.640 | 10 |
| group 10 | C-WGFPAHVSIDWLQSLS (SEQ ID NO. 201) | p4341-KLH | 10.350 | 5.500 | 10 |
| group 11 | C-FSFPAHVSIDWLQSLS (SEQ ID NO. 203) | p4342-KLH | 4.620 | 1.610 | 10 |
| group 12 | C-FYFPAHVSIDWLQSLS (SEQ ID NO. 204) | p4343-KLH | 5.580 | 2.900 | 10 |
| group 13 | C-FDFPAHVSIDWLQSLS (SEQ ID NO. 205) | p4344-KLH | 12.200 | 3.580 | 10 |
| group 14 | C-FGFPAHVSIDWLQLLS (SEQ ID NO. 207) | p4347-KLH | 12.000 | 9.160 | 10 |
| group 15 | C-FGFPAHVSIDWLQYLS (SEQ ID NO. 211) | p4351-KLH | 2.950 | 2.400 | 10 |
| group 16 | C-FGFPAHVSIDWLQSIS (SEQ ID NO. 212) | p4352-KLH | 19.680 | 12.070 | 10 |
| group 17 | C-FGFPAHVSIDWLQSLT (SEQ ID NO. 213) | p4353-KLH | 11.200 | 8.650 | 10 |
| group 18 | C-FGFPAHISIDWLQSLS (SEQ ID NO. 219) | p4358-KLH | 16.500 | 12.940 | 10 |
| group 19 | C-FGFPAHIIDWLQSLS (SEQ ID NO. 220) | p4359-KLH | 8.540 | 5.340 | 10 |
| group 20 | C-FGFPAHVFIDWLQSLS (SEQ ID NO. 222) | p4361-KLH | 17.940 | 9.530 | 10 |

FIGS. 12a and 12b show the in vivo induction of CETP specific antibodies by the administration of the mimotopes of the invention. Titers to p4073 and its correlation to titers to CETP of selected groups (which show high titers against p4073): gr.4, gr.9, gr.10, gr.14, gr.16-20/gr.1 (KLH), gr.2 (original epitope) as controls. Coating: recombinant GST-CETP or purified rabbit CETP, respectively:

FIG. 12a

|  |  |  | recombinant GST-CETP | rabbit CETP |
|---|---|---|---|---|
| group 1 | KLH | KLH/Alum | 0.35 | 0.19 |
| group 2 | original epitope | p4073-KLH/Alum | 1.49 | 1.25 |

-continued

|  |  |  | recombinant GST-CETP | rabbit CETP |
|---|---|---|---|---|
| group 3 | C-FGFPQHLTTDWLQSLS (SEQ ID NO. 174) | p4369-KLH/Alum | 0.45 | 0.21 |
| group 4 | C-FGFPSHLIIDWAQSLS (SEQ ID NO. 178) | p4324-KLH/Alum | 0.58 | 0.28 |
| group 9 | C-PGFPAHVSIDWLQSLS (SEQ ID NO. 200) | p4340-KLH/Alum | 0.49 | 0.21 |
| group 10 | C-WGFPAHVSIDWLQSLS (SEQ ID NO. 201) | p4341-KLH/Alum | 0.39 | 0.18 |
| group 14 | C-FGFPAHVSIDWLQLLS (SEQ ID NO. 207) | p4347-KLH/Alum | 0.35 | 0.2 |
| group 16 | C-FGFPAHVSIDWLQSIS (SEQ ID NO. 212) | p4352-KLH/Alum | 0.48 | 0.28 |
| group 17 | C-FGFPAHVSIDWLQSLT (SEQ ID NO. 213) | p4353-KLH/Alum | 0.57 | 0.39 |
| group 18 | C-FGFPAHISIDWIQSLS (SEQ ID NO. 219) | p4358-KLH/Alum | 0.68 | 0.58 |
| group 19 | C-FGFPAHIIDWLQSLS (SEQ ID NO. 220) | p4359-KLH/Alum | 0.79 | 0.54 |
| group 20 | C-FGFPAHVFIDWLQSLS (SEQ ID NO. 222) | p4361-KLH/Alum | 1.64 | 1.51 |

FIG. 12b

|  |  |  | recombinant GST-CETP | rabbit CETP |
|---|---|---|---|---|
| group 1 | KLH | KLH/Alum | 0.18 | 0.47 |
| group 2 | original epitope | p4073-KLH/Alum | 1.26 | 1.42 |
| group 5 | C-FGFPSHLIIDWLQSLS (SEQ ID NO. 179) | p4325-KLH/Alum | 0.59 | 0.85 |
| group 6 | C-FGFPSHLIIDWSQSLS (SEQ ID NO. 180) | p4366-KLH/Alum | 0.4 | 0.65 |
| group 7 | C-FATPSHLIIDWLQSLS (SEQ ID NO. 181) | p4345-KLH/Alum | 0.39 | 0.46 |
| group 8 | C-FAFPAHVSIDWLQALA (SEQ ID NO. 186) | p4328-KLH/Alum | 0.45 | 0.43 |
| group 11 | C-FSFPAHVSIDWLQSLS (SEQ ID NO. 203) | p4342-KLH/Alum | 0.38 | 0.41 |
| group 12 | C-FYFPAHVSIDWLQSLS (SEQ ID NO. 204) | p4343-KLH/Alum | 0.61 | 1.05 |
| group 13 | C-FDFPAHVSIDWLQSLS (SEQ ID NO. 205) | p4344-KLH/Alum | 0.35 | 0.43 |
| group 15 | C-FGFPAHVSIDWLQYLS (SEQ ID NO. 211) | p4351-KLH/Alum | 0.54 | 0.59 |

FIG. 13 shows the in vivo induction of antibodies directed to CETP by mimotopes of the invention that are administered to mice.

Sera of each group (5 Balb/c mice each) were combined, diluted 1:100 and tested on ELISA plates coated with recombinant GST-CETP or rabbit CETP, respectively. Detection of bound antibodies was with aIgG.

|  |  |  | recombinant GST-CETP | rabbit CETP |
|---|---|---|---|---|
| group 1 | KLH | KLH/Alum | 0.23 | 0.17 |
| group 2 | original epitope | p4073-KLH/Alum | 1.08 | 0.46 |
| group 3 | C-FGFAAHVSIDWLQSLS (SEQ ID NO. 188) | p4335-KLH/Alum | 0.26 | 0.14 |
| group 4 | C-FGFPAHVSIDWLQWLS (SEQ ID NO. 208) | p4348-KLH/Alum | 0.33 | 0.16 |
| group 5 | C-FGFPAHLTTDWLQSLS (SEQ ID NO. 221) | p4360-KLH/Alum | 0.4 | 0.23 |
| group 6 | C-FGFPAHVYIDWLQSLS (SEQ ID NO. 223) | p4362-KLH/Alum | 0.86 | 0.94 |
| group 7 | C-FGFPAHVSIDWLQSLY (SEQ ID NO. 214) | p4354-KLH/Alum | 0.29 | 0.23 |
| group 8 | C-FGFPAHVSIRWLQSLS (SEQ ID NO. 195) | p4337-KLH/Alum | 0.24 | 0.14 |

FIG. 14 shows a CETP activity assay, wherein 0.6 μl human serum (with endogenous CETP activity) is mixed with serum from wild-type mice (not containing CETP activity) vaccinated with KLH/Alum (negative control group), p4703-KLH/Alum (original CETP epitope), or p4361 (or p4362 or p 4325) mimotope, respectively. It could be demonstrated that the addition of 1.2 μl and 0.6 μl serum from p4361-KLH/Alum vaccinated mice completely inhibits CETP activity and the addition of 0.2 μl serum reduces significantly said activity in contrast to the addition of serum from mice vaccinated with KLH/Alum-control only or with the original epitope (p4073-KLH/Alum).

FGFPEHLLVDFLQSLS       SEQ ID NO. 146

FGFPAHVFIDWLQSLS       SEQ ID NO. 222

FGFPSHLIIDWLQSLS       SEQ ID NO. 179

FGFPEHLLVDFLQSLS       SEQ ID NO. 146

FGFPAHVFIDWLQSLS       SEQ ID NO. 222

Figure 17:
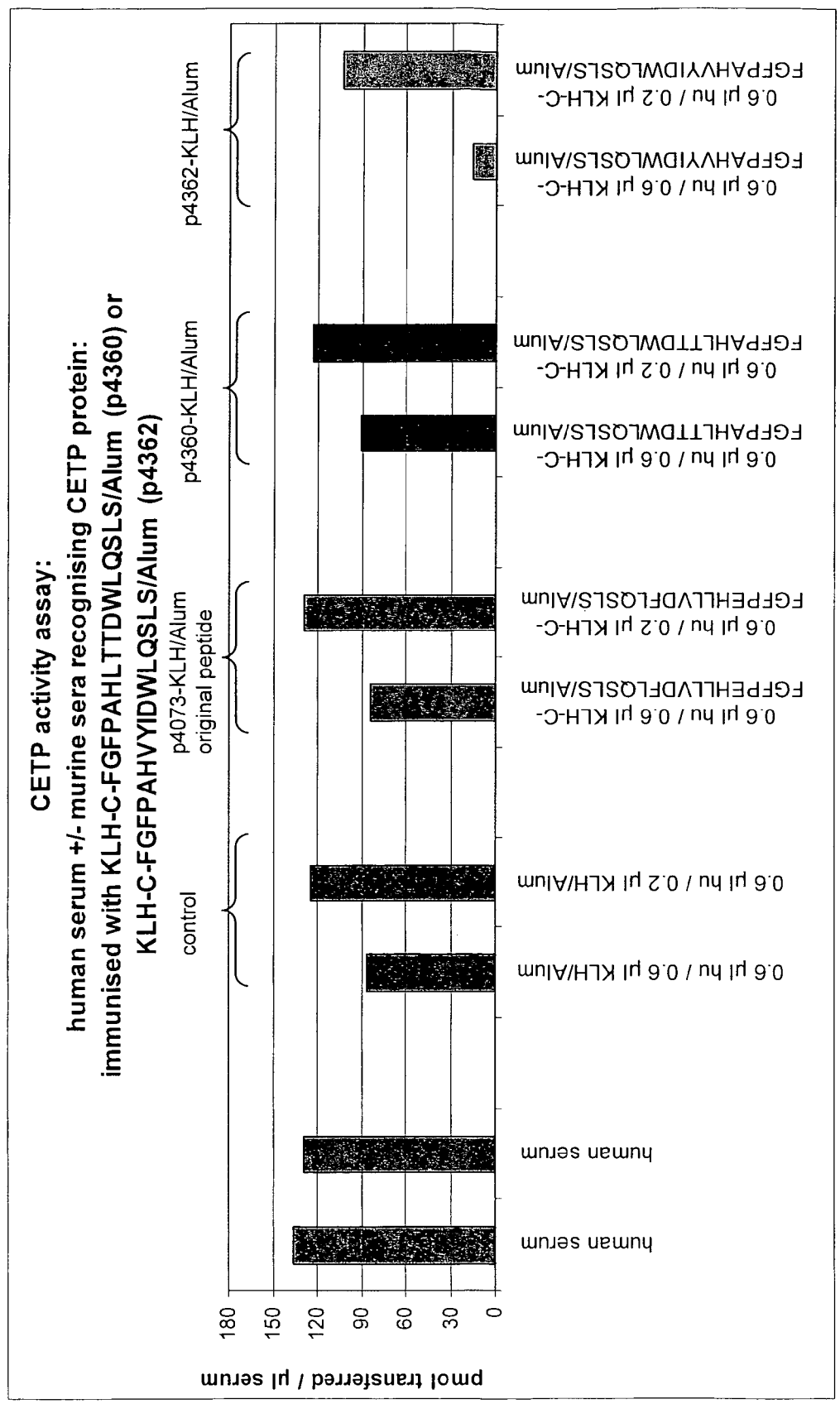

FIG. 17 shows that the addition of p4362-KLH/Alum to human serum inhibits significantly CETP activity.

FGFPEHLLVDFLQSLS       SEQ ID NO. 146

FGFPAHLTTDWLQSLS       SEQ ID NO. 221

FGFPAHVYIDWLQSLS       SEQ ID NO. 223

Figure 18A:
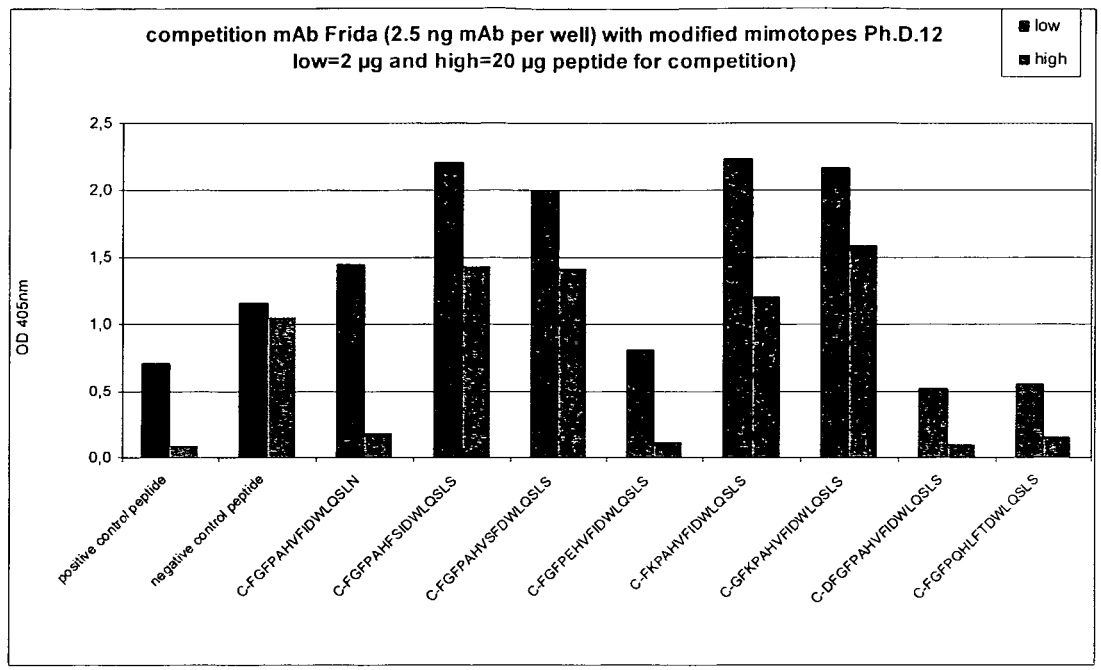

FIG. 18a shows an inhibition ELISA with mimotopes (Coat. 1 μM 4073 peptide, detection αIgG1).

| Frida | | | | 2.5 ng mAB Frida | |
|---|---|---|---|---|---|
| pept N° | | | | low | high |
| buffer only | buffer only | | buffer only | 1.084 | 1.079 |
| 4% DMSO | 4% DMSO | | 4% DMSO | 1.180 | 1.201 |
| p4073 | C-FGFPEHLLVDFLQSLS (SEQ ID NO. 147), positive control peptide | | p4073 | 0.537 | 0.094 |

-continued

| Frida pept N° | | | 2.5 ng mAB Frida low | high |
|---|---|---|---|---|
| p1208 | positive control peptide FGFPEHLLVDFLQSLS-C (SEQ ID NO. 146) | p1208 | 0.712 | 0.093 |
| p1358 | negative control peptide | p1358 | 1.158 | 1.050 |
| p4474 | C-PAHVYIDWLQSLS (SEQ ID NO. 257) | Fr12/3/84 ext2 VSIδVFI SLSδSLN | 1.452 | 0.179 |
| p4475 | C-FGFPAHFSIDWLQSLS (SEQ ID NO. 231) | Fr12/3/84 ext2 VSIδFSI | 2.211 | 1.429 |
| p4476 | C-FGFPAHVSFDWLQSLS (SEQ ID NO. 232) | Fr12/3/84 ext2 VSIδVSF | 2.000 | 1.417 |
| p4477 | C-FGFPEHVFIDWLQSLS (SEQ ID NO. 233) | Fr12/3/84 ext2 VSIδVFI PAHδPEH | 0.808 | 0.116 |
| p4478 | C-FKPAHVFIDWLQSLS (SEQ ID NO. 266) | Fr12/3/84 ext1 VSIδVFI | 2.231 | 1.206 |
| p4479 | C-GFKPAHVFIDWLQSLS (SEQ ID NO. 267) | Fr12/3/84 ext1 VSIδVFI plus G on N-terminus | 2.165 | 1.591 |
| p4480 | C-DFGFPAHVFIDWLQSLS (SEQ ID NO. 234) | Fr12/3/84 ext2 VSIδVFI plus D on N-terminus; =4361 plus D | 0.521 | 0.103 |
| p4481 | C-FGFPQHLFTDWLQSLS (SEQ ID NO. 237) | Fr12/3/40 ext4 RAδWL LTT/ LFT =p4369 with exchange TδF | 0.551 | 0.156 |

Figure 18B:
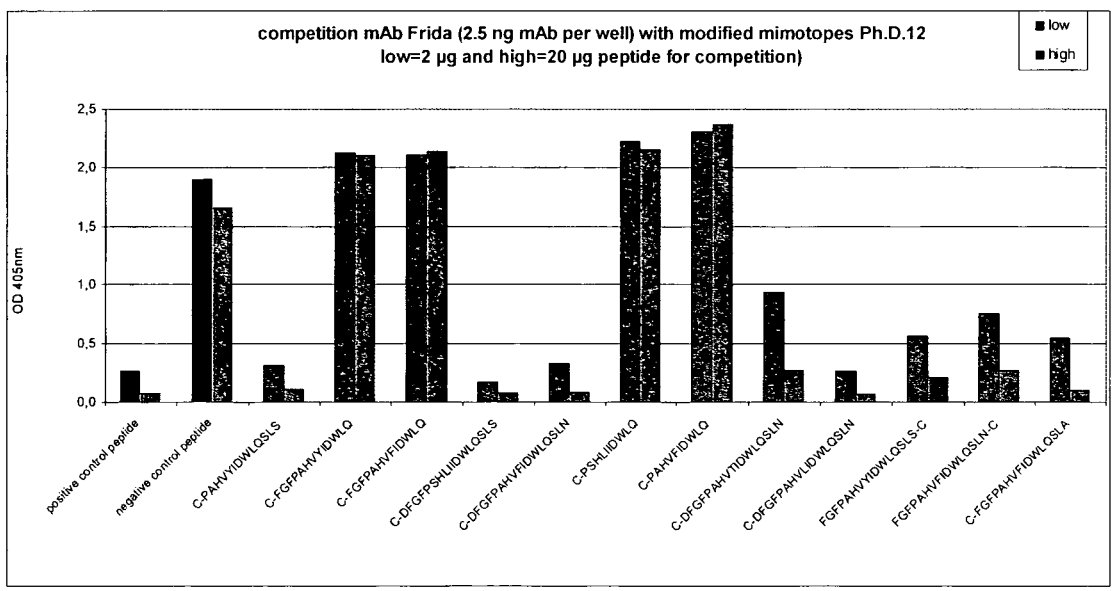

FIG. 18b shows an inhibition ELISA with mimotopes (Coat. 1 μM 4073 peptide, detection αIgG1).

| p1208 | positive control peptide | p1208 | 0.264 | 0.079 |
|---|---|---|---|---|
| p1358 | negative control peptide | p1358 | 1.902 | 1.661 |
| p4629 | C-PAHVYIDWLQSLS (SEQ ID NO. 257) | C-terminus of p4362; p4362 minus 3 aa on N-terminus | 0.313 | 0.118 |
| p4630 | C-FGFPAHVYIDWLQ (SEQ ID NO. 258) | N-terminus of p4362 (minus 3 aa on C-terminus) | 2.131 | 2.115 |
| p4631 | C-FGFPAHVFIDWLQ (SEQ ID NO. 259) | N-terminus of p4361 (minus 3 aa on C-terminus) | 2.111 | 2.147 |
| p4642 | C-DFGFPSHLIIDWLQSLS (SEQ ID NO. 235) | Fr12/3/55 ext2 RA → WL plus D; p4325 plus D on N-terminus | 0.171 | 0.082 |
| p4818 | C-DFGFPAHVFIDWLQSLN (SEQ ID NO. 260) | Fr12/3/84 ext2 VSI → VFI SLS → SLN plus D; =4361 N hinten plus D vorne | 0.332 | 0.091 |
| p4819 | C-PSHLIIDWLQ (SEQ ID NO. 261) | =4325 minus 3AA am N und am C-Terminus | 2.226 | 2.158 |

-continued

| | | | | |
|---|---|---|---|---|
| p4820 | C-PAHVFIDWLQ (SEQ ID NO. 262) | =4361 minus 3AA am N und am C-Terminus | 2.310 | 2.374 |
| p4989 | C-DFGFPAHVTIDWLQSLN (SEQ ID NO. 263) | Fr12/3/84 ext2 VSI → VTI; =p4361 F replaced by T, plus D on N-term and N instead of S on C-term | 0.932 | 0.274 |
| p4990 | C-DFGFPAHVLIDWLQSLN (SEQ ID NO. 264) | Fr12/3/84 ext2 VSI → VLI; =p4361 F replaced by L, plus D on N-term and N instead of S on C-term | 0.263 | 0.073 |
| p5067 | FGFPAHVYIDWLQSLS-C (SEQ ID NO. 223) | p4362 C on C-terminus | 0.563 | 0.217 |
| p5068 | FGFPAHVFIDWLQSLN-C (SEQ ID NO. 230) | p4474 C on C-terminus | 0.757 | 0.271 |

Figure 18C:
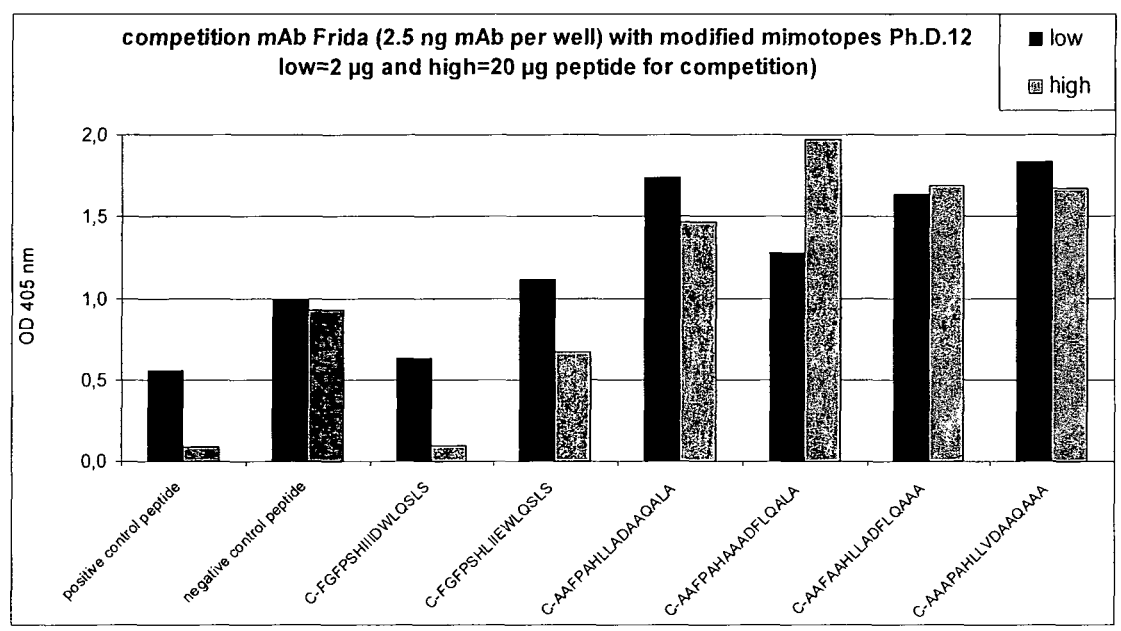

FIG. 18c shows a inhibition ELISA with mimotopes screen PhD12 Frida and Ala-exchange for mimotope characterisation/mAb Frida (Coat 1 μM 4073. Detection αIgG1.)

| Frida pept N° | | | 2.5 ng mAb Frida | |
|---|---|---|---|---|
| | | | low | high |
| | buffer only | buffer only | 0.964 | 0.964 |
| | 4% DMSO | 4% DMSO | 0.973 | 0.923 |
| | positive control peptide | p4073 | 0.554 | 0.088 |
| | p1208 | p1208 | 0.942 | 0.101 |
| | negative control peptide | p1358 | 0.986 | 0.93 |
| p4432 | C-FGFPSHIIIDWLQSLS (SEQ ID NO. 239) | Fr12/3/55 ext2exch2 L -> I | 0.635 | 0.096 |
| p4433 | C-FGFPSHLIIEWLQSLS (SEQ ID NO. 240) | Fr12/3/55 ext2exch2 D -> E | 1.114 | 0.672 |
| p4434 | C-AAFPAHLLADAAQALA (SEQ ID NO. 241) | Ala-exchange for mimotope characterisation | 1.74 | 1.461 |
| p4435 | C-AAFPAHAAADFLQALA (SEQ ID NO. 242) | Ala-exchange for mimotope characterisation | 1.281 | 1.969 |
| p4436 | C-AAFAAHLLADFLQAAA (SEQ ID NO. 243) | Ala-exchange for mimotope characterisation | 1.632 | 1.691 |
| p4437 | C-AAAPAHLLVDAAQAAA (SEQ ID NO. 244) | Ala-exchange for mimotope characterisation | 1.84 | 1.674 |

Figure 19A:
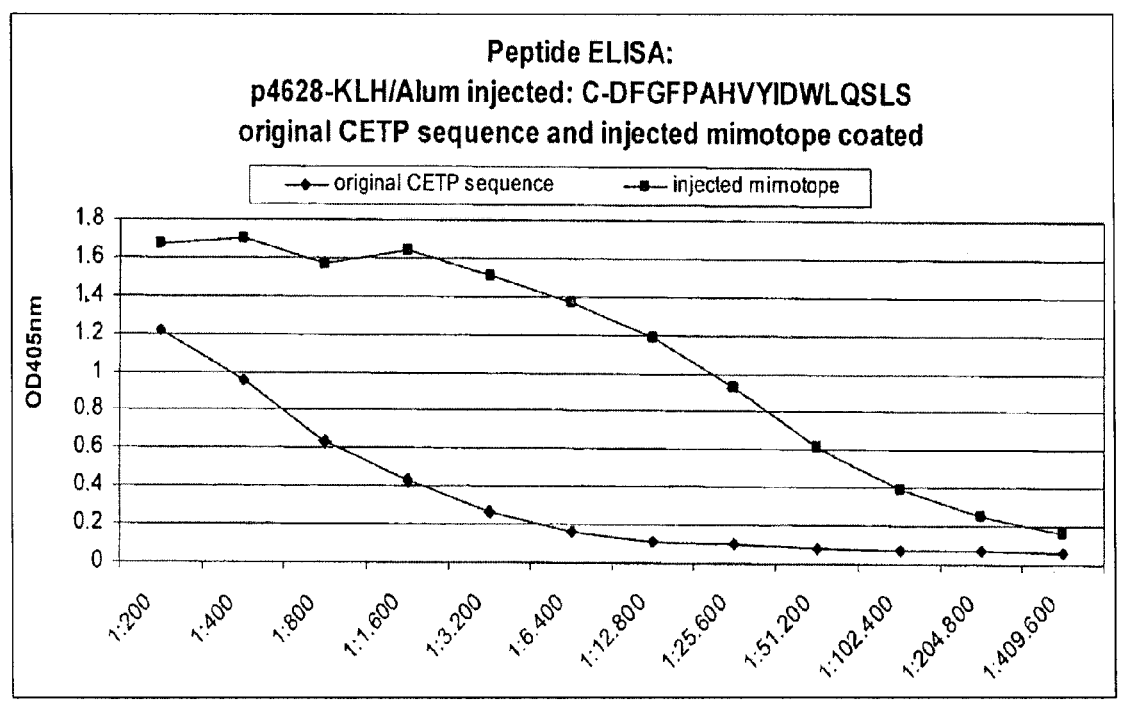

FIG. 19a shows a peptide ELISA, immunisation with C-DFGFPAHVYIDWLQSLS (p4628-KLH/Alum) (SEQ ID NO. 236), titre to original epitope.

Figure 19B:
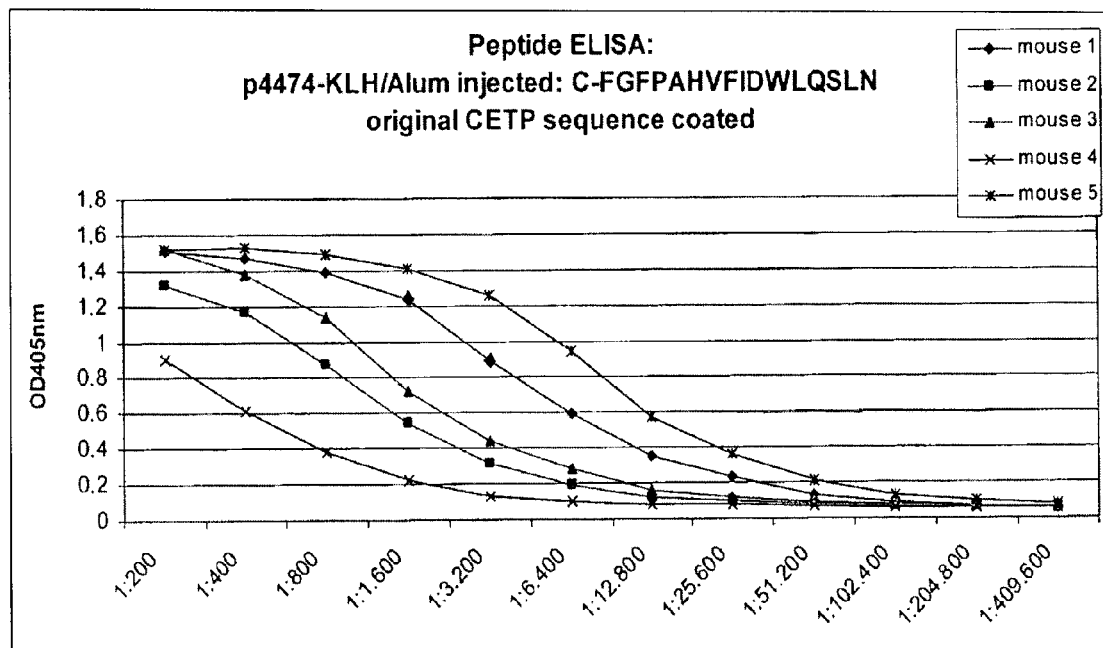

FIG. 19b shows a peptide ELISA, immunisation with C-FGFPAHVFIDWLQSLN (p4474-KLH/Alum) (SEQ ID NO. 230), titre to original epitope.

Figure 19C:
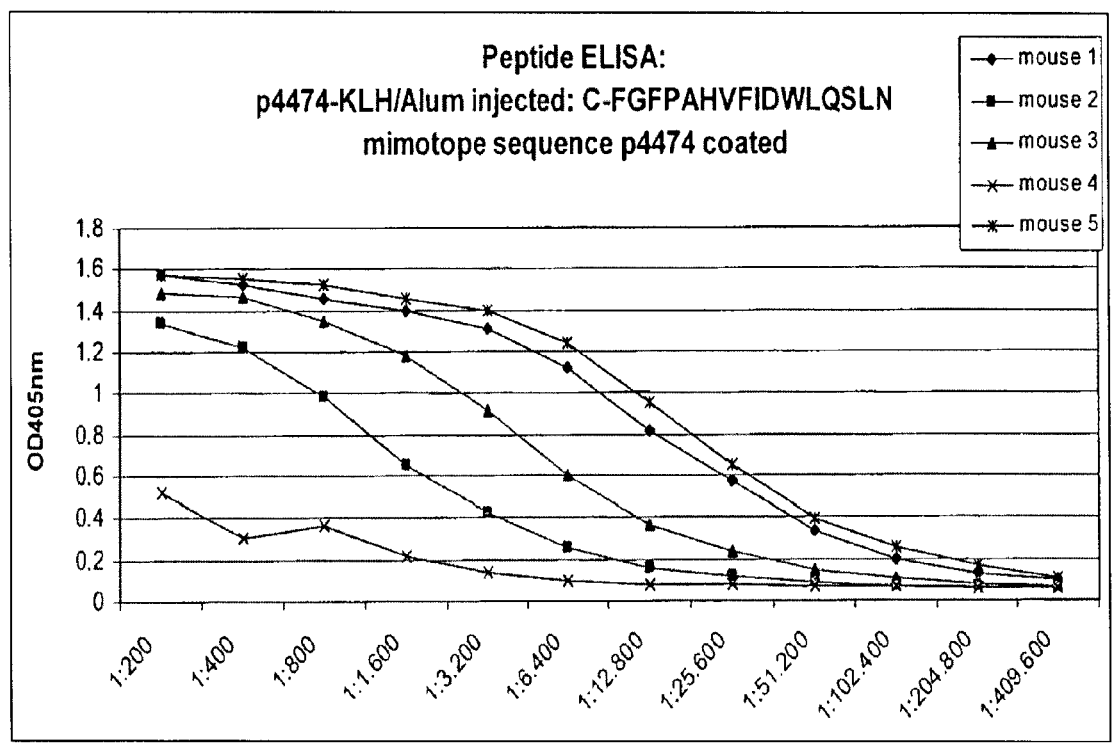

FIG. 19c shows a peptide ELISA, immunisation with C-FGFPAHVFIDWLQSLN (p4474-KLH/Alum) (SEQ ID NO. 230), titre to injected mimotope.

Figure 19D:
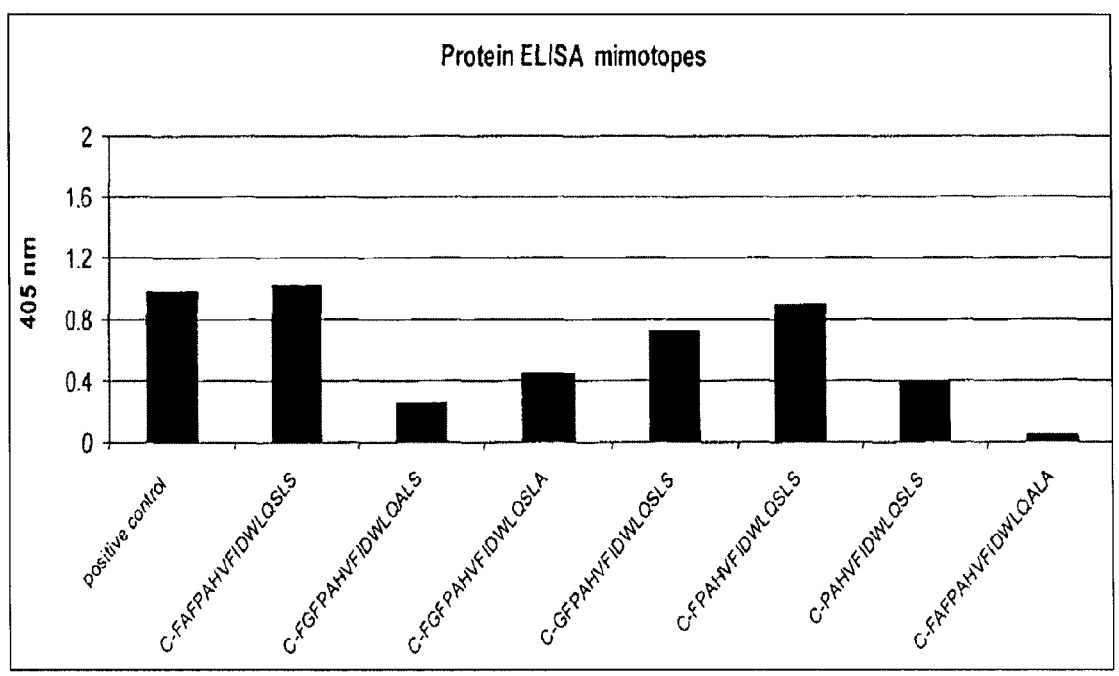

FIG. 19d shows an anti-protein ELISA. Mice were injected 3 times with 30 μg of the indicated mimotopes coupled to KLH with Alum as adjuvant. Sera from each group (comprising 5 mice) were pooled, diluted 1:100 and tested on ELISA plates coated with purified rabbit CETP.

| | |
|---|---|
| FAFPAHVFIDWLQSLS | SEQ ID NO. 245 |
| FGFPAHVFIDWLQALS | SEQ ID NO. 246 |

```
FGFPAHVFIDWLQSLA            SEQ ID NO. 247

GFPAHVFIDWLQSLS             SEQ ID NO. 248

FPAHVFIDWLQSLS              SEQ ID NO. 249

PAHVFIDWLQSLS               SEQ ID NO. 250

FAFPAHVFIDWLQALA            SEQ ID NO. 251
```

Figure 19E:
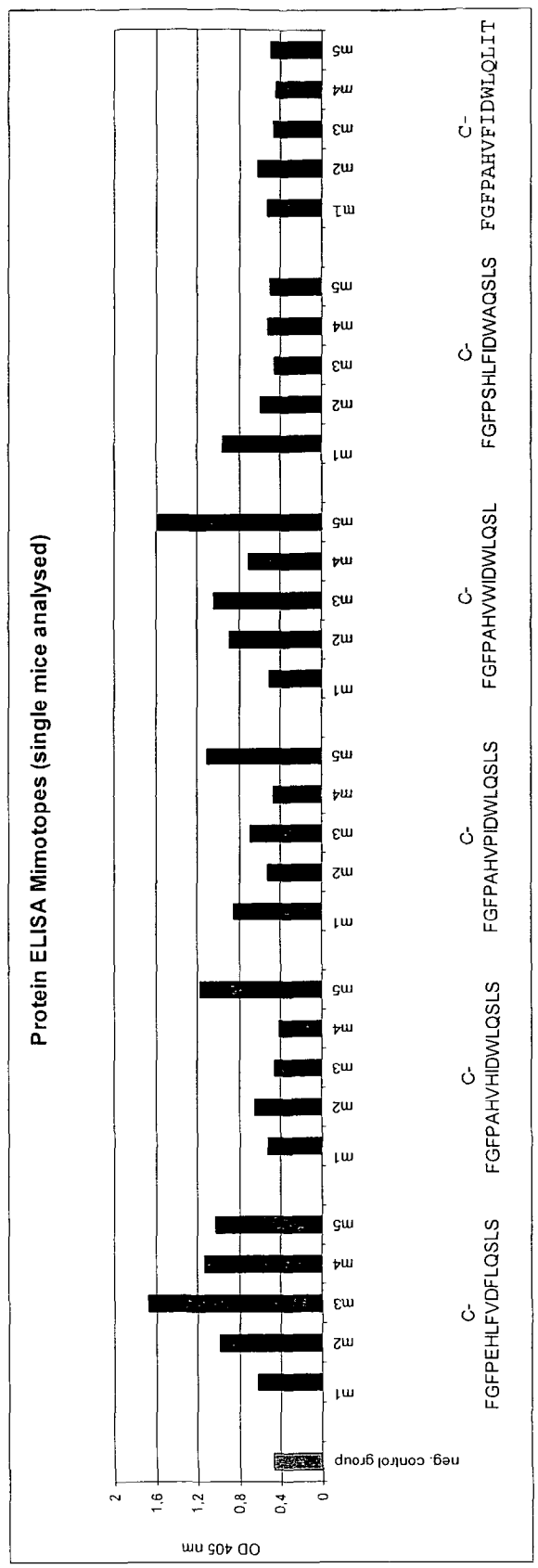

FIG. 19e shows an anti-protein ELISA, wherein mice were injected 3 times with 30 μg of the indicated mimotopes coupled to KLH with Alum as adjuvant. Mouse sera (from single mice) were diluted 1:100 and tested on ELISA plates coated with purified rabbit CETP.

```
FGFPEHLFVDFLQSLS            SEQ ID NO. 252

FGFPAHVHIDWLQSLS            SEQ ID NO. 253

FGFPAHVPIDWLQSLS            SEQ ID NO. 254

FGFPAHVWIDWLQSL             SEQ ID NO. 269

FGFPSHLFIDWAQSLS            SEQ ID NO. 255

FPGFPAHVFIDWLQLIT           SEQ ID NO. 268
```

EXAMPLES

There exists a strong inverse relationship between the plasma concentration of cholesterol in high density lipoproteins (HDLs) and the development of coronary heart disease (CHD). Thus, the risk for CHD is higher when HDLs decrease. Although 33% of patients with CHD have low plasma levels of HDLs, there is currently no effective therapy for increasing the plasma concentration of HDLs. Diet and moderate exercise are ineffective, statins only achieve a low 5 to 7% increase in HDL, and niacin has side effects and compliance profiles limiting its use.

The inhibition of CETP activity has been suggested as therapeutic approach to increase plasma HDL levels. CETP is a plasma glycoprotein that facilitates transfer of neutral lipids and phospholipids between lipoproteins and regulates the concentration of plasma HDL. The inhibition of CETP activity is expected to increase plasma HDL concentrations for several reasons. CETP lowers HDL concentrations by moving cholesteryl esters from HDLs to VLDLs and LDLs. Transient inhibition of CETP in rabbits and hamsters by monoclonal antibodies, small molecules (Sikorski, J. A., J. Med. Chem. 49 (1) (2006): 1-22), or antisense oligonucleotides causes HDL increase. Sustained CETP inhibition with antisense nucleotides increased plasma HDL and reduced atherosclerotic lesions in a rabbit model of atherosclerosis. CETP-transgenic mice and rats show decreased plasma HDL. Humans with reduced CETP activity have elevated plasma HDL.

Recently, a vaccine approach has been proposed. Rabbits were immunized with a human CETP-derived peptide containing a region of CETP critical for neutral lipid transfer function. Vaccinated rabbits had reduced CETP activity and an altered lipoprotein profile with lower LDL and higher HDL concentration. Furthermore, CETP-vaccinated rabbits were shown to have smaller atherosclerotic lesions than control animals.

The problem of the anti-CETP vaccine approach discussed above is that the vaccine formulation comprises a self peptide and therefore must break natural tolerance against self antigens. The invention describes a CETP mimotope that can be used for vaccination: The mimotope shall induce the production of antibodies against CETP. The CETP mimotope does not have a self sequence and therefore does not need to break tolerance. Thus, the induction of an anti-CETP antibody response is greatly facilitated. The mimotope is identified with a monoclonal antibody (mAb) and (commercially available) peptide libraries. An anti-CETP monoclonal antibody is used that neutralizes CETP activity. This mAb detects a sequence within the C-terminal 26 amino acids of CETP necessary for neutral lipid transfer activity.

Example 1

Generation of Monoclonal Antibodies to be Used for Screening of Phage Display Libraries A.) 2 Antibodies Derived from "Fusion F":
Balb/c mouse were immunized with original CETP epitope C-FGFPEHLLVDFLQSLS (SEQ ID NO. 147) (16 C-terminal amino acids of CETP protein) coupled to KLH and Alum as adjuvant.

2 hybridoma clones (both IgG1) were purified and used for screening: F5AF9G4 ("Paula") and F6F11D1 ("Felix").

These 2 monoclonal antibodies recognize the injected epitope as well as CETP protein in ELISA. They can also be used in Western Blot to detect CETP protein (recombinant protein expressed in bacteria as well as protein isolated from rabbit serum). Both antibodies do not inhibit CETP enzyme activity (tested with Roar CETP Activity Assay Kit, see e.g. U.S. Pat. No. 5,585,235; U.S. Pat. No. 5,618,683; U.S. Pat. No. 5,770,355).

B.) 2 Antibodies Derived from "Fusion I":
Balb/c mouse were immunized with original CETP epitope C-FGFPEHLLVDFLQSLS (SEQ ID NO. 147) (16 C-terminal amino acids of CETP protein) coupled to KLH and Alum as adjuvant.

2 hybridoma clones (both IgG1) were purified and used for screening: I2G6H5 ("Frida") and 12G6H7 ("James").

These 2 monoclonal antibodies recognize the injected epitope as well as CETP protein in ELISA. They can also be used in Western Blot to detect CETP protein (recombinant protein expressed in bacteria as well as protein isolated from rabbit serum). In contrast to the antibodies derived from "Fusion F" (see A.)) both antibodies "Frida" and "James" inhibit CETP enzyme activity (tested with Roar CETP Activity Assay Kit).

Example 2

Phage Display, In Vitro Inhibition ELISA and In Vivo Testing of Mimotopes

Phage Display libraries used in this example were:
Ph.D. 7: New England BioLabs E8102L (linear 7mer library)
Ph.D. C.7C: New England BioLabs E8121L (7mer library, cyclized peptides)
Ph.D. 12: New England BioLabs E8111L (linear 12mer library)

Phage Display was done according to manufacturer's protocol (www.neb.com).

After 2 or 3 subsequent rounds of panning, single phage clones were picked and phage supernatants were subjected to ELISA on plates coated with the antibody that was used for the panning procedure. Phage clones that were positive in this ELISA (strong signal for the target, but no signal for unspecific control) were sequenced. From DNA sequences, peptide sequences were deduced. These peptides were synthesized and characterised in inhibition ELISA.

1. In Vitro Inhibition Assay (ELISA)

Different amounts of peptides (2 and 20 µg, as indicated in the respective figures) derived from Phage Display were incubated with the monoclonal antibody that was used for the screening procedure. Peptides diminishing subsequent binding of the antibody to the original CETP epitope (C-terminal 16 amino acids of CETP protein) coated on ELISA plates were considered as inhibiting. (Results see i.a. FIGS. 19*a* to 19*c*)

2. In Vivo Testing of Mimotopes

Inhibiting as well as some non-inhibiting peptides were coupled to KLH and injected into mice (wildtype or CETP-transgenic mice; subcutaneously into the flank or intra-dermaly into the ears) or rabbits (subcutaneously into the flank) together with an appropriate adjuvant (aluminium hydroxide and Gerbu 100 for mice and aluminium hydroxide or CFA/IFA for rabbits).

Titers to injected peptides as well as to the original CETP epitope were determined. In addition, for selected sera also immune response to CETP protein was measured (Results see FIGS. 7*a* to 7*d* and FIGS. 19*a* to 19*e*).

3. Results 3.1. Screening with 2 Antibodies Derived from "Fusion F": "Paula" and "Felix"

3.1.1. Phage Display Library Ph.D. 7

3.1.1.1. Screening with Monoclonal Antibody "Paula"

17 Sequences were identified in this screen:

| | |
|---|---|
| P2_8 | SYHATFL (SEQ ID NO. 2) |
| P2_9 | TMAFPLN (SEQ ID NO. 3) |
| P2_11 | HYHGAFL (SEQ ID NO. 4) |
| P2_12 | EHHDIFL (SEQ ID NO. 5) |
| P2_15 | SSLELFL (SEQ ID NO. 44) |
| P2_16 | TGLSVFL (SEQ ID NO. 6) |
| P3_2 | WMPSLFY (SEQ ID NO. 7) |
| P3_6, 14, 28 | SMPWWFF (SEQ ID NO. 8) |
| P3_9 | TMPLLFW (SEQ ID NO. 9) |
| P3_13 | DTWPGLE (SEQ ID NO. 10) |
| P3_16 | SMPPIFY (SEQ ID NO. 11) |
| P3_17 | MPLWWWD (SEQ ID NO. 12) |
| P3_18 | SMPNLFY (SEQ ID NO. 13) |
| P3_19 | RMPPIFY (SEQ ID NO. 14) |
| P3_21 | NPFEVFL (SEQ ID NO. 15) |
| P3_25 | TLPNWFW (SEQ ID NO. 16) |
| P3_26 | SMPLTFY (SEQ ID NO. 17) |

The result of a representative competition ELISA is shown in FIG. 1.

3.1.1.2. Screening with Monoclonal Antibody "Felix"

6 sequences were identified that inhibit binding of monoclonal antibody "Felix" in in vitro competition experiments:

| | |
|---|---|
| F2-9 | C SFLDTLT (SEQ ID NO. 45) |
| F3-6 | C NFLKTLS (SEQ ID NO. 46) |
| F3-18 | C DFLRTLT (SEQ ID NO. 47) |
| F3-23 | C AFLDTLV (SEQ ID NO. 48) |
| F3-34 | C TFLSSLA (SEQ ID NO. 49) |
| F3-38 | C GFLDSLM (SEQ ID NO. 50) |

Additional 12 sequences were identified that do not inhibit binding of monoclonal antibody "Felix" in in vitro competition experiments:

| | |
|---|---|
| F2-2 + 5 | SPHPHFL (SEQ ID NO. 51) |
| F2-6 | NFMSIGL (SEQ ID NO. 19) |
| F2-16/F3-30 | SQFLASL (SEQ ID NO. 20) |
| F2-29 | SNFLKTL (SEQ ID NO. 52) |
| F3-1- | TGFLATL (SEQ ID NO. 53) |
| F3-11-_ | WSWPGLN (SEQ ID NO. 21) |
| F3-17- | IAWPGLD (SEQ ID NO. 22) |
| F3-32- | SKFMDTL (SEQ ID NO. 23) |
| F3-41- | SDFLRAL (SEQ ID NO. 54) |
| F3-44-_ | SMPMVFY (SEQ ID NO. 24) |
| F3-49- | YEWVGLM (SEQ ID NO. 25) |
| F3-64- | KGFLDHL (SEQ ID NO. 26 |

All mimotopes inhibiting the binding of monoclonal antibody "Felix" in vitro were coupled to KLH and injected subcutaneously (into the flank; s.c.) or intradermally (i.d.) into wild-type mice (mice do not have CETP protein), CETP-tg mice, or rabbits, respectively, and induced immune response to the injected peptide with all adjuvants that were tested (Alum and CFA (Complete Freund's adjuvant); Gerbu).

For all in vitro inhibiting mimotopes listed above, antibodies reacting to the original CETP epitope could be detected in mice and in rabbits.

For 5 out of 6 mimotopes (see below and Table 1) antibodies reacting with purified human CETP and recombinantly expressed human CETP could be detected in ELISAs from rabbit sera:

| | |
|---|---|
| F2-9 | C SFLDTLT (SEQ ID NO. 45) |
| F3-6 | C NFLKTLS (SEQ ID NO. 46) |
| F3-18 | C DFLRTLT (SEQ ID NO. 47) |
| F3-34 | C TFLSSLA (SEQ ID NO. 49) |
| F3-38 | C GFLDSLM (SEQ ID NO. 50) |

Subcutaneous injections in the flank were performed in week 1, week 3 and week 7 with 30 μg peptide-KLH per mouse. Intradermal injections in the ear were performed in week 1, week 3 and week 6 with 10 μg peptide-KLH per mouse. Sera were taken 2 weeks after the 3rd injection. Vaccine formulation with Alum (always 1 mg per mouse): up to 250 μl, injected into one flank. The Alum formulation with 1 ml per mouse (500 μl into each flank) was in 1×PBS as buffer.

Vaccine formulation with Gerbu Adjuvant 100 (Gerbu Cat. Nr. #3100; always 50 μl adjuvant per mouse): 200 μl, 100 μl injected into each flank comprising 1×HEPES as buffer.

TABLE 1

Results of the titer determination

| Adjuvant | | | KLH | injected P4073 mimotope (FGFPEHLLVDFLQSLS) | | p irrelevant |
|---|---|---|---|---|---|---|
| Alum s.c. (30 μg peptide) | KLH | | 1:20.000 | n.a. | 1:400 | no titer |
| | p4073-KLH | C-FGFPEHLLVDFLQSLS (SEQ ID NO. 147) | 1:70.000 | n.a. | 1:20.000 | no titer |
| | p4223-KLH | F2-9; C-SFLDTLT (SEQ ID NO. 45) | 1:15.000 | 1:15.000 | 1:6.400 | no titer |
| | p4181-KLH | F3-6 C-NFLKTLS (SEQ ID NO. 46) | 1:8.000 | 1:6.400 | 1:800 | no titer |
| | p4184-KLH | F3-18 C-DFLRTLT (SEQ ID NO. 47) | 1:5.000 | 1:10.000 | 1:3.000 | 1:2.500 |
| | p4187 | F3-34 C-TFLSSLA (SEQ ID NO. 49) | 1:3.200 | 1:9.000 | 1:4.000 | no titer |
| | p4188-KLH | F3-38 C-GFLDSLM (SEQ ID NO. 50) | 1:10.000 | 1:9.000 | 1.5.000 | no titer |
| | p4227-KLH | P12-19; C-SANPRDFLETLF (SEQ ID NO. 55) | 1:12.800 | 1:10.000 | 1:5.000 | no titer |
| | p4228-KLH | P12-21; C-RMFPESFLDTLW (SEQ ID NO. 56) | 1:10.000 | 1:4.000 | 1:1.000 | 1:400 |
| KLH/Gerbu s.c. (30 μg peptide) | KLH | | 1:70.000 | n.a. | 1:6.000 | 1:800 |
| | p4073-KLH | C-FGFPEHLLVDFLQSLS (SEQ ID NO. 147) | 1:25.000 | n.a. | 1:15.000 | 1:200 |
| | p4223-KLH | F2-9; C-SFLDTLT (SEQ ID NO. 45) | 1:40.000 | 1:25.000 | 1:50.000 | 1:1.000 |
| | p4181-KLH | F3-6 C-NFLKTLS (SEQ ID NO. 46) | 1:20.000 | 1.20.000 | 1:8.000 | 1:400 |
| | p4184-KLH | F3-18 C-DFLRTLT (SEQ ID NO. 47) | 1:27.000 | 1.35.000 | 1:15.000 | 1:6.000 |
| | p4187-KLH | F3-34 C-TFLSSLA (SEQ ID NO. 49) | 1.20.000 | 1.20.000 | 1:15.000 | no titer |
| | p4188-KLH | F3-38 C-GFLDSLM (SEQ ID NO. 50) | 1:40.000 | 1:35.000 | 1:35.000 | 1:400 |
| | p4227-KLH | P12-19; C-SANPRDFLETLF (SEQ ID NO. 55) | 1.20.000 | 1:30.000 | 1.3.000 | 1:400 |
| | p4228-KLH | P12-21; C-RMFPESFLDTLW (SEQ ID NO. 56) | 1:27.000 | 1:8.000 | 1:5.000 | no titer |
| | p4073-KLH | C-FGFPEHLLVDFLQSLS (SEQ ID NO. 147) | 1:10.000 | | 1:10.000 | no titer |

TABLE 1-continued

Results of the titer determination

| Adjuvant | | | KLH | injected mimotope (FGFPEHLLVDFLQSLS) | P4073 | p irrelevant |
|---|---|---|---|---|---|---|
| KLH/Alum i.d. (10 µg peptide) | KLH | | 1:12.800 | n.a. | no titer | no titer |
| | p4073-KLH | C-FGFPEHLLVDFLQSLS (SEQ ID NO. 147) | 1:10.000 | n.a. | 1:3.200 | no titer |
| | p4223-KLH | F2-9; C-SFLDTLT (SEQ ID NO. 45) | | 1:6.400 | 1:3.200 | |
| | p4181-KLH | F3-6 C-NFLKTLS (SEQ ID NO. 46) | 1:10.000 | 1:1.500 | 1:600 | no titer |
| | p4184-KLH | F3-18 C-DFLRTLT (SEQ ID NO. 47) | 1:15.000 | 1:5.000 | 1:1.500 | no titer |
| | p4187-KLH | F3-34 C-TFLSSLA (SEQ ID NO. 49) | 1:50.000 | 1:6.400 | 1:3.200 | 1:500 |
| | p4188-KLH | F3-38 C-GFLDSLM (SEQ ID NO. 50) | 1:12.000 | 1:5.000 | 1:2.000 | no titer |
| | p4227-KLH | P12-19; C-SANPRDFLETLF (SEQ ID NO. 55) | 1:6.400 | 1:6.400 | no titer | no titer |
| | p4228-KLH | P12-21; C-RMFPESFLDTLW (SEQ ID NO. 56) | 1:20.000 | 1:2.000 | 1:1.600 | no titer |
| | p4298-KLH | Fr12/3/84ext2; C-FGFPAHVSIDWLQSLS (SEQ ID NO. 184) | 1:25.000 | 1:3.200 | 1:1.600 | no titer |

3.1.2. Phage Display Library Ph.D. 12
3.1.2.1. Screening with Monoclonal Antibody "Paula"
Out of 20 amino acid sequences derived from this screen, 3 were inhibiting in in vitro inhibition experiments:

| P12-19 | SANPRDFLETLF (SEQ ID NO. 55) |
| P12-21 | RMFPESFLDTLW (SEQ ID NO. 56) |
| P12-37 | TIYDSFLDSLAS (SEQ ID NO. 57) |

Not inhibiting peptides were:

| P12-5/44/46/49 | HQSDDKMPWWFF (SEQ ID NO. 27) |
| P12-9 | KPYLLKDFLEAL (SEQ ID NO. 58) |
| P12-24/43-_ | AMGPYDALDLFL (SEQ ID NO. 59) |
| P12-25 | TWNPIESFLESL (SEQ ID NO. 60) |
| P12-28 + 42 | YVWQDPSFTTFF (SEQ ID NO. 28) |
| P12-30 | QYQTPLTFLEAL (SEQ ID NO. 61) |
| P12-35- | RHISPATFLEAL (SEQ ID NO. 62) |
| P12-39- | HTDSFLSTFYGD (SEQ ID NO. 63) |
| P12-42- | YVWQDPSFTTFF (SEQ ID NO. 29) |
| P12-45- | ADSTFTSFLQTL (SEQ ID NO. 64) |

-continued

| P12-50-_ | GPVSIYADTDFL (SEQ ID NO. 65) |
| P12-51-_ | DSNDTLTLAAFL (SEQ ID NO. 66) |
| P12-52-_ | NGSPALSHMLFL (SEQ ID NO. 33) |
| P12-53- | TDYDPMWVFFGY (SEQ ID NO. 34) |
| P12-56- | IFPLDSQWQTFW (SEQ ID NO. 35) |
| P12-58- | NESMPDLFYQPS (SEQ ID NO. 36) |
| P12-61- | DWGDKYFSSFWN (SEQ ID NO. 37) |

Figure 1:
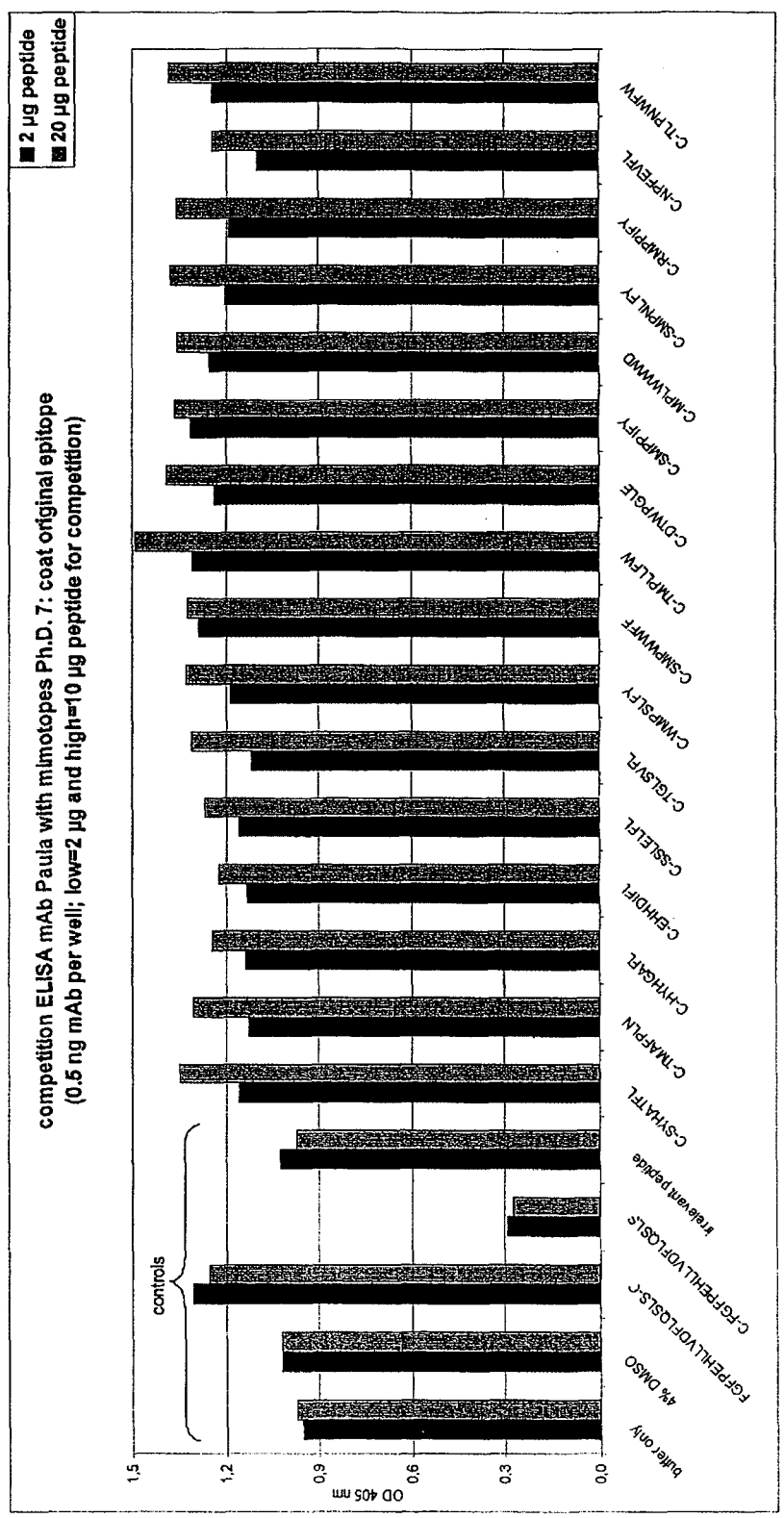
Figure 2A:
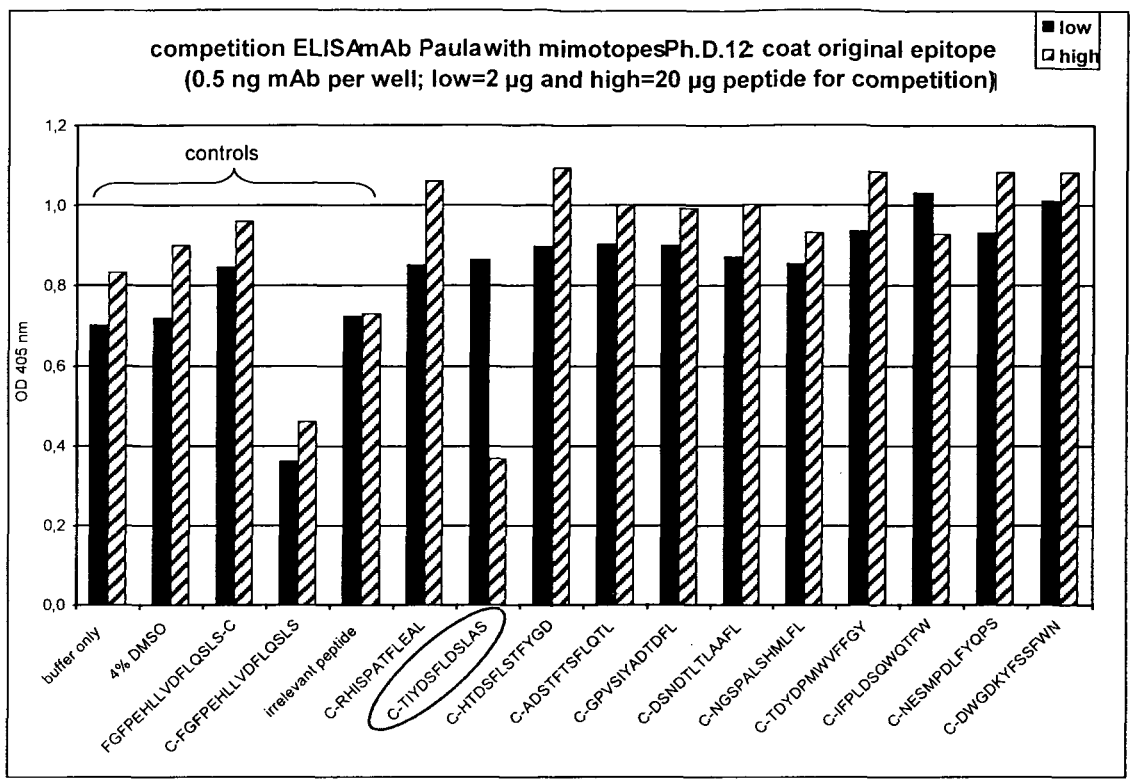
Figure 2B:
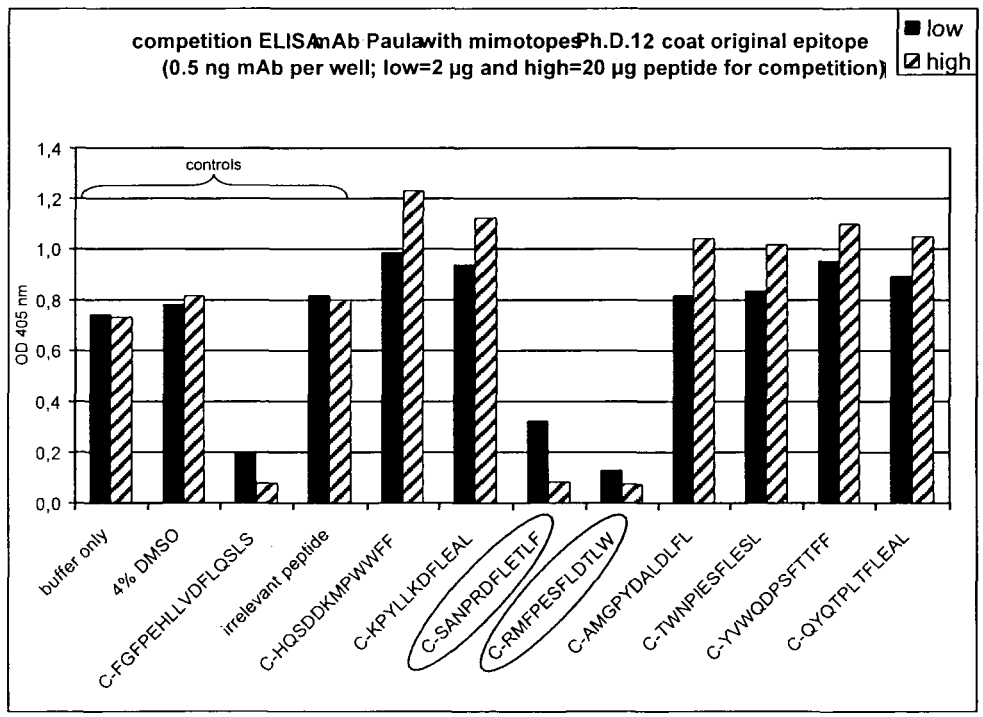

Results of 2 typical competition ELISAs are shown in FIGS. 2A and 2b.

All 3 mimotopes were coupled to KLH and injected into wildtype mice (mice do not have CETP protein), CETP-tg mice, or rabbits, respectively, and induced immune response to the injected peptide with all adjuvants that were tested (Alum and CFA; Gerbu).

Mimotope P12-19; C-SANPRDFLETLF (SEQ ID NO. 55) and P12-21; C-RMFPESFLDTLW (SEQ ID NO. 56) induced an immune response to the original CETP epitope in wt mice and in rabbits.

In contrast thereto, mimotope P12-37 C-TIYDSFLDSLAS (SEQ ID NO. 57) did not induce an antibody response to the original epitope.

3.2 Screening with 2 Antibodies Derived from "Fusion I": "Frida" and "James"
3.2.1. Phage Display Library Ph.D. 7
3.2.1.1. Screening with Monoclonal Antibodies "Frida" and "James"

Two different peptide sequences were identified in these screens, 11 of 12 clones that were sequenced had identical sequences. These peptides are not inhibiting in in vitro competition experiments.

```
Fr7-2-2

Fr7-2B-65

Fr7-3-7

Fr7-3-13

Fr7-3-26

Fr7-3-32

Ja7-2-22

Ja7-3-28

Ja7-3-41

Ja7-3-52

Ja7-3-56        VSAYNNV (SEQ ID NO. 38)

Ja7-3-89        WPLHLWQ (SEQ ID NO. 39)
```

Figure 3A:
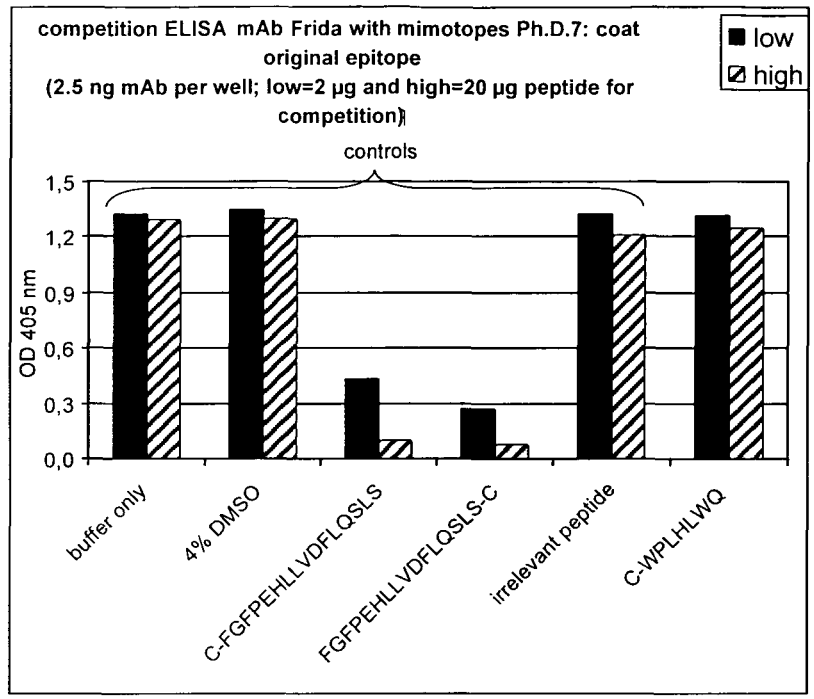
Figure 3B:
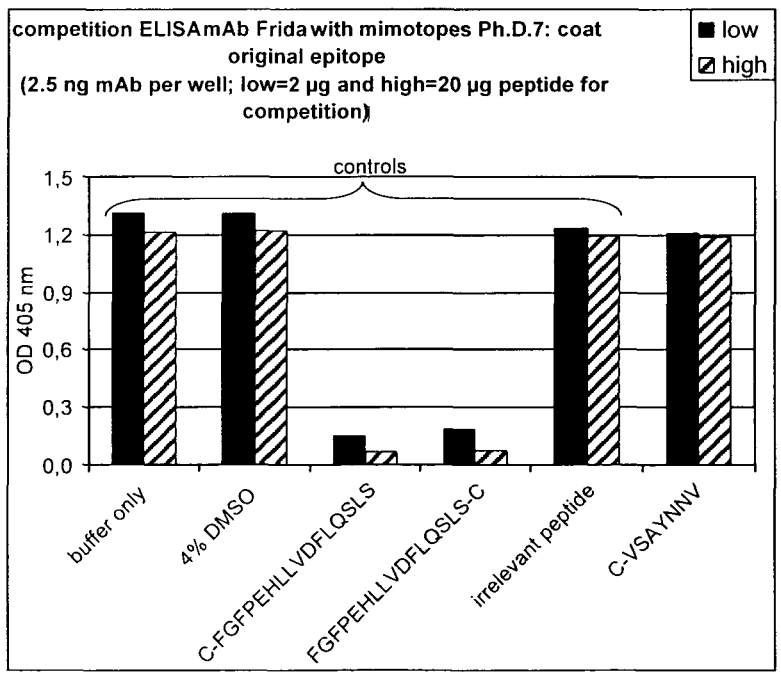

The results of 2 representative competition ELISAs with mAb "Frida" are shown in FIGS. 3A and 3b. The same pattern was seen with mAb "James".

3.2.2. Phage Display Library Ph.D. 12
3.2.2.1. Screening with Monoclonal Antibody "Frida"

```
Fr12/2/6     TPTHYYADFSQL (SEQ ID NO. 67)

Fr12/2/11    LPGHLIWDSLHY (SEQ ID NO. 68)

Fr12/2/27    LPQTHPLHLLED (SEQ ID NO. 69)

Fr12/3/1

Fr12/3/19

Fr12/3/88    IPYHHLVDQLHH (SEQ ID NO. 70)

Fr12/3/26

Fr12/3/65    YPYHVQVDVLQN (SEQ ID NO. 71)

Fr12/3/68    IPSHHLQDSLQL (SEQ ID NO. 72)

Fr12/3/12    EYAHHTSLDLRQ (SEQ ID NO. 73)

Fr12/3/83    EPLHFRSDRIQA (SEQ ID NO. 74)

Fr12/3/55    ATPSHLIIDRAQ (SEQ ID NO. 75)

Fr12/3/63    APKHLYADMSQA (SEQ ID NO. 76)

Fr12/3/84    FKPAHVSIDWLQ (SEQ ID NO. 77)

Fr12/3/47    MPAHLSRDLRQS (SEQ ID NO. 78)

Fr12/3/80    NPKHYSIDRHQA (SEQ ID NO. 79)

Fr12/3/40    SPQHLTTDRAQA (SEQ ID NO. 80)

Fr12/3/35    TPFHFAQDSWQW (SEQ ID NO. 81)
```

Figure 4A:
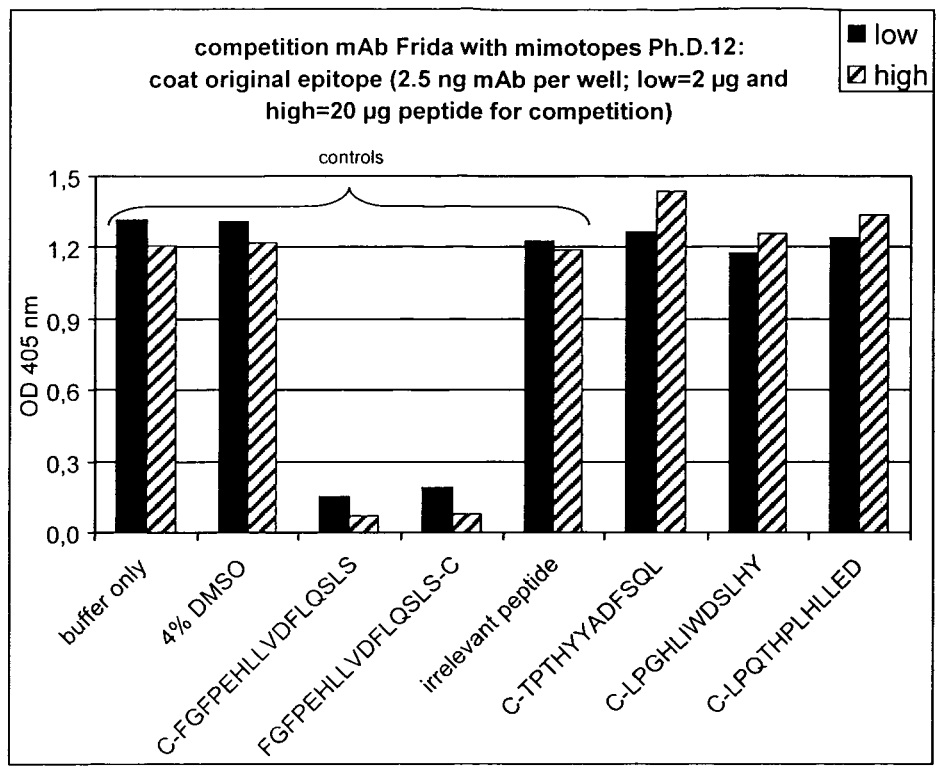
Figure 4B:
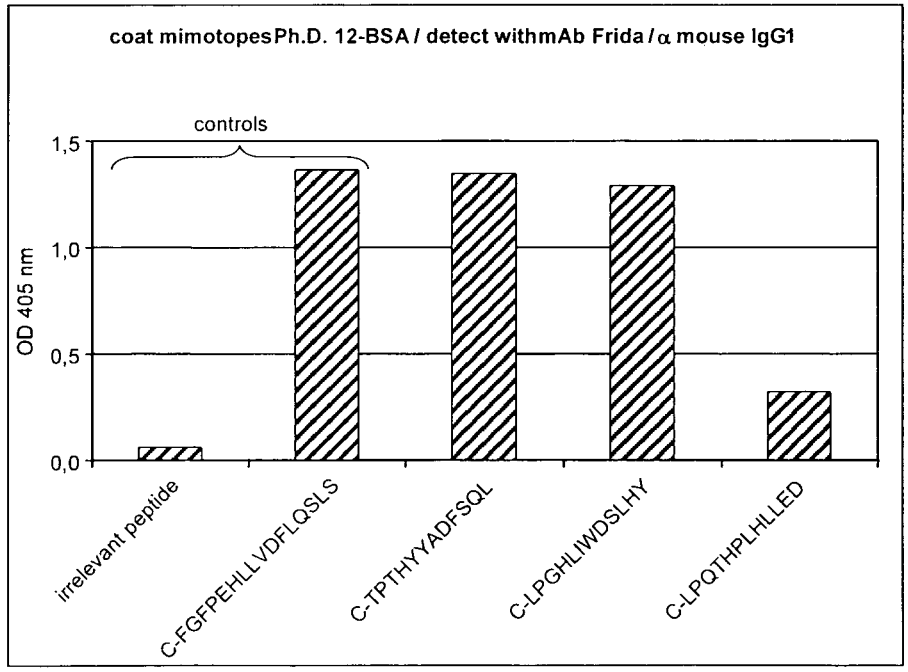

None of the 15 amino acid sequences identified in this screen were inhibiting in in vitro competition experiments. However, sequence analysis revealed rather high homology to the original protein sequence for many of the mimotopes. On the other hand, for some peptides binding of monoclonal antibody "Frida" to ELISA plates coated with mimotope-BSA could be shown (see FIGS. 4a and 4b).

This shows that binding of monoclonal antibody to immobilised mimotopes does not necessarily allow to predict inhibition in in vitro competition ELISA.

In vitro inhibition experiments with variations of the original sequence FGFPEHLLVDFLQSLS (SEQ ID NO. 147) (16 C-terminal AA of CETP protein) showed that removing more than 2 amino acids from the N-terminus or more than 1 amino acid from the C-terminus abolishes inhibition (for monoclonal antibodies "Frida" and "James". "Paula" and "Felix" recognise a different part of the original sequence).

In addition, simultaneously removing 2 amino acids from the N-terminus and 1 amino acid from the C-terminus also results in a peptide that is not inhibiting in vitro any more.

C-FGFPEHLLVDFLQSLS (SEQ ID NO. 147) "original" sequence (peptide derived from CETP)/inhibiting in vitro C-GFPEHLLVDFLQSLS sequence N-1/inhibiting in vitro C-FPEHLLVDFLQSLS sequence N-2/inhibiting in vitro C-PEHLLVDFLQSLS sequence N-3/evtl. slightly inhibiting in vitro C-FGFPEHLLVDFLQSL sequence C-1/inhibiting in vitro C-FGFPEHLLVDFLQS sequence C-2/not inhibiting in vitro C-FPEHLLVDFLQSL sequence N-2 and C-1/not inhibiting in vitro!

"original" FGFPEHLLVDFLQSLS

| | |
|---|---|
| Fr12/2/6 | TPTHYYADFSQL (SEQ ID NO. 67) |
| Fr12/2/11 | LPGHLIWDSLHY (SEQ ID NO. 68) |
| Fr12/2/27 | LPQTHPLHLLED (SEQ ID NO. 69) |
| Fr12/3/1 | IPYHHLVDQLHH (SEQ ID NO. 70) |
| Fr12/3/19 | IPYHHLVDQLHH (SEQ ID NO. 70) |
| Fr12/3/88 | IPYHHLVDQLHH (SEQ ID NO. 70) |
| Fr12/3/26 | YPYHVQVDVLQN (SEQ ID NO. 71) |
| Fr12/3/65 | YPYHVQVDVLQN (SEQ ID NO. 71) |
| Fr12/3/68 | IPSHHLQDSLQL (SEQ ID NO. 72) |
| Fr12/3/12 | EYAHHTSLDLRQ (SEQ ID NO. 73) |
| Fr12/3/83 | EPLHFRSDRIQA (SEQ ID NO. 74) |
| Fr12/3/55 | ATPSHLIIDRAQ (SEQ ID NO. 75) |
| Fr12/3/63 | APKHLYADMSQA (SEQ ID NO. 76) |
| Fr12/3/84 | FKPAHVSIDWLQ (SEQ ID NO. 77) |
| Fr12/3/47 | MPAHLSRDLRQS (SEQ ID NO. 78) |
| Fr12/3/80 | NPKHYSIDRHQA (SEQ ID NO. 79) |
| Fr12/3/40 | SPQHLTTDRAQA (SEQ ID NO. 80) |
| Fr12/3/35 | TPFHFAQDSWQW (SEQ ID NO. 81) |

Consequently, using the original CETP sequence as a template, peptide sequences obtained in this Phage Display procedure were elongated on the N-terminus and/or C-terminus to check whether in vitro inhibition is possible with longer peptides.

3.2.2.2. Mimotopes Frida Ph.D. 12 and Variations Thereof:

```
Fr12/2/6              TPTHYYADFSQL
                      (SEQ ID NO. 67)

Fr12/2/6              TPTHYYADFSQLLS
ext1                  (SEQ ID NO. 82)

Fr12/2/6              TPTHYYADFSQSLS
ext2                  (SEQ ID NO. 83)

Fr12/2/6              GTPTHYYADFSQLL
ext3                  (SEQ ID NO. 84)

Fr12/2/6              GTPTHYYADFSQSL
ext4                  (SEQ ID NO. 85)

Fr12/2/6              FGTPTHYYADFSQSLS
ext5                  (SEQ ID NO. 86)

Fr12/2/6              FGFPTHYYADFSQSLS
ext6                  (SEQ ID NO. 87)

Fr12/2/11             LPGHLIWDSLHY
                      (SEQ ID NO. 68)

Fr12/2/11             LPGHLIWDSLHYL
ext1                  (SEQ ID NO. 89)

Fr12/2/11             LPGHLIWDSLHYLS
ext2                  (SEQ ID NO. 90)

Fr12/2/11             LPGHLIWDSLHSL
ext3                  (SEQ ID NO. 91)

Fr12/2/11             LPGHLIWDSLHSLS
ext4                  (SEQ ID NO. 92)

Fr12/2/11             GLPGHLIWDSLHYL
ext5                  (SEQ ID NO. 93)

Fr12/2/11             GLPGHLIWDSLHSL
ext5                  (SEQ ID NO. 94)

Fr12/2/11             FGFPGHLIWDSLHSLS
ext6                  (SEQ ID NO. 95)

Fr12/2/11             FGFPGHLIWDSLHSLS
ext7                  (SEQ ID NO. 96)

Fr12/2/27             LPQTHPLHLLED
                      (SEQ ID NO. 69)

Fr-                   IPYHHLVDQLHLS
12/3/1/19/88          (SEQ ID NO. 99)
ext1

Fr-                   IPYHHLVDQLHSLS
12/3/1/19/88          (SEQ ID NO. 100)
ext2

Fr-                   FGIPYHHLVDQLHHLS
12/3/1/19/88          (SEQ ID NO. 101)
ext3

Fr-                   FGFPYHHLVDQLHSLS
12/3/1/19/88          (SEQ ID NO. 102)
ext4

Fr-                   YPYHVQVDVLQNLS
12/3/26/65            (SEQ ID NO. 104)
ext1

Fr-                   YPYHVQVDVLQSLS
12/3/26/65            (SEQ ID NO. 105)
ext2

Fr-                   FGYPYHVQVDVLQNLS
12/3/26/65            (SEQ ID NO. 106)
ext3

Fr-                   FGFPYHVQVDVLQSLS
12/3/26/65            (SEQ ID NO. 107)
ext4

Fr12/3/68             IPSHHLQDSLQLLS
ext1                  (SEQ ID NO. 109)

Fr12/3/68             IPSHHLQDSLQSLS
ext2                  (SEQ ID NO. 110)

Fr12/3/68             GIPSHHLQDSLQLL
ext3                  (SEQ ID NO. 111)

Fr12/3/68             FGIPSHHLQDSLQLLS
ext4                  (SEQ ID NO. 112)

Fr12/3/68             FGFPSHHLQDSLQSLS
ext5                  (SEQ ID NO. 113)

Fr12/3/83             EPLHFRSDRIQALS
ext1                  (SEQ ID NO. 116)

Fr12/3/83             EPLHFRSDRIQSLS
ext2                  (SEQ ID NO. 117)

Fr12/3/83             GEPLHFRSDRIQAL
ext3                  (SEQ ID NO. 118)

Fr12/3/83             FGEPLHFRSDRIQALS
ext4                  (SEQ ID NO. 119)

Fr12/3/83             FGFPLHFRSDRIQSLS
ext5                  (SEQ ID NO. 120)

Fr12/3/55             ATPSHLIIDRAQSLS
ext1                  (SEQ ID NO. 176)

Fr12/3/55             FGFPSHLIIDRAQSLS
ext2                  (SEQ ID NO. 177)

Fr12/3/55             FGFPSHLIIDWAQSLS
ext2 R->W             (SEQ ID NO. 178)

Fr12/3/55             FGFPSHLIIDWAQSLS
ext2                  (SEQ ID NO. 179)
RA->WL Fr12/3/63             APKHLYADMSQALS
ext1                  (SEQ ID NO. 122)

Fr12/3/63             APKHLYADMSQSLS
ext2                  (SEQ ID NO. 123)

Fr12/3/63             GAPKHLYADMSQAL
ext3                  (SEQ ID NO. 124)

Fr12/3/63             FGFPKHLYADMSQSLS
ext4                  (SEQ ID NO. 125)

Fr12/3/84             FKPAHVSIDWLQSLS
ext1                  (SEQ ID NO. 183)

Fr12/3/84             FGFPAHVSIDWLQSLS
ext2                  (SEQ ID NO. 184)

Fr12/3/47             MPAHLSRDLRQSL
ext1                  (SEQ ID NO. 127)

Fr12/3/47             MPAHLSRDLRQSLS
ext2                  (SEQ ID NO. 128)

Fr12/3/47             GMPAHLSRDLRQSL
ext3                  (SEQ ID NO. 129)

Fr12/3/47             FGFPAHLSRDLRQSLS
ext4                  (SEQ ID NO. 130)

Fr12/3/40             SPQHLTTDRAQALS
ext1                  (SEQ ID NO. 168)
```

-continued

| | | |
|---|---|---|
| Fr12/3/40 ext2 | SPQHLTTDRAQSLS | (SEQ ID NO. 169) |
| Fr12/3/40 ext3 | GSPQHLTTDRAQAL | (SEQ ID NO. 170) |
| Fr12/3/40 ext4 | FGFPQHLTTDRAQSLS | (SEQ ID NO. 171) |
| Fr12/3/35 ext1 | TPFHFAQDSWQWLS | (SEQ ID NO. 133) |
| Fr12/3/35 ext2 | TPFHFAQDSWQSLS | (SEQ ID NO. 134) |
| Fr12/3/35 ext3 | GTPFHFAQDSWQWL | (SEQ ID NO. 135) |
| Fr12/3/35 ext4 | FGFPFHFAQDSWQSLS | (SEQ ID NO. 136) |

Figure 5A:
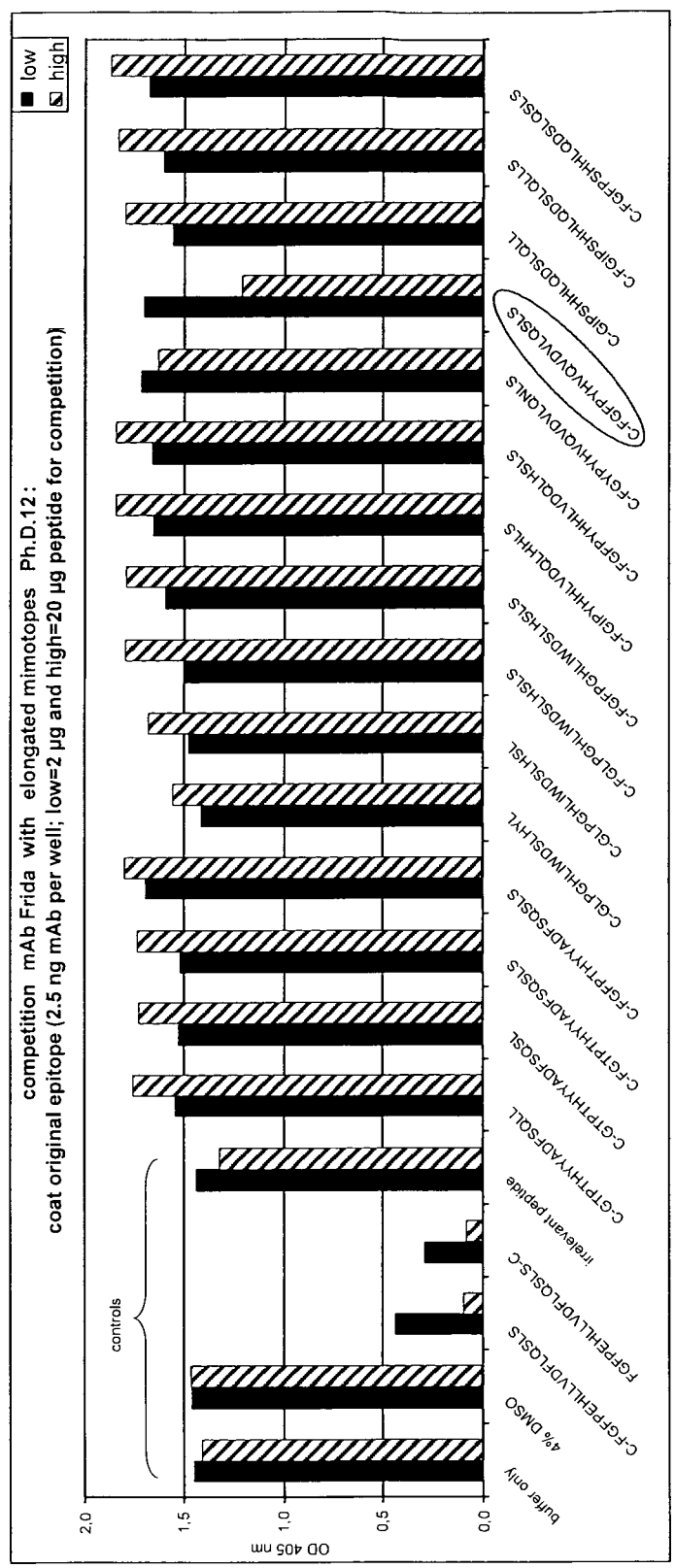
Figure 5B:
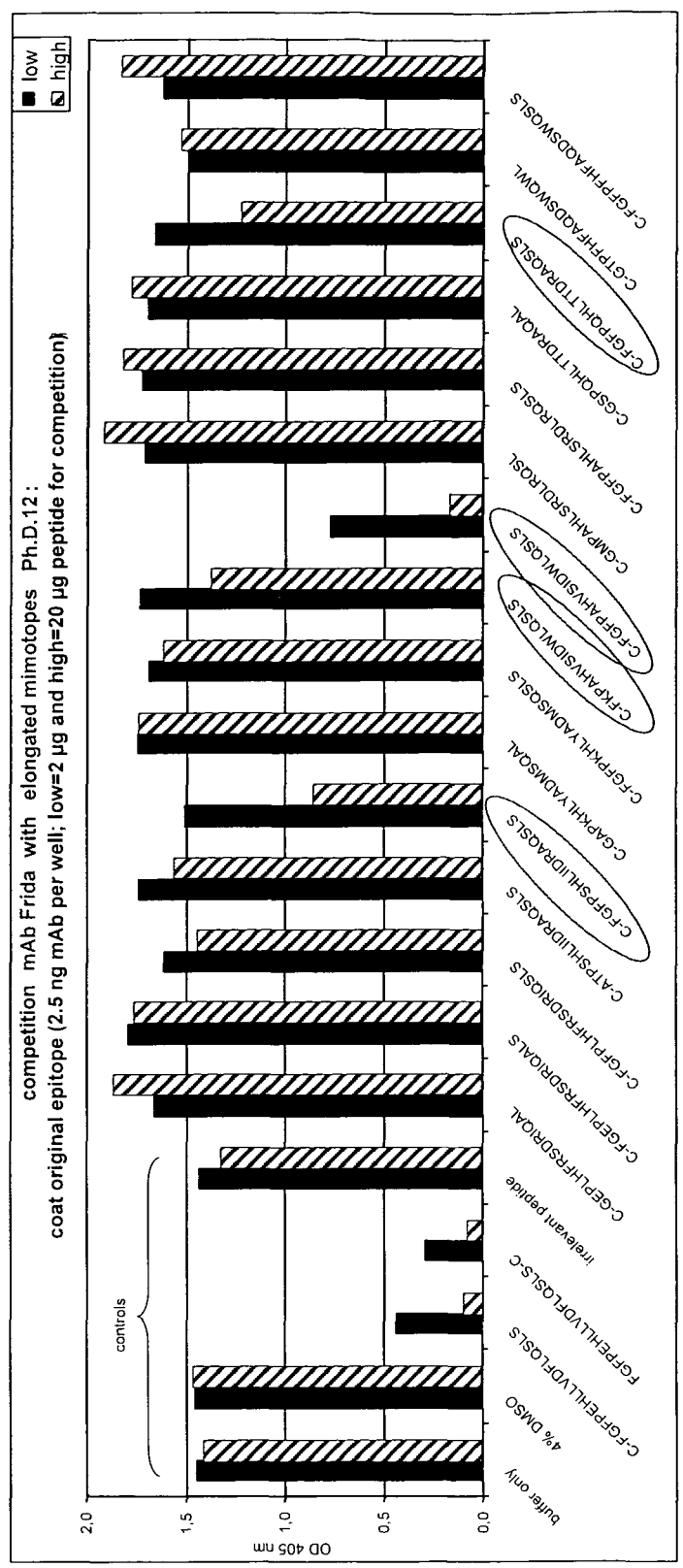

Representative examples of inhibition ELISA are shown in FIGS. 5A and 5b. The elongated peptides Fr12/3/84 ext2 and Fr12/3/55 ext3 showed a significant inhibition:

C-FGFPSHLIIDRAQSLS  Fr12/3/55 ext3 (SEQ ID NO. 177)

C-FGFPAHVSIDWLQSLS  Fr12/3/84 ext2 (SEQ ID NO. 184)

Three additional peptides were also inhibiting in this assay:

| | |
|---|---|
| C-FGFPYHVQVDVLQSLS | Fr12/3/26/65 ext4 (SEQ ID NO. 107) |
| C-FKPAHVSIDWLQSLS | Fr12/3/84 ext1 (SEQ ID NO. 183) |
| C-FGFPQHLTTDRAQSLS | Fr12/3/40 ext4 (SEQ ID NO. 171) |

After sequence analysis comparing the original epitope and all mimotopes derived from Phage Display screens additional 2 peptides were created.

For mimotope Fr12/3/55 ext3 C-FGFPSHLIIDRAQSLS (SEQ ID NO. 177) (inhibiting in ELISA, see above) amino acid exchanges were tested in inhibition ELISA:

Strongly inhibiting:

C-FGFPAHVSIDWLQSLS (SEQ ID NO. 184)  Fr12/3/84 ext2

Slightly inhibiting:

C-FGFPSHLIIDRAQSLS (SEQ ID NO. 177)  Fr12/3/55 ext3

Figure 6:
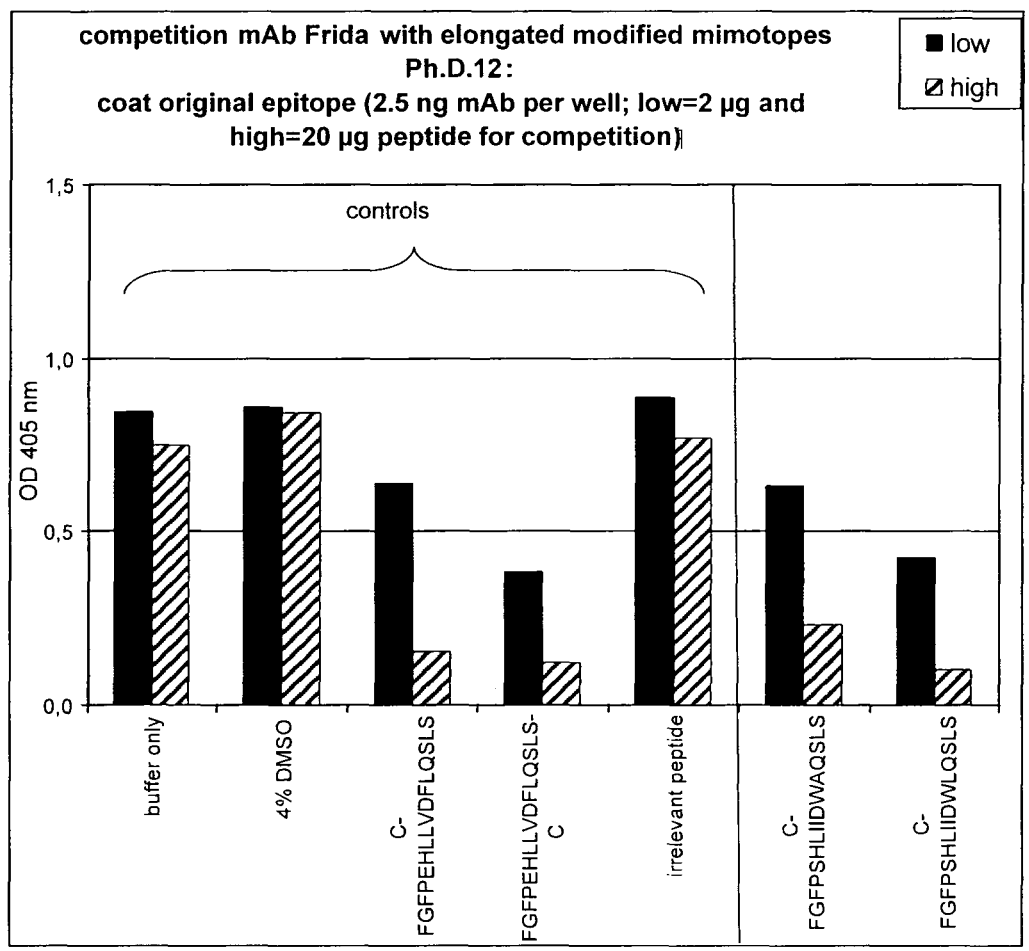
Figure 7A:
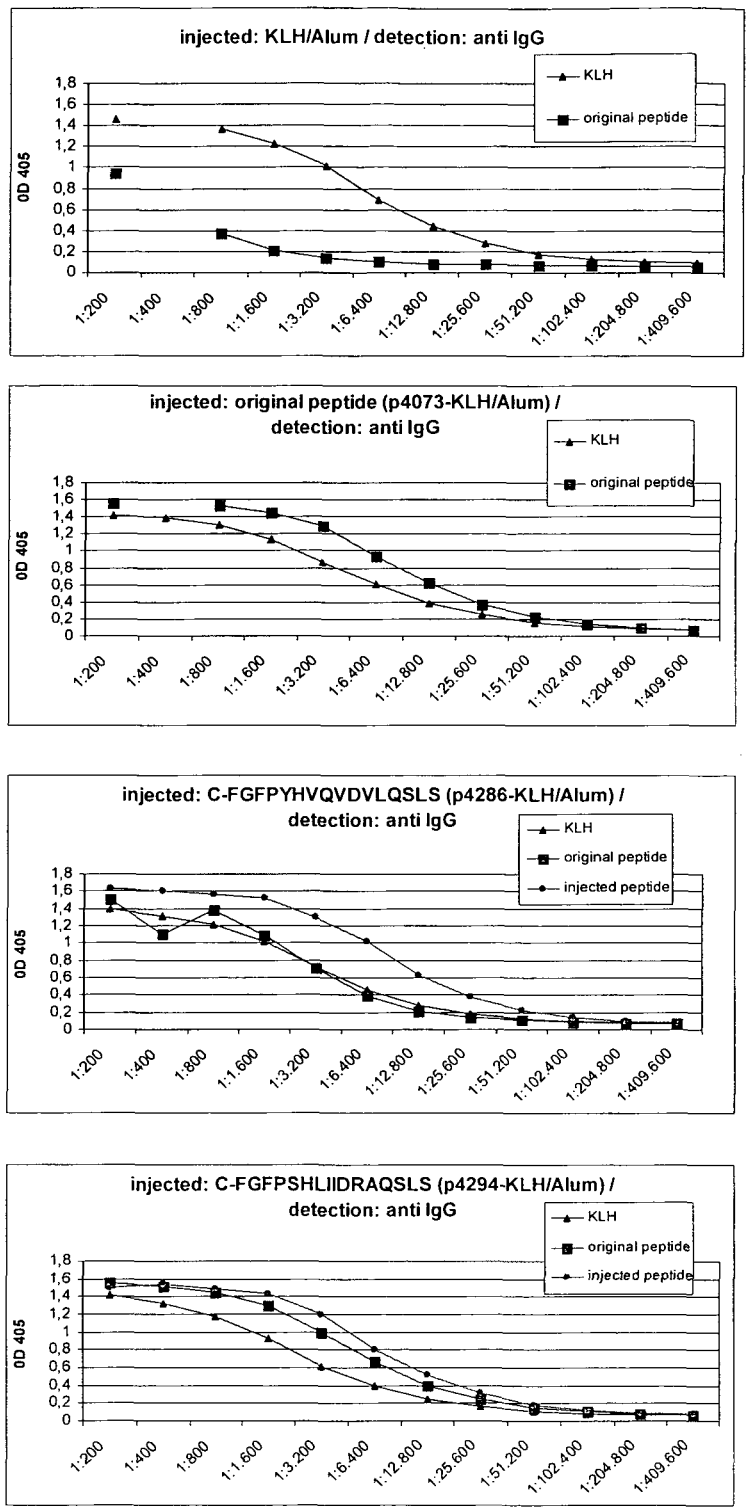
Figure 7B:
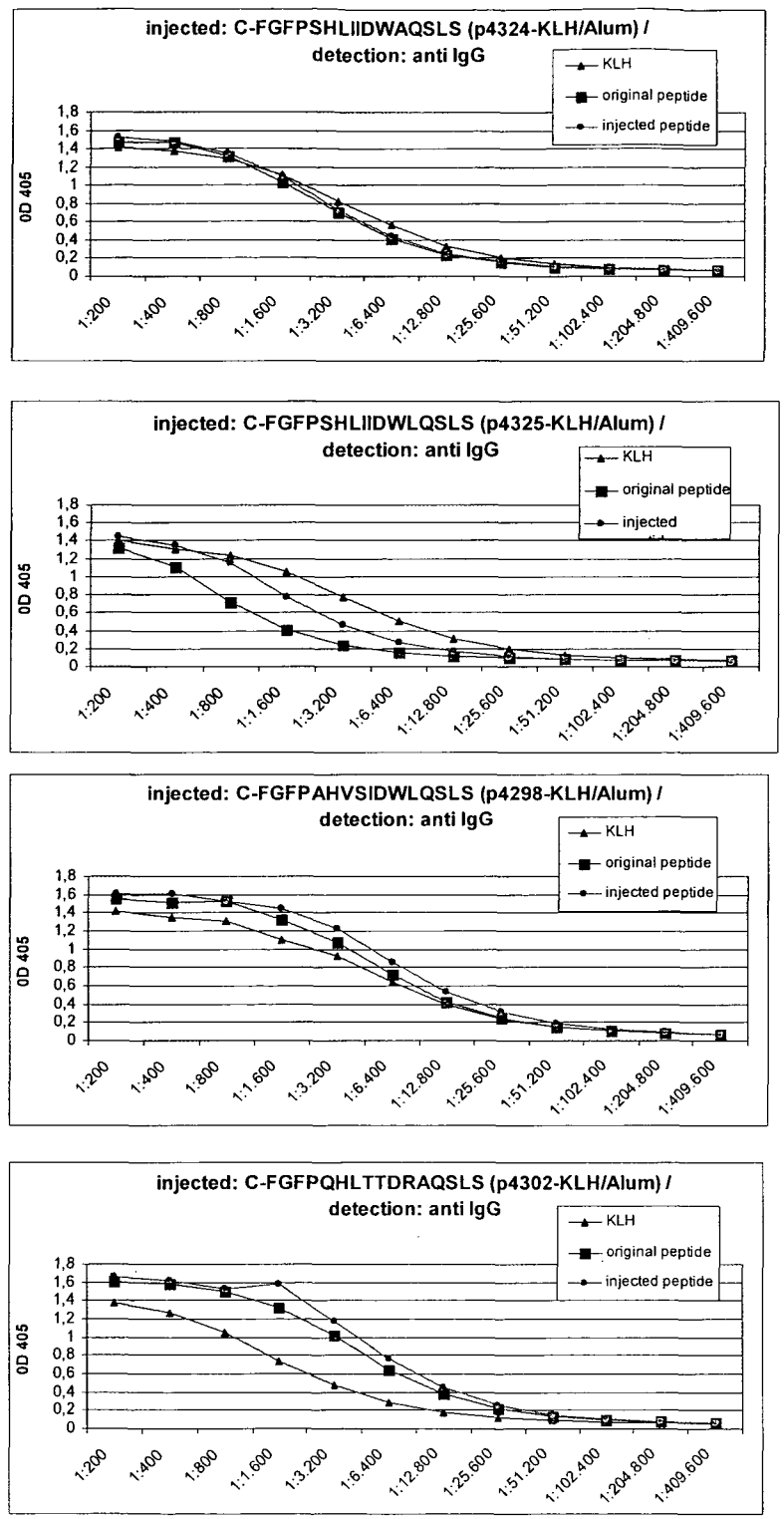
Figure 7C:
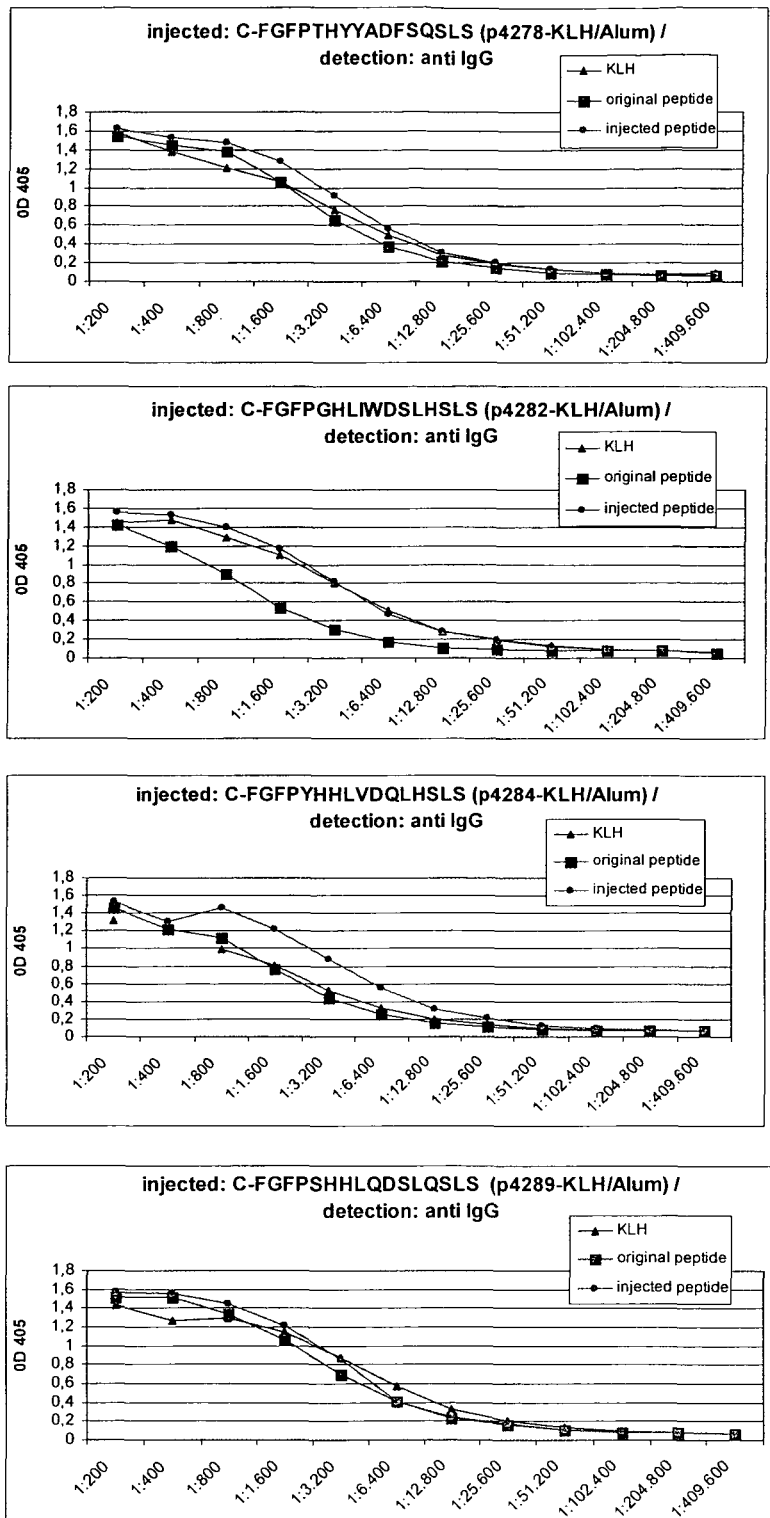
Figure 7D:
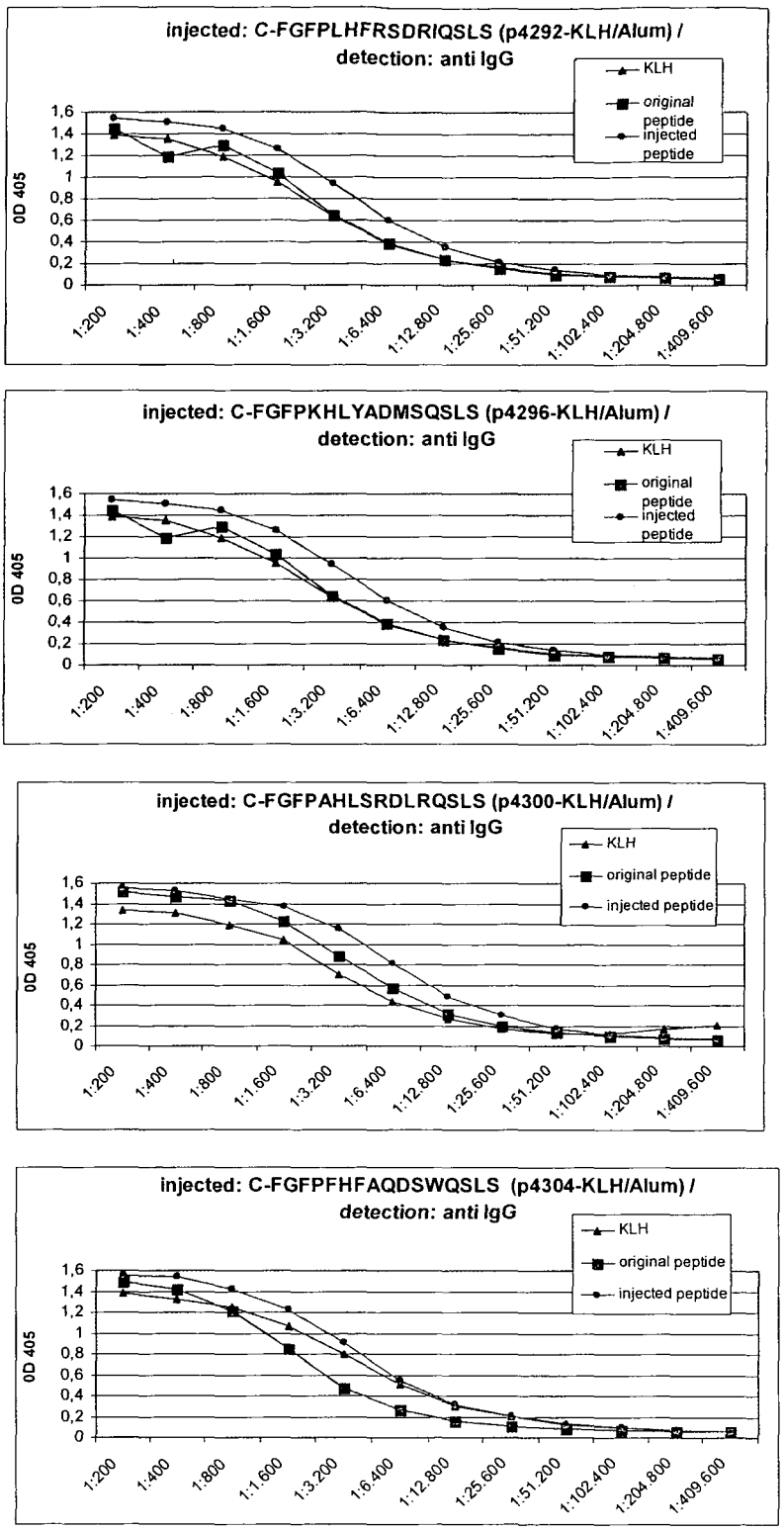
Figure 8A:
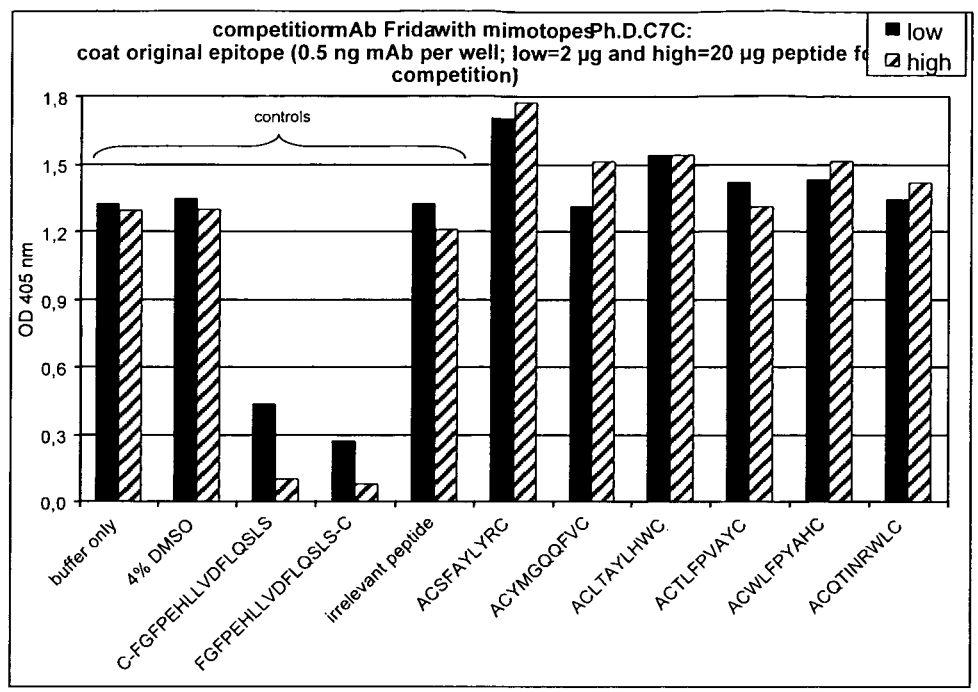
Figure 8B:
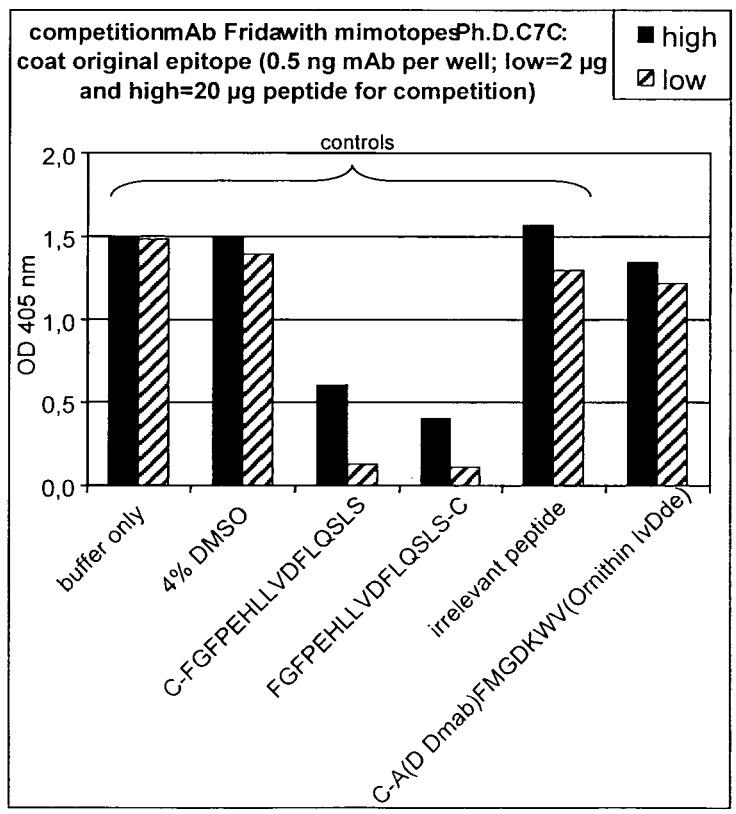
Figure 9:
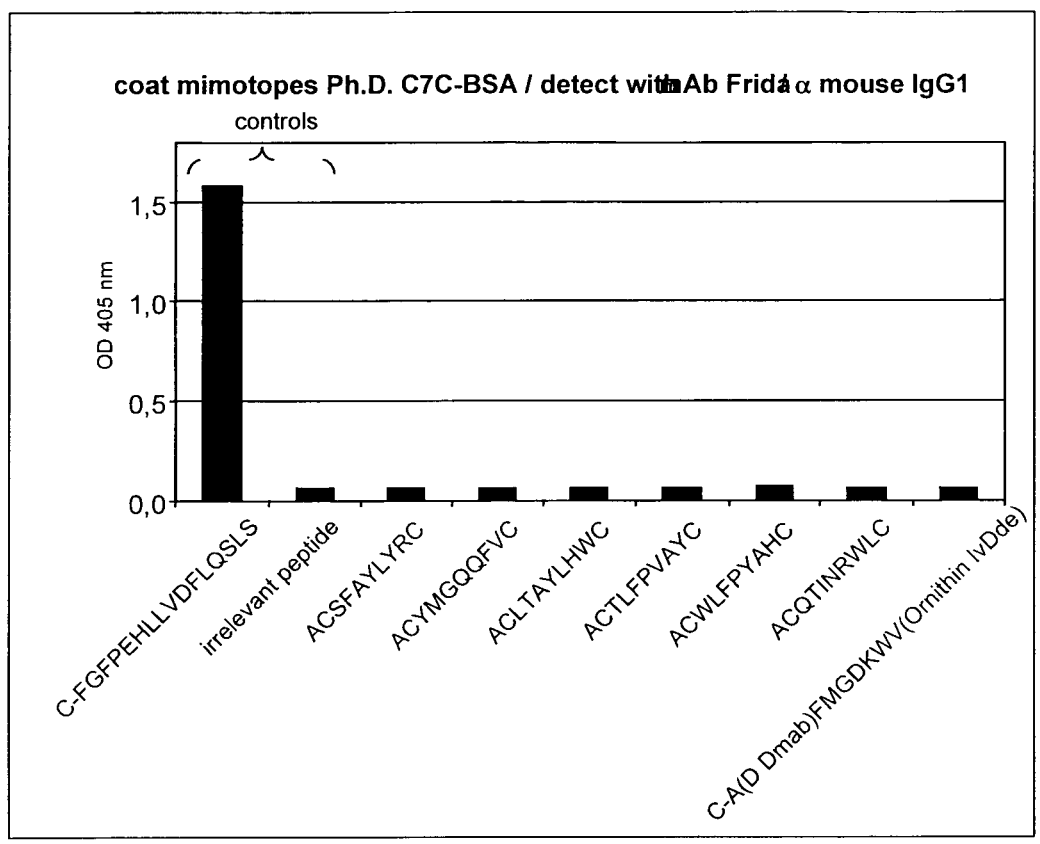
Figure 10A:
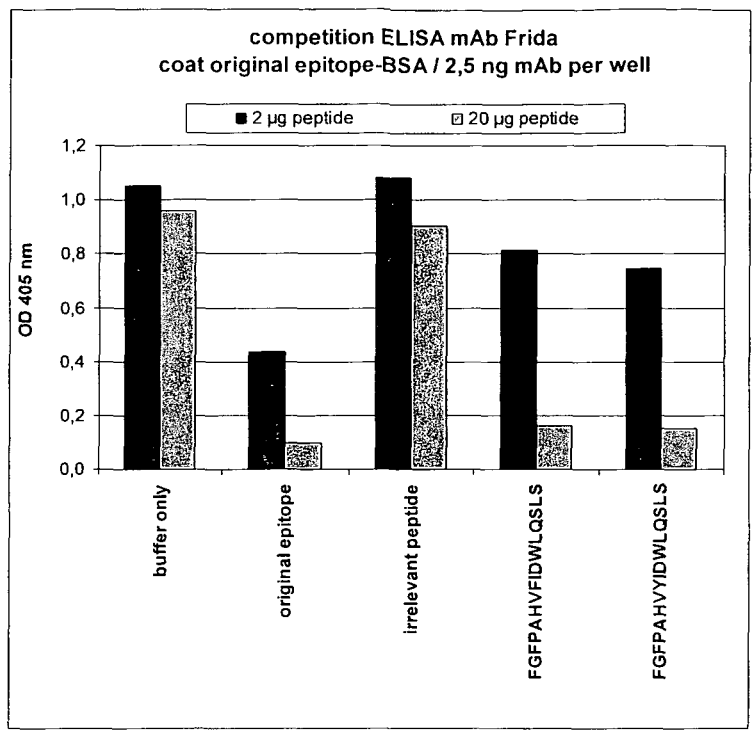
Figure 10B:
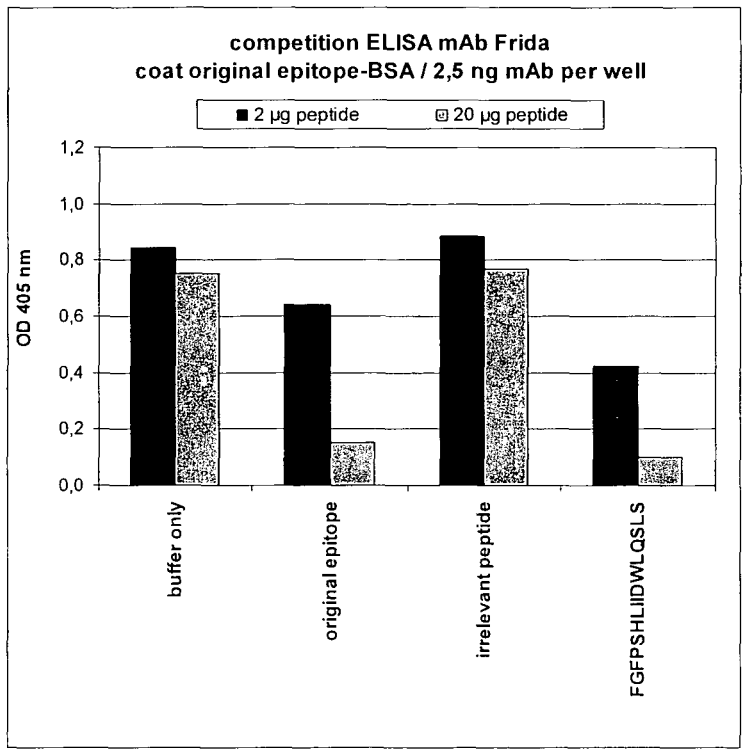
Figure 11:
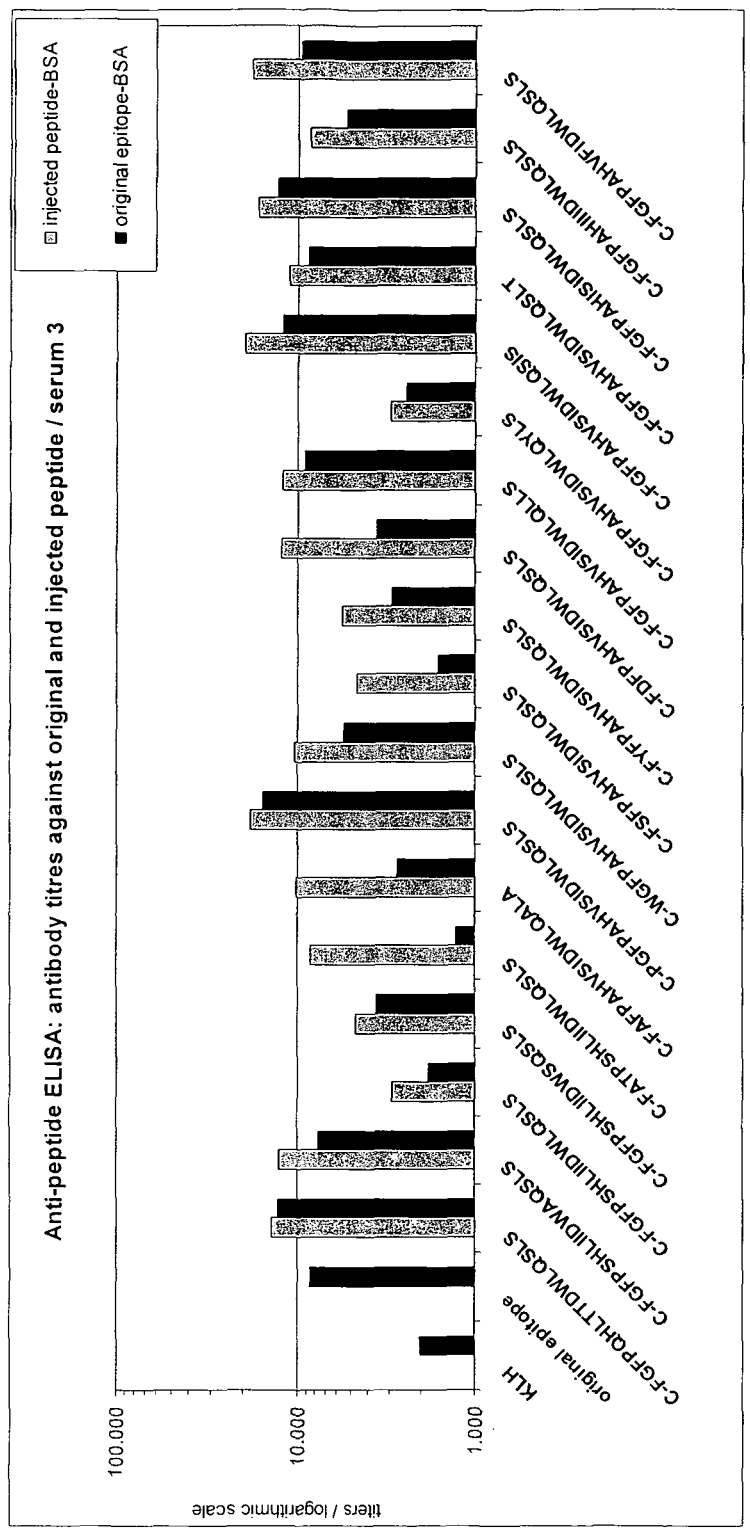
Figure 12A:
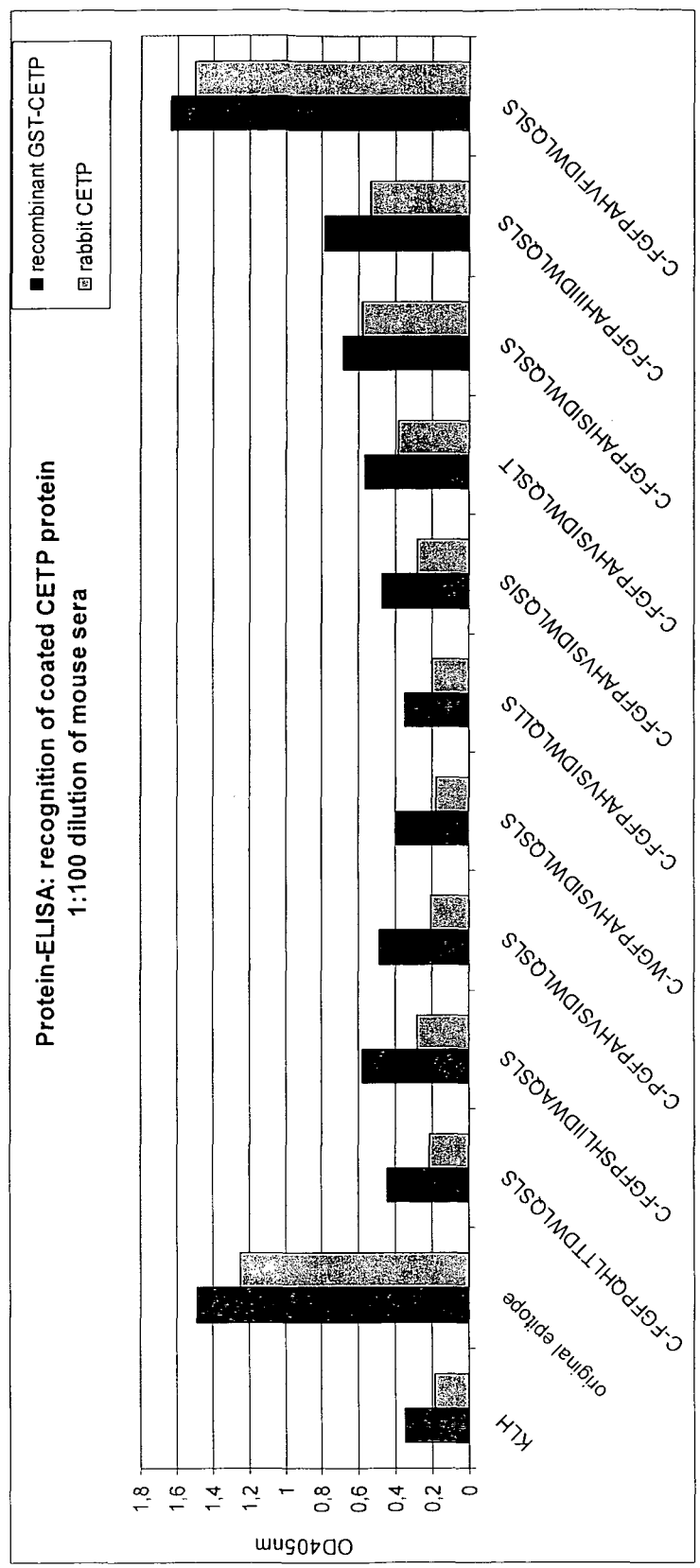
Figure 12B:
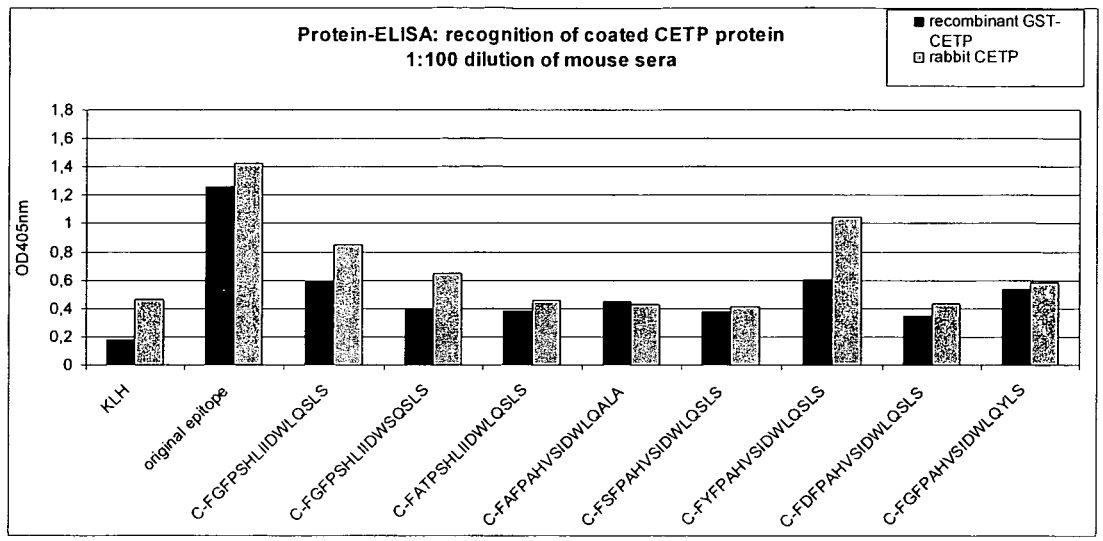
Figure 13:
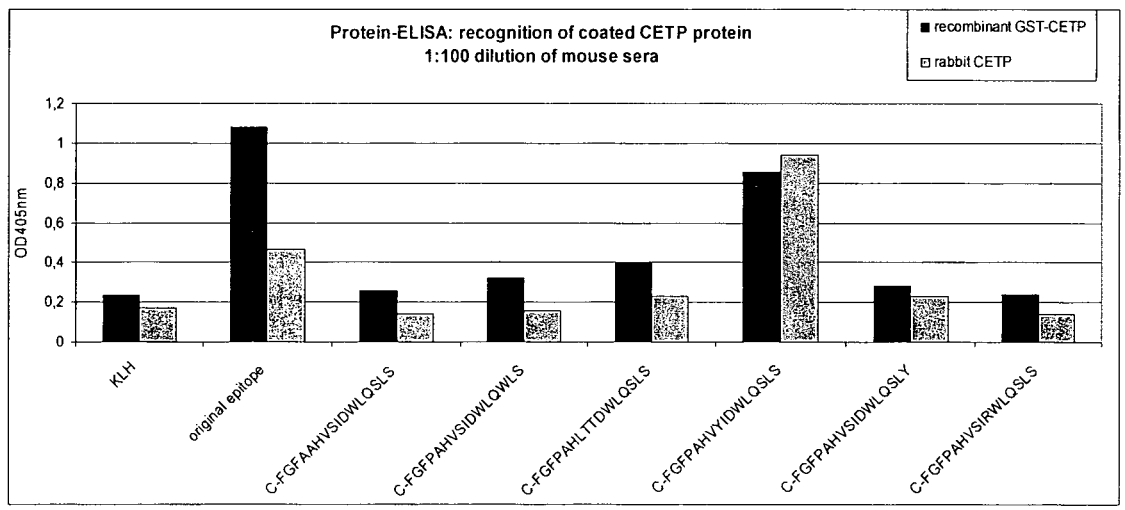
Figure 14:
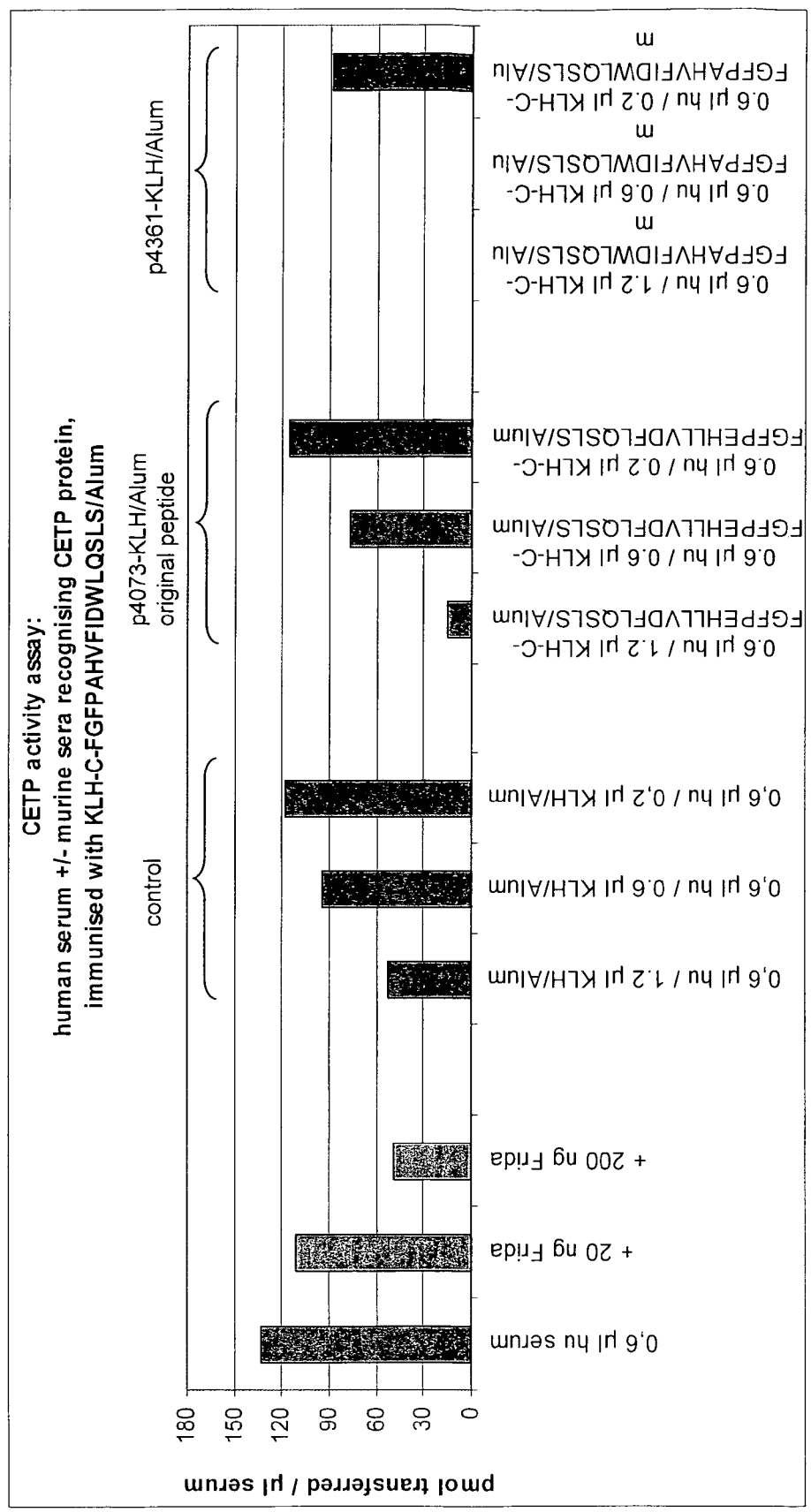
Figure 15:
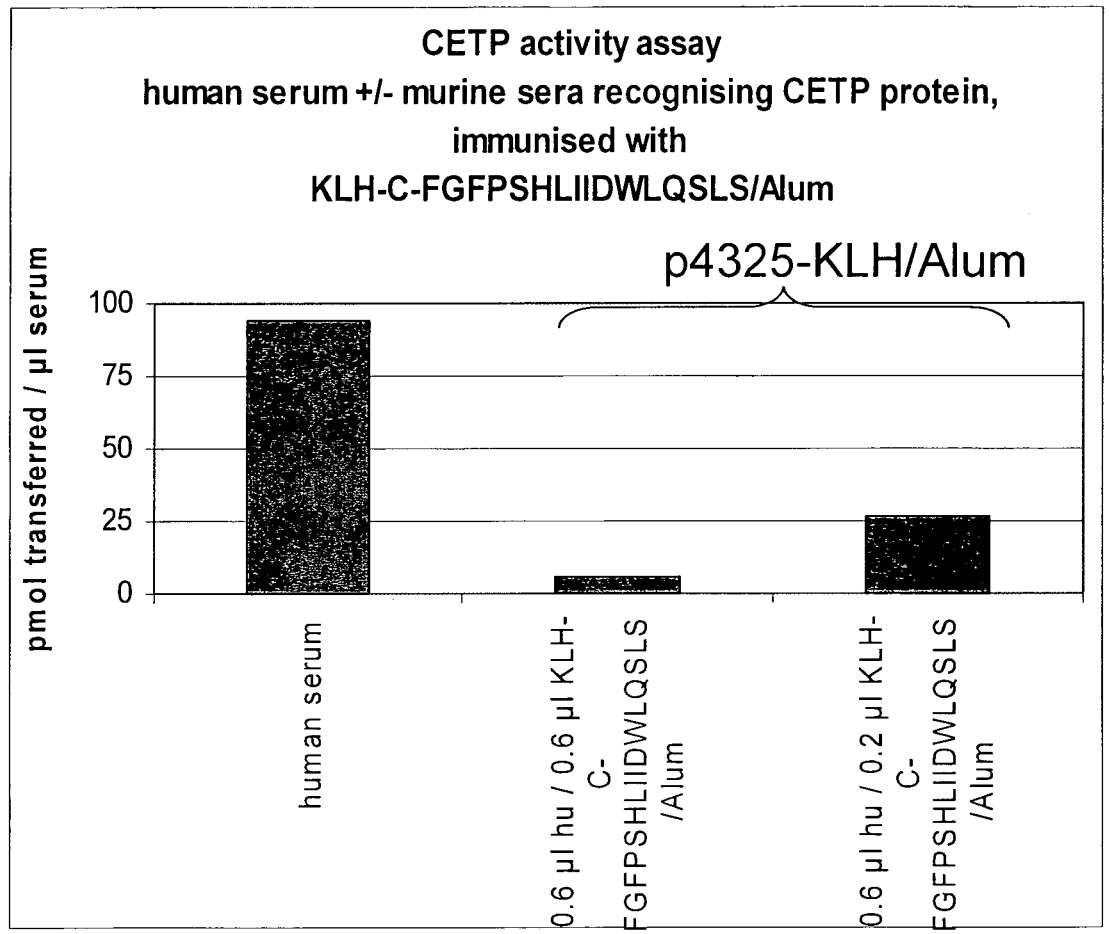
FIG. 15 shows that the addition of p4325-KLH/Alum to human serum inhibits significantly CETP activity.
Figure 16:
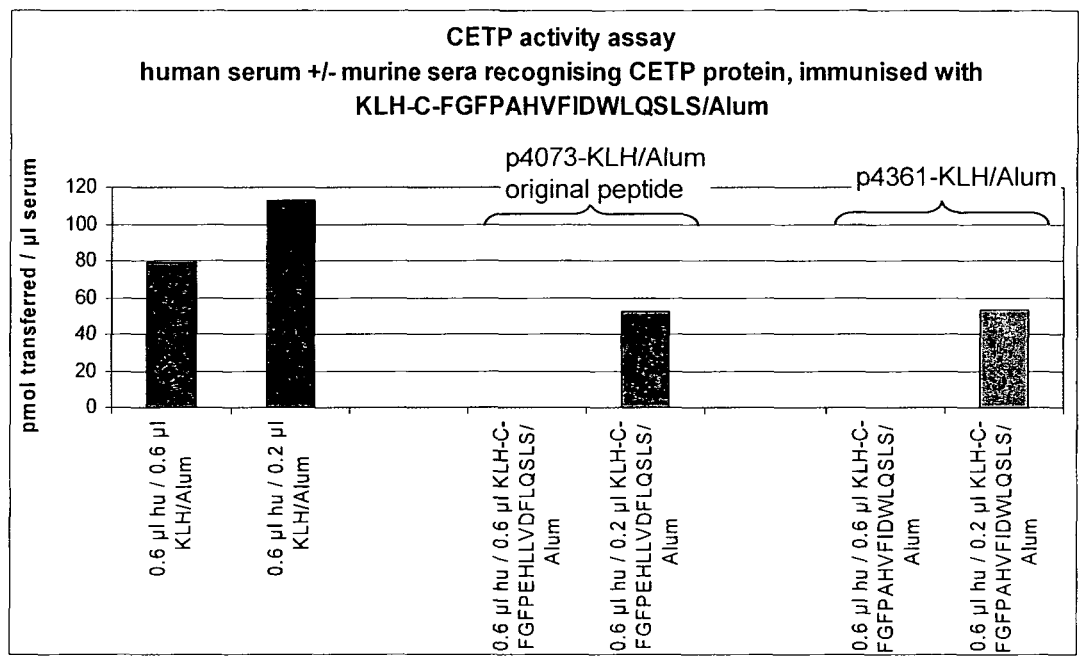
FIG. 16 shows that the addition of p4361-KLH/Alum to human serum inhibits significantly CETP activity.

Peptides with altered sequences (inhibiting, see FIG. 6):

C-FGFPSHLIIDWAQSLS (SEQ ID NO. 178) Fr12/3/55 ext2 W instead of R

C-FGFPSHLIIDWLQSLS (SEQ ID NO. 179) Fr12/3/55 ext2 WL instead of RA

Further preferred mimotopes have been characterised by the following example-set-up:

| Exp. Nr. CETP-42 | | | | |
|---|---|---|---|---|
| C42-1 | | | KLH/Alum | — |
| | C42-2 | | p4073-KLH/Alum | C-FGFPEHLLVDFLQSLS (SEQ ID NO. 147) |
| | C42-3 | p4073 LLV->LFV | p4468-KLH/Alum | C-FGFPEHL_F_VDFLQSLS (SEQ ID NO. 252) |
| | C42-4 | Fr12/3/84 ext2 VSI->VFI | P4361-KLH/Alum | C-FGFPAHV_F_IDWLQSLS (SEQ ID NO. 222) |
| | C42-5 | Fr12/3/84 ext2 VSI->VHI | p4469-KLH/Alum | C-FGFPAHV_H_IDWLQSLS (SEQ ID NO. 253) |
| | C42-6 | Fr12/3/84 ext2 VSI->V?I | p4470-KLH/Alum | C-FGFPAHV_P_IDWLQSLS (SEQ ID NO. 254) |
| | C42-7 | Fr12/3/84 ext2 VSI->VWI | p4471-KLH/Alum | C-FGFPAHV_W_IDWLQSLS (SEQ ID NO. 229) |
| | C42-8 | Fr12/3/55 ext2 R->W LII->LFI | p4472-KLH/Alum | C-FGFPSHL_F_IDWAQSLS (SEQ ID NO. 255) |
| | C42-9 | Fr12/3/84 ext2 VSIδVFI FGF->PGF SLS->LIT | p4473-KLH/Alum | C-_P_GFPAHV_F_IDWLQ_LIT_ (SEQ ID NO. 256) |
| | C42-10 | Fr12/3/84 ext2 VSI->VYI | P4362-KLH/Alum | C-FGFPAHV_Y_IDWLQSLS (SEQ ID NO. 223) |
| Exp. Nr. CETP-45 | | | | |
| C45-1 | | | KLH/Alum | — |
| | C45-2 | | p1358-KLH/Alum | neg. control peptide |

-continued

| | | | |
|---|---|---|---|
| C45-3 | | p4073-KLH/Alum | C-FGFPEHLLVDFLQSLS (SEQ ID NO. 147) |
| C45-4 | Fr12/3/84 ext2 VSI->VFI SLS->SLN | p4474-KLH/Alum | C-FGFPAHVFIDWLQSLN (SEQ ID NO. 230) |
| C45-5 | Fr12/3/84 ext2 VSI->FSI | p4475-KLH/Alum | C-FGFPAHFSIDWLQSLS (SEQ ID NO. 231) |
| C45-6 | Fr12/3/84 ext2 VSI->VSF | p4476-KLH/Alum | C-FGFPAHVSFDWLQSLS (SEQ ID NO. 232) |
| C45-7 | Fr12/3/84 ext2 VSI->VFI PAH->PEH | p4477-KLH/Alum | C-FGFPEHVFIDWLQSLS (SEQ ID NO. 233) |
| C45-8 | Fr12/3/1/19/88 ext4 | p4284-KLH/Alum | C-FGFPYHHLVDQLHSLS (SEQ ID NO. 102) |
| C45-9 | Fr12/3/84 ext1 VSI->VFI plus G on N-terminus | p4479-KLH/Alum | C-GFKPAHVFIDWLQSLS (SEQ ID NO. 270) |
| C45-10 | Fr12/3/84 ext2 VSI->VFI plus D on N-terminus; = 4361 plus D | p4480-KLH/Alum | C-DFGFPAHVFIDWLQSLS (SEQ ID NO. 234) |
| C45-11 | Fr12/3/40 ext4 RA->WL LTT->LFT = p4369 with exchange TδF | p4481-KLH/Alum | C-FGFPQHLFTDWLQSLS (SEQ ID NO. 237) |
| C45-12 | Fr12/3/55 ext2 RA->WL (see C-31 and C-33; sera inhibiting activity) | p4325-KLH/Alum | C-FGFPSHLIIDWLQSLS (SEQ ID NO. 179) |
| C45-13 | Fr12/3/84 ext2 FGF->FYF (see C-33: recogn. protein/not inhibiting activity) | p4343-KLH/Alum | C-FYFPAHVSIDWLQSLS (SEQ ID NO. 204) |
| C45-14 | rabbit sequence | p4125-KLH/Alum | C-FGFPKHLLVDFLQSLS (SEQ ID NO. 238) |

3.2.2.3. In Vivo Testing of Mimotopes

Female Balb/c mice, five mice per group, were subcutaneously immunized with 30 μg peptide coupled to KLH. Control groups were administered KLH or C-FGFPEHLLVDFLQSLS (SEQ ID NO. 147). As adjuvant alum was used. The peptides administered were all able to bind to "Frida" and to induce an immune response for CETP, although some of these peptides did not inhibit the binding of CETP to "Frida" in vitro (in an in vitro inhibition assay). The in vitro ELISA assay to determine the antibody titer was performed with pooled sera after two vaccinations in a two week interval (S2; see FIGS. 7*a* to 7*d*). The wells of the ELISA plate were coated with KLH (positive control), mimotope-BSA conjugate, C-FGFPEHLLVDFLQSLS (SEQ ID NO. 147) and a irrelevant peptide-BSA conjugate (negative control). The detection was performed with anti-mouse IgG.

3.2.3. Phage Display Library Ph.D. 7C7

3.2.3.1. Screening with Monoclonal Antibodies "Frida" and "James"

| | |
|---|---|
| Fr2-1 | ACSFAYLYRC (SEQ ID NO. 137) |
| Fr2-5 | |
| Fr2-6 | |
| Fr2-18 | |
| Fr2-19 | |
| Fr2-28 | |
| Ja2-5 | |

-continued

| | |
|---|---|
| Ja2-20 | |
| Ja2-23 | |
| Ja2-24 | |
| Ja2-30 | ACFMGDKWVC (SEQ ID NO. 138) |
| Fr2-7 | |
| Fr2-9 | ACVLYPKAIC (SEQ ID NO. 139) |
| Fr2-11 | |
| Ja2-19 | ACYMGQQFVC (SEQ ID NO. 140) |
| Fr2-16 | ACLTAYLHWC (SEQ ID NO. 141) |
| Fr2-20 | ACTLFPVAYC (SEQ ID NO. 142) |
| Fr2-25 | ACWLFPYAHC (SEQ ID NO. 143) |
| Fr2-26 | ACKSINMWLC (SEQ ID NO. 144) |
| Fr2-27 | ACQTINRWLC (SEQ ID NO. 145) |

Due to their cyclic nature of these mimotope-peptides their synthesis is more complicated than the synthesis of linear peptides. Seven out of 9 cyclic sequences were chosen for in vitro analysis in inhibition ELISA (see FIGS. 8*a* and 8*b*). None of these sequences inhibited binding of the monoclonal antibody that was used for Phage Display Screening to the original CETP epitope. In addition, when these peptides were coupled to BSA and coated onto ELISA plate they were not detected by the monoclonal antibody (see FIG. 9). This was in contrast to data with mimotopes derived from the Ph.D.7 or Ph.D.12 libraries, where the monoclonal antibodies bound to most of the identified mimotopes when these peptides were coupled to BSA and coated onto ELISA plates.

Example 3

CETP Activity Assay

The CETP activity assay was performed with assays commercially available (e.g. ROAR CETP Activity Assay) and described, for instance, in the U.S. Pat. No. 5,585,235, U.S. Pat. No. 5,618,683 and U.S. Pat. No. 5,770,355. The assay is performed according to the manufacturers' recommendations.

SUMMARY

The present invention relates to the use of compounds for producing a medicament for preventing and/or treating atherosclerosis, atherosclerosis risk diseases and atherosclerosis sequelae.

The invention claimed is:

1. A method for treating at least one of atherosclerosis, and atherosclerosis sequelae, comprising administering to a subject in need thereof, an effective amount of a medicament comprising a compound, wherein the compound comprises the amino acid sequence (SEQ ID NO. 42)
$FX_8(F)_oPX_9HX_{10}X_{11}X_{12}DX_2X_3X_4X_5X_6X_7$, wherein
$X_8$ is selected from the group consisting of G, A, F, Y and K,
$X_9$ is selected from the group consisting of E, Y, A, Q, K and S,
$X_{10}$ is selected from the group consisting of H, V, L, F and I,
$X_{11}$ is selected from the group consisting of L, W, S, I, F and Y,
$X_{12}$ is V, T, F or I,
$X_5$ is S or Y,
$X_6$ is L, A or I,
$X_7$ is S, N or T,
o is 0 or 1
$X_2$ is an amino acid residue selected from the group consisting of F, W, and Q,
$X_3$ is L or S, and
$X_4$ is Q or H,
wherein the compound does not comprise a 4 to 16 mer polypeptide sequence of the cholesterol ester transport protein (CETP) or a CETP epitope.

2. The method according to claim 1, wherein the compound is coupled to a pharmaceutically acceptable carrier.

3. The method according to claim 1, wherein the compound is formulated for intravenous, subcutaneous or intramuscular administration.

4. The method according to claim 1, wherein the compound is formulated with an adjuvant.

5. The method according to claim 1, wherein the medicament comprises 0.1 ng to 10 mg of the compound.

6. The method according to claim 1, wherein the compound is coupled to Keyhole Limpet Hemocyanin.

7. The method according to claim 1, wherein the compound is formulated with aluminum hydroxide.

8. The method according to claim 5, wherein the medicament comprises 10 ng to 1 mg of the compound.

9. The method according to claim 5, wherein the medicament comprises 100 ng to 10 μg of the compound.

10. The method according to claim 1, wherein the compound is SEQ ID NO:230.

* * * * *